US012296088B2

(12) United States Patent
Teh et al.

(10) Patent No.: US 12,296,088 B2
(45) Date of Patent: May 13, 2025

(54) FILTER FOR A HUMIDIFICATION SYSTEM

(71) Applicant: Fisher & Paykel Healthcare Limited, Auckland (NZ)

(72) Inventors: Eu-Lee Teh, Auckland (NZ); Bernard Tsz Lun Ip, Auckland (NZ); Larissa Grace Michelsen, Auckland (NZ); Jemma Tamsin Somerville, Auckland (NZ); James Robert Jarmey Greenfield, Auckland (NZ); Monika Baumann, Auckland (NZ); Zane Paul Gell, Auckland (NZ); Benjamin Elliot Hardinge Pegman, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 982 days.

(21) Appl. No.: 17/309,265

(22) PCT Filed: Nov. 15, 2019

(86) PCT No.: PCT/NZ2019/050150
§ 371 (c)(1),
(2) Date: May 13, 2021

(87) PCT Pub. No.: WO2020/101507
PCT Pub. Date: May 22, 2020

(65) Prior Publication Data
US 2022/0080136 A1     Mar. 17, 2022

Related U.S. Application Data

(60) Provisional application No. 62/768,793, filed on Nov. 16, 2018.

(51) Int. Cl.
*A61M 13/00*     (2006.01)
*B01D 46/00*     (2022.01)
(Continued)

(52) U.S. Cl.
CPC ....... *A61M 13/003* (2013.01); *B01D 46/0012* (2013.01); *B01D 46/0036* (2013.01);
(Continued)

(58) Field of Classification Search
CPC ............. A61M 13/003; B01D 46/0012; B01D 46/0036; B01D 2259/4533
See application file for complete search history.

(56) References Cited

U.S. PATENT DOCUMENTS 5,288,469 A   2/1994   Skalla
6,544,210 B1  4/2003   Trudel et al.
(Continued)

OTHER PUBLICATIONS

International Search Report and Written Opinion of PCT/NZ2019/050150, Dated Feb. 21, 2020, in 19 pages.

*Primary Examiner* — Robert Clemente
(74) *Attorney, Agent, or Firm* — Knobbe Martens Olson & Bear LLP

(57) ABSTRACT

Filters for surgical procedures including a fluid pathway to transport fluid, such as smoke and/or gases, exhausted from a surgical site, a humidity regulating element located along the fluid pathway, and a filter element located downstream of the humidity regulating element such that the humidity regulating element and the filter element are in fluid communication with each other. The humidity regulating element is configured to remove or reduce humidity from the smoke and/or gases exhausted from the surgical site prior to the smoke and/or gases reaching the filter element. The filter element is configured to filter particulate matter from the smoke and/or gases exhausted from the surgical site.

20 Claims, 56 Drawing Sheets

(51) Int. Cl.
  *B01D 53/14*    (2006.01)
  *B01D 53/26*    (2006.01)
(52) U.S. Cl.
  CPC ............ *B01D 53/14* (2013.01); *B01D 53/261* (2013.01); *B01D 53/265* (2013.01); *A61M 2202/0225* (2013.01); *A61M 2205/3606* (2013.01); *A61M 2205/7536* (2013.01); *A61M 2205/7545* (2013.01)

(56)  References Cited

U.S. PATENT DOCUMENTS

| | | |
|---|---|---|
| 6,685,665 B2 | 2/2004 | Booth et al. |
| 2007/0289449 A1 | 12/2007 | Roberts et al. |
| 2010/0094200 A1 | 4/2010 | Dean et al. |
| 2014/0165842 A1 | 6/2014 | Bonano et al. |
| 2017/0136195 A1 | 5/2017 | Blackhurst et al. |

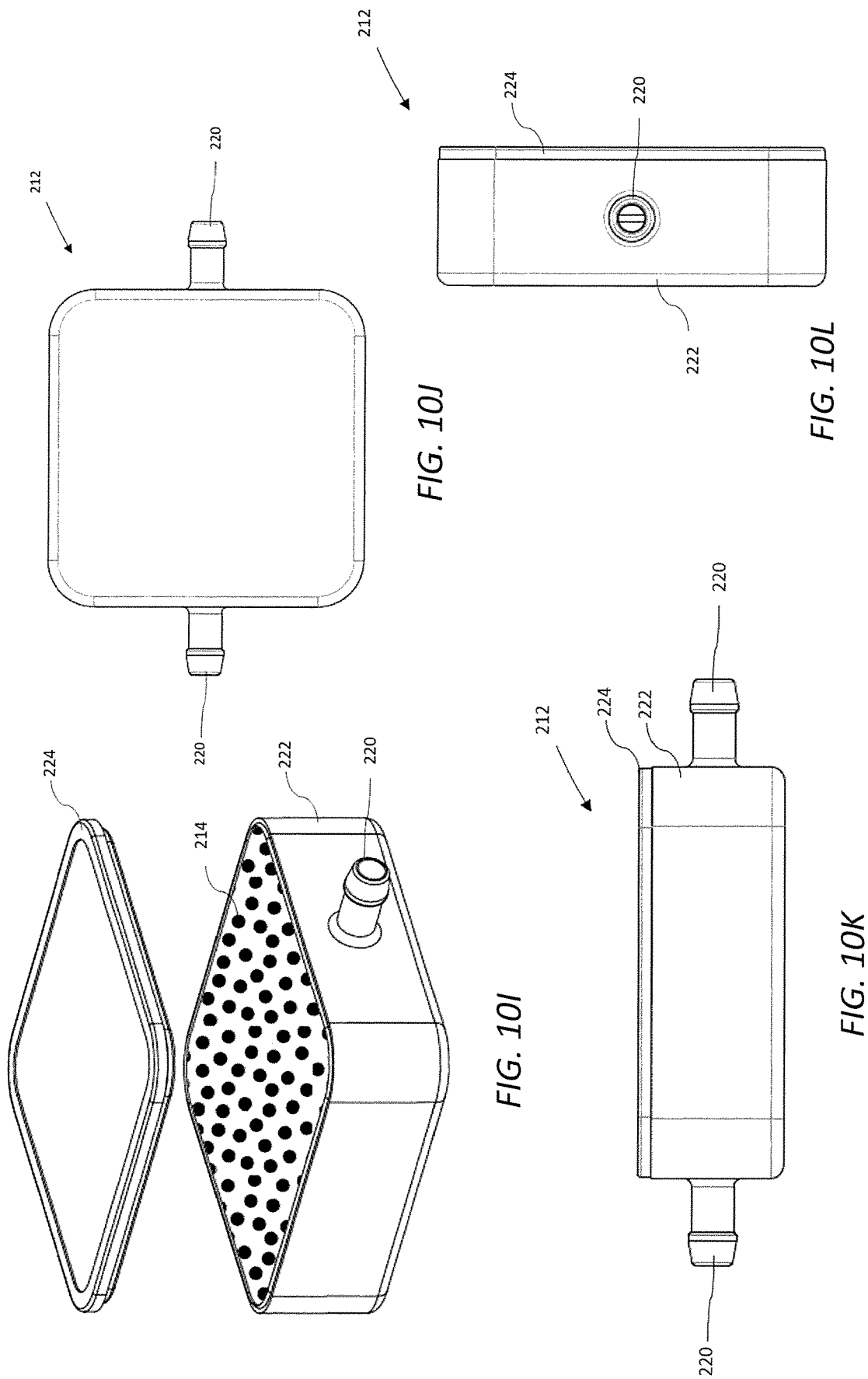

FILTER FOR A HUMIDIFICATION SYSTEM

BACKGROUND

Field

The present disclosure relates in some aspects to systems and components configured to supply fluid/gases to and/or remove fluid/gases from a patient, in particular during a medical procedure.

Description of the Related Art

Various medical procedures require the provision of gases, typically carbon dioxide, to a patient during the medical procedure. For example, two general categories of medical procedures often require providing gases to a patient. These include closed type medical procedures and open type medical procedures.

In closed type medical procedures, an insufflator is arranged to deliver gases to a body cavity of the patient to inflate the body cavity and/or to resist collapse of the body cavity during the medical procedure. The insufflator provides gases at a set pressure to establish a pneumoperitoneum. Examples of such medical procedures include laparoscopy and endoscopy, although an insufflator may be used with any other type of medical procedure as required. Endoscopic procedures enable a medical practitioner to visualize a body cavity by inserting an endoscope or the like through natural openings or small puncture(s) to generate an image of the body cavity. In laparoscopy procedures, a medical practitioner typically inserts a surgical instrument through a port (e.g., surgical cannula of a trocar) introduced through one or more natural openings, small puncture(s), or incision(s) to perform a medical procedure, e.g., a surgical procedure in the body cavity. A trocar can include a cannula and an obturator. The port provides a sealed pathway into the body cavity. In some cases, an initial endoscopic procedure may be carried out to assess the body cavity, and then a subsequent laparoscopy carried out to operate on the body cavity. Such procedures are widely used, for example, on the peritoneal cavity, or during a thoracoscopy, colonoscopy, gastroscopy or bronchoscopy.

In open type medical procedures, for example, open surgeries, gases are used to fill a surgical cavity, with excess gases spilling outward from the opening. The gases can also be used to provide a layer of gases over exposed body parts, for example, including internal body parts where there is no discernible cavity. For these procedures, rather than serving to inflate a cavity, the gases can be used to prevent infection or contamination from the environment external to the surgical site by covering exposed internal body parts with a layer of heated, humidified, sterile gases.

An apparatus for delivering gases during laparoscopic procedures can include an insufflator arranged to be connected to a remote source of pressurized gases, for example, an insufflation fluid (for example, gases) supply system in a hospital. The apparatus can be operative to control the pressure and/or flow of the gases from the gases source to a level suitable for delivery into the body cavity, usually via a cannula or needle connected to the apparatus and inserted into the body cavity, or via a diffuser arranged to diffuse gases over and into the wound or surgical cavity.

The internal body temperature of a human patient is typically around 37° C. It can be desirable to match the temperature of the gases delivered from the apparatus as closely as possible to the typical human body temperature. It can also be desirable to deliver gases above or below internal body temperature, such as, for example, 1, 2, 3, 4, 5, 6, 7, 8, 9, 10, or 15 degrees above or below internal body temperature for example, or ranges including any two of the foregoing values. It can also be desirable to deliver gases of a desired fixed or variable humidity and/or a desired fixed or variable gas temperature (which may also be referred to herein as standard), such as dry cold gas, dry hot gas, humidified cold gas, or humidified hot gas for example. Further, the gases delivered into the patient's body can be relatively dry, which can cause damage to the body cavity, including cell death, cell desiccation, or adhesions. In many cases, a humidifier is operatively coupled to the insufflator. A controller of the apparatus can energize a heater of the humidifier located in the gases flow path to deliver humidification fluid, e.g., water vapor to the insufflation fluid (for example, gases) stream prior to entering the patient's body cavity.

The humidified gas can be delivered to the patient via further tubing that may also be heated. The insufflator and humidifier can be located in separate housings that are connected together via suitable tubing and/or electrical connections, or located in a common housing arranged to be connected to a remote gas supply via suitable tubing.

SUMMARY

During laparoscopic surgery, there will generally be some form of energy delivery (e.g., electrosurgery, electrocautery, laser cutting/cautery, etc.) to cause cutting or coagulation of tissue (including other organs, anatomical structures, and/or the like) and/or blood vessels within the surgical cavity, e.g., the pneumoperitoneum for certain types of surgeries. This produces surgical smoke that can increase in concentration over time in the sealed and pressurized surgical cavity, e.g., peritoneum, especially when there are no significant gas leaks or suction/irrigation. The smoke plume accumulates and can block vision. Further the smoke plume may contact or deposit particles on the scope. The smoke plume contacting the scope can also cause fogging or condensation on the scope. Condensation can occur on various surfaces on a medical instrument. When condensation forms on a viewing surface of a medical instrument, this is observed as a fogging effect which manifests as an impairment of visibility through a lens or any other viewing surface of a medical instrument (such as, for example, a mirror or transparent or translucent window). When condensation forms on various surfaces of a medical instrument, the condensation can coalesce into water droplets. This can occur directly on the viewing surface or other surfaces which can then migrate to or be deposited on the viewing surface. Accordingly, as used herein condensation and/or fogging means condensation generally and in some instances, specifically with respect to condensation on a viewing surface (i.e. fogging). In other words, a high concentration of smoke in the pneumoperitoneum, and in the field of vision can severely impede the optical clarity when viewing the space inside the peritoneum or other site through a camera inserted through a vision system, including but not limited to a scope or a camera unit, inserted, for example, cannula of a trocar. A trocar includes a cannula and an obturator. Over an extended period of time, the high concentration of smoke in the pneumoperitoneum may contribute to other adverse health conditions. Without the use of venting or suction, surgeons generally have no option but to release some volume of gases or sometimes all the gases from inside the pneumoperitoneum through deflation, then re-insufflation, which can be inconvenient and cause undesirably increased operating room and anesthesia time. Therefore, it can be useful to vent out smoke plumes and smoke concentration.

When particulate matter (e.g., undesirable fluids including smoke and chemicals, etc.) is cleared from the pneumoperitoneum during laparoscopic surgery into the operating theatre, it can be best practice to filter the smoke particles from the gas being released so the smoke particles are not inhaled by operating theatre staff. When these particles are trapped by the filter, they can act as nucleation sites for humidity in the gas being released out of the pneumoperitoneum (this gas that has been humidified by products in the gas delivery system or by the patients' physiology). This combination of smoke particles and humidity can act to "clog" the filter, causing reduced gases flow, and negatively impacting the ability to vent smoke—this results in a reduced rate of clearance, a build of smoke and hence may worsen optical clarity during surgery.

Systems and methods herein can advantageously manage and/or reduce humidity that reaches the filter element so the filter (e.g., smoke filter) can properly filter the particulate matter such as, for example, smoke particles. Improving performance of the filter element facilitates a consistent flow throughout the filter (e.g., smoke filter), which may facilitate a substantially constant venting rate (or a constant venting rate or within a predetermined range) to atmosphere and/or maintain a substantially constant pressure in the pneumoperitoneum. In some configurations, humidity is removed from the gas-path before the gas reaches the filter so that the humidity cannot condense on the filter and interact with the smoke particles. In some configurations, moisture/humidity is condensed in the gas-path before the filter so that the humidity cannot condense on the filter and interact with the smoke particles. In some configurations, moisture/humidity passes through the filter without condensing so that it cannot interact with the smoke particles. In some configurations, the filter surface area is increased to reduce the chance of humidity and particle interactions, or reduce the density of these interactions.

In some configurations, systems and methods as disclosed herein can advantageously vent gas (and smoke plumes created during procedures, for example electrosurgery/electrocautery) from inside the pneumoperitoneum which achieves at least two advantages: it can dilute the smoke concentration inside the pneumoperitoneum to improve visibility, and it can also ensure a constant flow of fluids and/or gases, such as, for example, $CO_2$, from the insufflator which creates an airflow of "clean" $CO_2$ gas across/over the viewing area which carries or pushes away smoke that is hindering vision in the area between the camera and operating area. The venting flow rate may be related to the delivered flow rate. For example, the venting rate (e.g., venting flow rate) may be set to achieve a specified pressure within the surgical site. Explained another way, the venting rate is such that a surgical cavity is maintained at a predetermined pressure. In some embodiments, venting flow rate may be a predetermined flow rate. For example, the flow rate may be set by the user. The venting element used may be constructed or tuned to achieve the predetermined flow rate. The venting element may include an automatic or manual flow control element that allows the user to control the venting flow rate. However, there can be a trade-off when venting in terms of negatively affecting stability and pressure of the pneumoperitoneum.

In some configurations, systems and methods can advantageously filter to remove harmful chemicals and bio-particles from the gas being vented into the operation room. A growing concern in surgical environments is hazards to surgical staff (and patients) from the smoke produced during electrosurgery/electrocautery. Research indicates that surgical smoke can contribute to cancers or other health issues, and contains many chemicals and bio-particles that can be hazardous for human inhalation. Therefore, it can be advantageous in some cases to include an integrated filter (e.g., smoke filter), or capacity to have the filter as a removable attachment on the venting outlet. Any of the filters described herein may include a hydrophilic or a hygroscopic material. In some embodiments, a filter could include a particulate filter to filter particulate matter based on the pore size of the filter, such as, for example, a ULPA or a HEPA filter. Alternatively or additionally, the filter could include an activated carbon filter, a dust filter, and/or a desiccant (such as, for example, silica) to remove smoke or volatiles in the gases.

In some aspects, disclosed herein is a filter for a medical, e.g., surgical procedure including a fluid pathway (sometimes referred to herein as a gases pathway) to transport fluid, such as, for example, smoke and/or gases, exhausted from a surgical site, a humidity regulating element located along the gases pathway, and a filter element located along the gases pathway downstream of the humidity regulating element such that the humidity regulating element and the filter element are in fluid communication with each other. The gases pathway is defined by a tube or conduit. For example, the tube may be a flexible tube or alternatively may be a substantially inflexible tube. In some configurations, the gases pathway may be defined by a surgical cannula. The humidity regulating element is configured to remove or reduce smoke and/or humidity from the smoke and/or gases exhausted from the surgical site prior to the smoke and/or gases reaching the filter element. The filter element configured to filter particulate matter from the smoke and/or gases exhausted from the surgical site. As used herein, a humidity regulating element is any element configured to regulate the humidity of a media (e.g., a stream of one or more gases) by removing vapor and/or liquid moisture.

In some configurations, the humidity regulating element itself removes smoke, particulates, and/or volatiles. For example, the humidity regulating element may include a desiccant that provides a filter function. In some configurations, at least a portion of the smoke, particulates, and/or volatiles is removed by the humidity regulating element and the filter element separately filters smoke, particulates, and/or volatiles or other gases. In some configurations the filter (e.g., smoke filter) can includes a plurality of filter elements to filter out smoke and/or remove (e.g., filter) humidity and/or moisture.

In some configurations, the gases pathway extends to atmosphere through the humidity regulating element and/or filter element such that the filtered smoke and/or gases are vented to atmosphere after filtering.

In some configurations, the humidity regulating element may be in series (e.g., daisy chained) with the filter element such that the filter element is spaced from and downstream of the humidity regulating element.

In some configurations, the humidity regulating element may be nested within the filter element such that the filter element partially surrounds a portion of the humidity regulating element. The filter element may be downstream in the gases pathway.

In some configurations, the humidity regulating element includes a desiccant to remove humidity. The desiccant may include a plurality of granules of desiccant material.

In some configurations, a desiccant may be positioned within the gases pathway such that smoke/gases exhausted from the surgical site pass through the desiccant.

In some configurations, the humidity regulating element includes a housing separate from and upstream to the filter element. The housing containing a desiccant therein and defining a gases pathway to allow smoke/gases exhausted from the surgical site to pass through the housing.

In some configurations, the housing includes a tube with the desiccant located within the tube.

In some configurations, the filter element may be a separate housing including one or more filter media within the housing.

In some configurations, the filter element includes one or more filter media including an activated carbon filter media and a particulate filter media, such as, for example, a ULPA filter or a HEPA filter. In some configurations, the desiccant filters smoke or particulate matter, such that the desiccant functions as a filter.

In some configurations, the humidity regulating element and the filter element are located in two separate compartments of a housing. The humidity regulating element may be positioned upstream of the filter element.

In some configurations, the humidity regulating element includes a tube with a desiccant therein. The filter element may be a cuff that surrounds a portion of the tube and filters the gases along a portion of the tube. The tube may be a breathable/permeable tube that allows gases and/or liquid to permeate through the tube.

In some configurations, the humidity regulating element includes a wicking or hydrophilic material positioned within the gases pathway and upstream of the filter element. Although certain embodiments are described herein with respect to a wicking or hydrophilic material, the humidity regulating element may also include a hygroscopic material, for example a desiccant material such as, for example, silica.

In some configurations, the wicking or hydrophilic material may be formed as a ring or toroidal element disposed within the gases pathway upstream of the filter element.

In some configurations, the wicking or hydrophilic material may be located within a housing containing the filter element, upstream of the filter element.

In some configurations, the wicking or hydrophilic material may be located within a transport tube and extends the length of the gases transport tube. The gases transport tube defining the gases pathway.

In some configurations, the wicking or hydrophilic material may be positioned in a lumen defined by the transport tube and arranged substantially within a center of the transport tube.

In some configurations, the wicking or hydrophilic material may be located on an inner wall of the transport tube the wicking or hydrophilic material defining the gases pathway therein to allow gases to travel through it.

In some configurations, the humidity regulating element includes a cooling structure located within the gases pathway. The cooling structure causing moisture/humidity to condense.

In some configurations, the humidity regulating element includes a fluid, e.g., water trap to collect condensed water/liquid.

In some configurations, the filter (e.g., smoke filter) includes a case. The case including a filter compartment including the filter element and a fluid, e.g., water trap compartment. The case being downstream of the cooling structure, and the filter compartment being downstream of the water trap compartment.

In some configurations, the fluid, e.g., water trap compartment includes a narrow opening and a recess that defines a larger volume than the narrow opening.

In some configurations, the case includes an inlet having one or more protrusions defining a trap that prevents condensed humidification fluid, e.g., water flowing into the filter compartment.

In some configurations, the gases pathway includes a coaxial tube/nested tube arrangement including a first tube and a second tube, the first tube positioned inside the second tube, the first tube comprising a permeable membrane wherein the first tube configured to receive and store condensed fluid, e.g., water/liquid.

In some configurations, the cooling structure includes an active cooling structure.

In some configurations, the active cooling structure may be a Peltier cooler, a heat sink, or an insulated region.

In some configurations, the humidity regulating element may include a permeable tube that is configured to allow vapor and/or liquid moisture to escape the gases pathway prior to the gases entering the filter.

In some configurations, the humidity regulating element includes a condensing element configured to cause condensation of the moisture/humidity within the exhausted smoke and/or gases.

In some configurations, the condensing element may be a pressure device configured to change the pressure of the smoke/gases exhausted to cause condensation.

In some configurations, the condensing element may be a fan or impeller or a sound wave generator.

In some configurations, the filter element may be coated with a hydrophobic element.

In some configurations, the humidity regulating element includes a heatsink sleeve or a cooling sleeve at least partially or fully wrapped around the gases transport pathway upstream of the filter element.

In some configurations, the humidity regulating element may include a Peltier cooling sleeve.

In some configurations, the cooling sleeve includes a refrigerant that is circulated within the sleeve about the gases transport pathway.

In some configurations, the heatsink sleeve includes a heater element disposed within or on the sleeve.

In some configurations, the gases transport pathway may be defined within a surgical cannula associated, in use, with the surgical site.

In some configurations, the humidity regulating element may be disposed within the surgical cannula.

In some configurations, the humidity regulating element may be disposed within the cannula.

In some configurations, the filter element may be positioned outside the cannula and connected to the cannula.

In some aspects, disclosed herein is a filter (e.g., a smoke filter) for a medical, e.g., surgical procedure including a fluid pathway (sometimes referred to herein as a gases transport pathway) extending from a surgical site. The gases transport pathway defining a lumen to transport fluid, such as, for example, gases/smoke, from the surgical site. The filter also includes a filter element located at an end of the gases transport pathway distal to the surgical site. The gases transport pathway is configured to prevent condensation within the gases transport pathway. The filter element includes filter media to filter at least particulate matter from smoke/gases prior to venting to atmosphere.

In some configurations, the gases transport pathway comprises a permeable/breathable tube.

In some configurations, the gases transport pathway comprises a heater element within the gases transport pathway.

In some configurations, the heater element may be a spirally wound heater within tube.

In some configurations, the heater element may be embedded in the tube wall.

In some configurations, the heater element may be within the lumen of the gases transport pathway.

In some configurations, the gases transport pathway includes a coaxial tube. An inner tube can include a permeable wall to allow vapor and/or liquid moisture to permeate to an outer lumen.

In some configurations, the outer lumen includes a desiccant.

In some configurations, the outer lumen includes a hydrophobic wall.

In some aspects, disclosed herein is a filter (e.g., smoke filter) for filtering particulate matter (e.g., exhausted smoke) from a surgical site including a tube extending from the surgical site, a moisture removal compartment comprising desiccant, a filter compartment comprising a filter media to filter particulate matter from the smoke; and a fluid (e.g., gases) pathway being defined through the tube, moisture removal compartment and filter compartment. The moisture removal compartment may be located upstream of the filter compartment. The gases pathway venting to atmosphere such that the filtered smoke is vented to atmosphere.

In some configurations, the desiccant includes granular desiccant housed within the moisture removal compartment.

In some configurations, the moisture removal compartment and the filter compartment are in series (e.g., daisy chained).

In some configurations, the filter compartment may be nested within the moisture removal compartment.

In some configurations, the moisture removal compartment defines a tortuous pathway from an inlet of the moisture removal compartment to an outlet of the moisture removal compartment.

In some configurations, the outlet of the moisture removal compartment may be in fluid communication with the inlet of the filter compartment.

In some aspects, disclosed herein is a filter (e.g., a smoke filter) for filtering particulate matter (e.g., exhausted smoke) from a surgical site including a fluid pathway to transport fluid, such as, for example, smoke and/or gases, exhausted from a surgical site and a filter element positioned within the gases pathway. The gases pathway includes an orifice. The orifice being shaped and structured to define a predefined leak rate from the surgical site such that smoke is cleared from the surgical site.

In some configurations, the smoke may be cleared at the predefined leak rate.

In some configurations, the orifice may be defined in a connector that couples to a venting device associated with the surgical site. The connector may be positioned at one end of the gases pathway.

In some configurations, the filter element may be located at an end of the gases pathway that is distal/opposed to the connector end.

In some configurations, the predefined leak rate is at least about 1.5 L/min and/or less than or equal to about 8.5 L/min, for example at least about 2 L/min and/or less than or equal to about 5 L/min.

In some configurations, the orifice may be defined at an outlet of the filter element.

In some configurations, the orifice may include a diameter of at least about 1.5 mm and/or less than or equal to about 6 mm, for example at least about 2 mm and/or less than or equal to about 3 mm.

In some configurations, the pressure in the pneumoperitoneum is between 11 mmHg to 15 mmHg when the filter is in use.

In some aspects, disclosed herein is a filter for a medical, e.g., surgical procedure including a humidity regulating element and a filter element. The humidity regulating element is configured to regulate humidity from gases exhausted from a surgical site. The humidity regulating element may include a desiccant material. The filter element is located downstream of the humidity regulating element such that the gases flow through the humidity regulating element prior to flowing through the filter element. The filter element is configured to filter particulate matter from the gases exhausted from the surgical site.

In some configurations, the humidity regulating element includes a housing and the filter element includes a separate housing downstream from the humidity regulating element.

In some configurations, the humidity regulating element and the filter element are nested within a single housing.

In some aspects, disclosed herein is a filter for a medical, e.g., surgical procedure including a humidity regulating element, a filter element, and a vent. The humidity regulating element is configured to regulate humidity from gases exhausted from a surgical site. The filter element is located downstream of the humidity regulating element such that the gases flow through the humidity regulating element prior to flowing through the filter element. The filter element is configured to filter particulate matter from the gases exhausted from the surgical site. The vent is configured to vent the filtered gases to atmosphere at a substantially constant venting rate (or a constant venting rate or within a predetermined range).

In some configurations, the vent is an active venting device or a passive venting device.

In some configurations, the humidity regulating element includes a desiccant material.

In some configurations, the humidity regulating element includes a housing and the filter element includes a separate housing downstream from the humidity regulating element.

In some configurations, the humidity regulating element and the filter element are nested within a single housing.

In some aspects, disclosed herein is a filter for a medical, e.g., surgical procedure including a humidity regulating element, a filter element, and a vent. The humidity regulating element is configured to regulate humidity from gases exhausted from a surgical site. The filter element is located downstream of the humidity regulating element such that the gases flow through the humidity regulating element prior to flowing through the filter element. The filter element is configured to filter particulate matter from the gases exhausted from the surgical site. The vent is configured to vent the filtered gases such that a substantially constant pressure is maintained within a pneumoperitoneum.

In some configurations, the vent is an active venting device or a passive venting device.

In some configurations, the humidity regulating element includes a desiccant material.

In some configurations, the humidity regulating element includes a housing and the filter element includes a separate housing downstream from the humidity regulating element.

In some configurations, the humidity regulating element and the filter element are nested within a single housing.

In some aspects, disclosed herein is filter for a medical, e.g., surgical procedure including a humidity regulating element, a filter element, and one or more tubes. The humidity regulating element is configured to regulate humidity from gases exhausted from a surgical site. The filter element is located downstream of the humidity regulating element such that the gases flow through the humidity regulating element prior to flowing through the filter element. The filter element is configured to filter particulate matter from the gases exhausted from the surgical site. The humidity regulating element and/or the filter element may include a connector, such as, for example, a low flow resistance connector, configured to join a tube. The tubing has a low resistance to flow to facilitate continuous flow and ensure that gases from the surgical cavity can be exhausted with a lower pressure. The low resistance tubing helps to regulate the pressure in the surgical cavity

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure. In some cases, a "slice" has been shown for clarity purposes for some sectional and cross-sectional views of a three-dimensional cannula. A person reasonably skilled in the art would be able to appreciate from the disclosure herein that these figures illustrate a slice of a three-dimensional cannula. Certain features may not be shown in the slices, for example, any projected surfaces including but not limited to hole surface projections. A person reasonably skilled in the art would be able to appreciate from the disclosure herein that the three-dimensional cannula with such slices can include those features.

FIGS. 10I-10L illustrate an example housing for holding the desiccant based humidity regulating element.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Example Medical Gases Delivery Systems

Gases can be introduced to a surgical cavity, such as, for example, the peritoneal cavity via a cannula inserted through an incision made in patient's body (such as, for example, the abdominal wall). The cannula can be coupled to an insufflator. A tube can be used to fluidly couple the cannula to the insufflator. The gases flow from the insufflator can be increased to inflate the surgical cavity (such as to maintain a pneumoperitoneum, which is a cavity filled with gas within the abdomen). The introduced gases can inflate the surgical cavity to provide space for the surgeons to work and perform medical procedures. A medical instrument can be inserted through the cannula into the inflated surgical cavity. For example, an endoscope or laparoscope can be inserted into the cavity and visibility in the cavity can be assisted by insertion of fluid or gases, such as, for example, air or carbon dioxide. After initial insufflation and insertion of the instrument (such as a laparoscope) through the primary cannula, additional cannulas can be placed in the surgical cavity under laparoscopic observation. The additional cannulas can be used to introduce other instruments into the surgical cavity. At the end of the operating procedure, all instruments and cannulas are removed from the surgical cavity, the gases are expelled, and each incision is closed. For thoracoscopy, colonoscopy, sigmoidoscopy, gastroscopy, bronchoscopy, and/or others, the same or substantially similar procedure for introducing gases to a surgical cavity can be followed. The quantity and flow of gases can be controlled by the clinician performing the examination and/or automatically by the surgical, e.g., insufflation system. The insufflator may deliver intermittent and/or constant flow. Intermittent flow includes one, two, or more periods where flow stops (e.g., goes to zero L/min) before restarting. Constant flow includes flow consistently above zero L/min, although the actual flow rate may vary. The insufflator can control flow to ensure that the pressure in the surgical cavity is maintained at or around a predetermined range. The pressure allows the pneumo cavity to be inflated to a predetermined amount.

Figure 1:
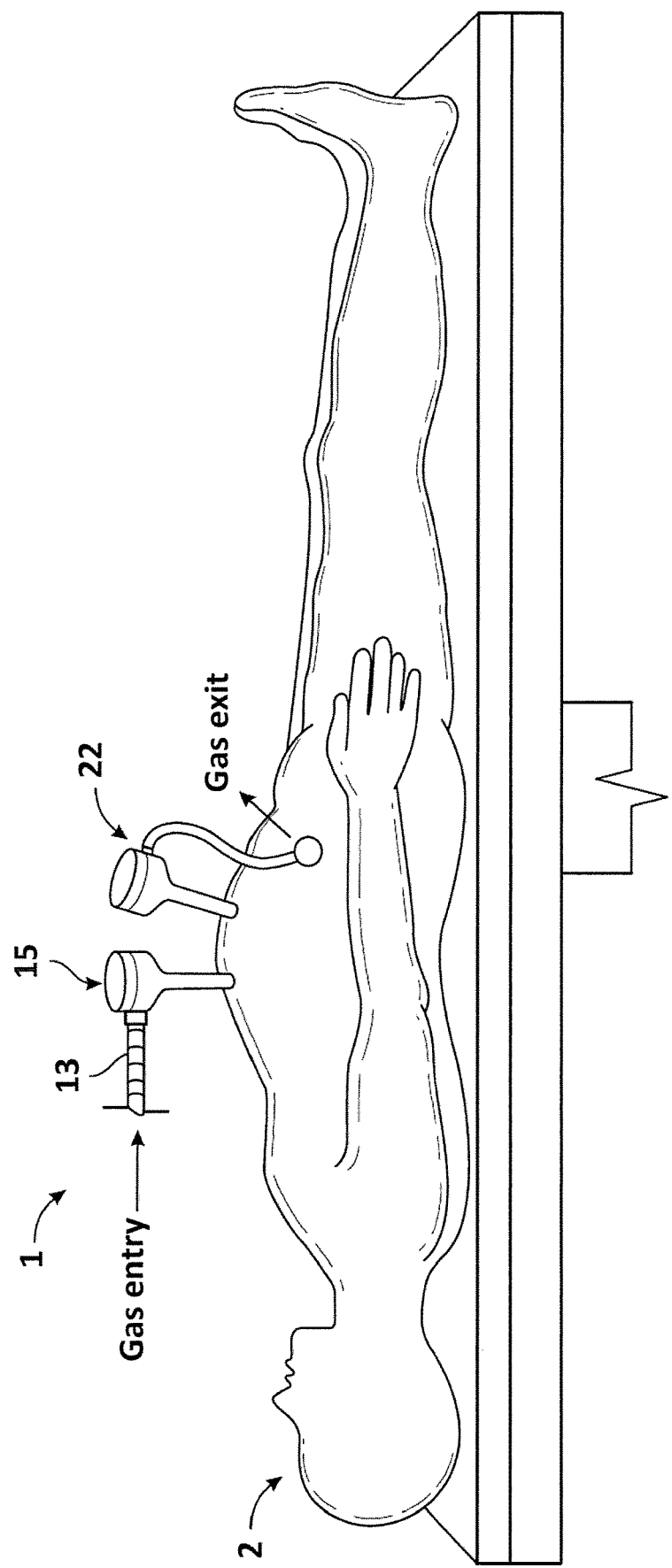
FIGS. 1-3C illustrate schematically different example surgical, e.g., insufflation systems during a medical procedure.

FIGS. 1 to 3 schematically different examples of a surgical, e.g., insufflation system 1 during a medical procedure. Features of FIGS. 1 to 3 can be incorporated into each other. The same features have the same reference numerals in FIGS. 1 to 3. The cannula can be single use (disposable) or reusable. Alternatively, parts of the cannula can be single use (disposable) or reusable. The cannula may be made of materials that are biocompatible and/or sterilizable.

As shown in FIG. 1, the patient 2 can have a cannula 15 inserted within a cavity of the patient 2, for example an abdomen of the patient 2 in the case of a laparoscopic surgery. The cannula 15 is connected to a gases delivery conduit 13, for example via a Luer lock connector. The cannula 15 delivers gases into a surgical site, such as, for example, within the cavity of the patient 2. The cannula 15 may include one or more passages to introduce gases and/or one or more medical, e.g., surgical instruments into the surgical cavity. The medical, e.g., surgical instrument can be a scope, electrocautery tool, or any other suitable instrument.

The system can also optionally include a venting device such as a venting tube or venting cannula 22, which may have substantially the same features as the cannula 15. The venting cannula 22 may include a valve, such as a stop cock, that manually or automatically allows venting. For example, a stop cock may be actuated to open a fluid path out of the cavity through the venting cannula 22. The valve may be automatically controlled by a controller associated with the gases source (e.g., insufflator) or by a controller in the humidifier. Additionally or alternatively, the valve may also be manually actuated, for example by turning a tap by hand or by a foot pedal, or otherwise. The venting cannula 22 may be coupled to a filtration system to filter out smoke and the like. The venting cannula 22 may alternatively be coupled to a system that is configured to recycle or recirculate the gases from the surgical cavity back to the insufflator for re-delivery into the surgical cavity. The gases may be filtered and/or dehumidified prior to being returned to the insufflator. The venting cannula 22 may optionally be coupled to an active smoke evacuation apparatus e.g. a vacuum or pump that draws out smoke and other gases from the surgical cavity.

Figure 2A:
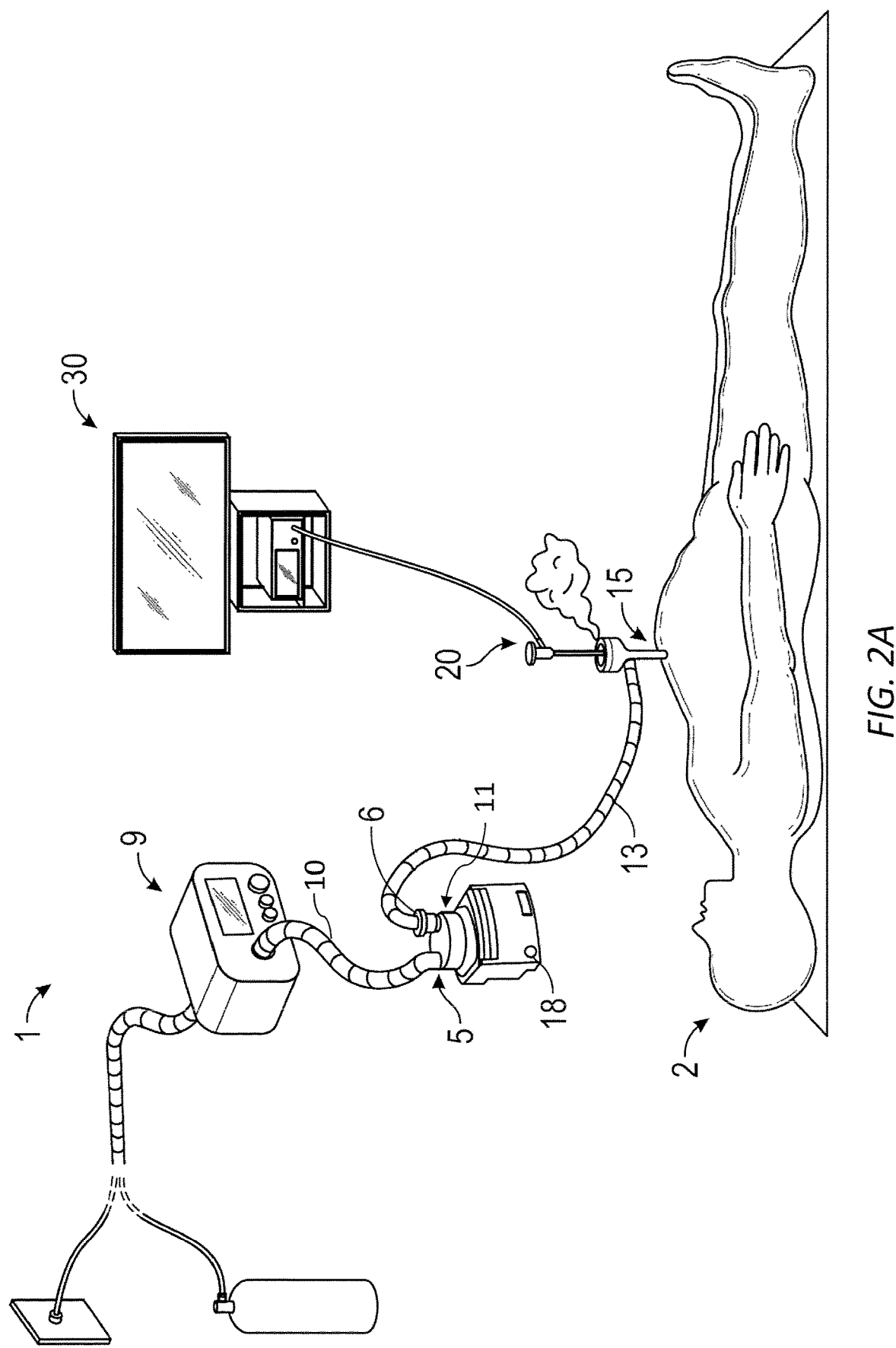

As shown in FIG. 2A, the instrument cannula 15 may also be a venting cannula, heated cannula, directed gas flow cannula, and/or wicking cannula. For example, a filter may be internal to the cannula 15. Maintaining a consistent flow out of the cavity can help to maintain a continuous flow into the cavity. This can improve smoke clearance and optical clarity. The continuous flow into the cavity can also help to contribute to reducing fogging and/or clearing fog built up on the scope. As shown in FIG. 2A, the cannula 15 may include structures or features that grip an instrument 20, such as a scope, in a substantially concentric and/or coaxial arrangement in the cannula 15, relative to the cannula shaft causing insufflation fluid, e.g., gases to surround the instrument 20 in the cannula 15 and extend beyond the end of the instrument 20 to define a protection zone due to the flow of the gases following the profile of the instrument 20. The protection zone is formed of heated humidified gases delivered through the cannula 15. If the instrument 20 is a scope, the protection zone prevents particles from contacting the scope lens and helps in maintaining the temperature around the scope to prevent fogging and/or clear fog that has occurred. Continuous venting flow assists in maintaining a continuous flow into the cavity through the cannula 15, which assists in preventing fogging on the scope.

The cannula that retains the instrument 20 in a concentric and/or coaxial arrangement may also include one or more wicking elements disposed on or within the cannula shaft to wick away any fluid, including a humidification fluid, for example, liquid water or excess moisture that may condense into the cannula. The wicking elements may extend along a portion of the shaft of the cannula or may be located in the top region adjacent the entry or adjacent the seals. The cannula 15 may include a combined delivery passage defined by the shaft and may also include a venting passage. The venting passage may be integrally formed into the cannula, e.g., a dual passage cannula or may be a separate piece that is attached to the cannula e.g. by adhesive, overmoulding, ties, clips or clamps. The filter is associated with the venting passage.

Figure 2B:
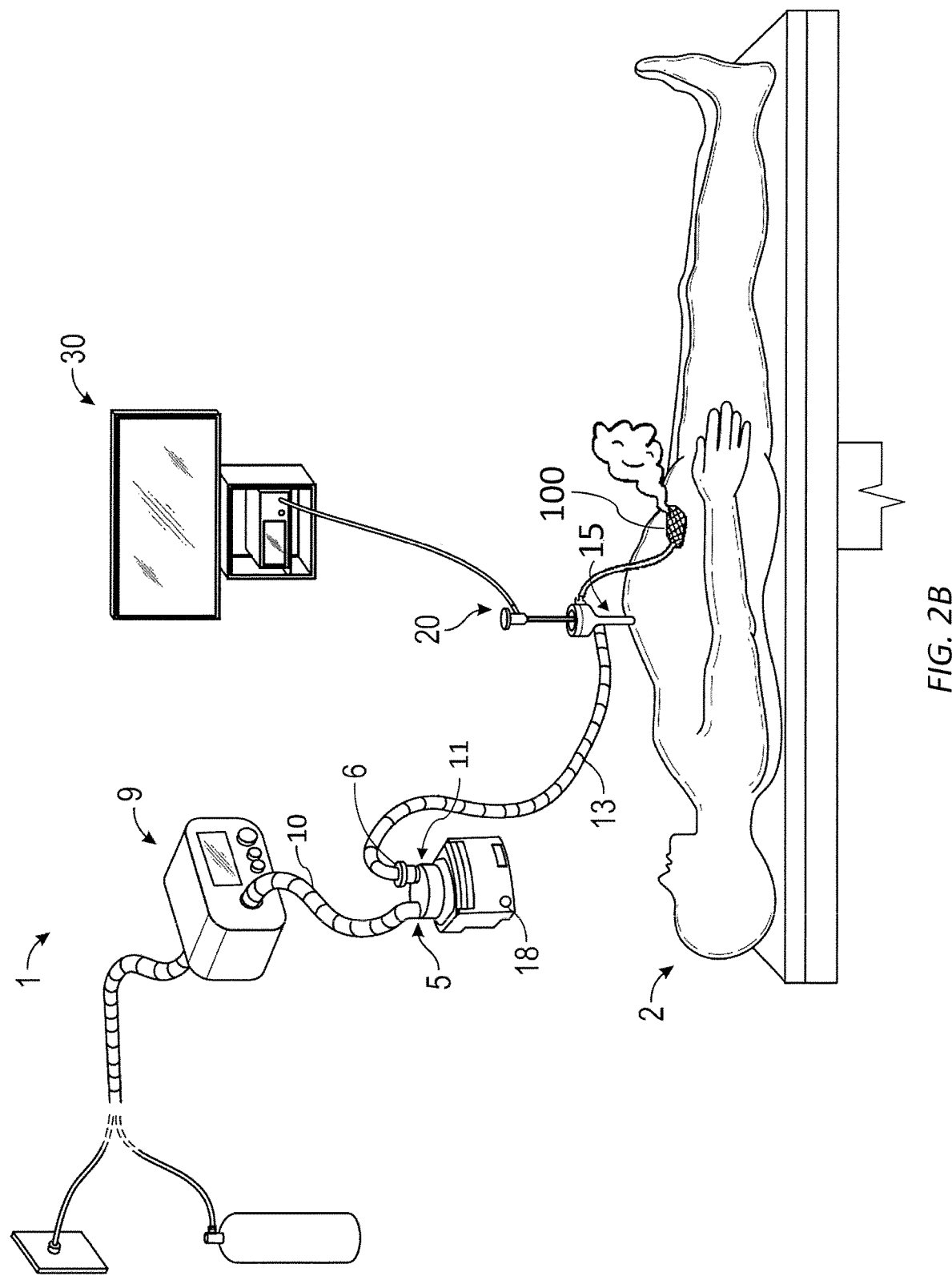
Figure 2C:
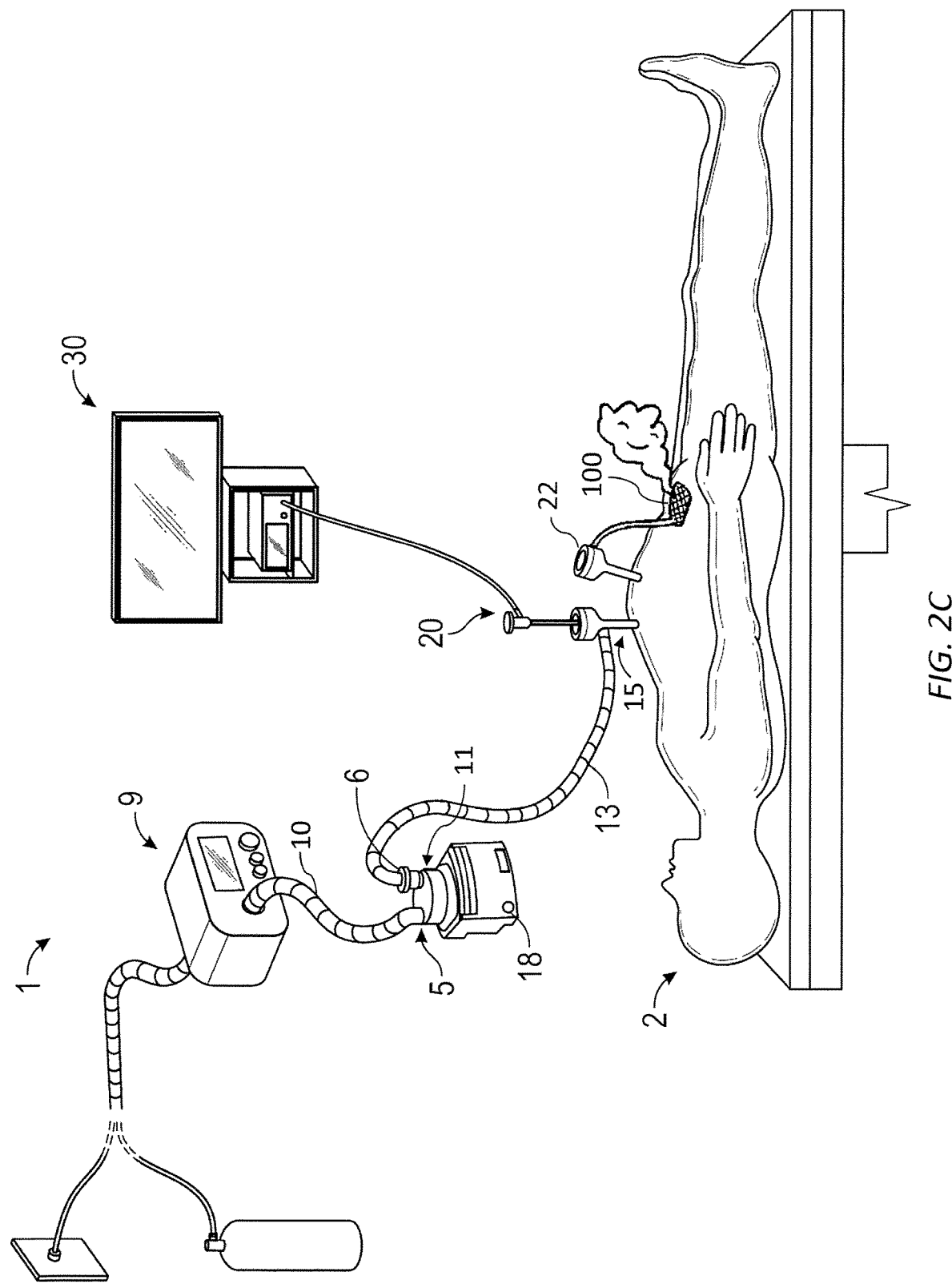
Figure 2D:
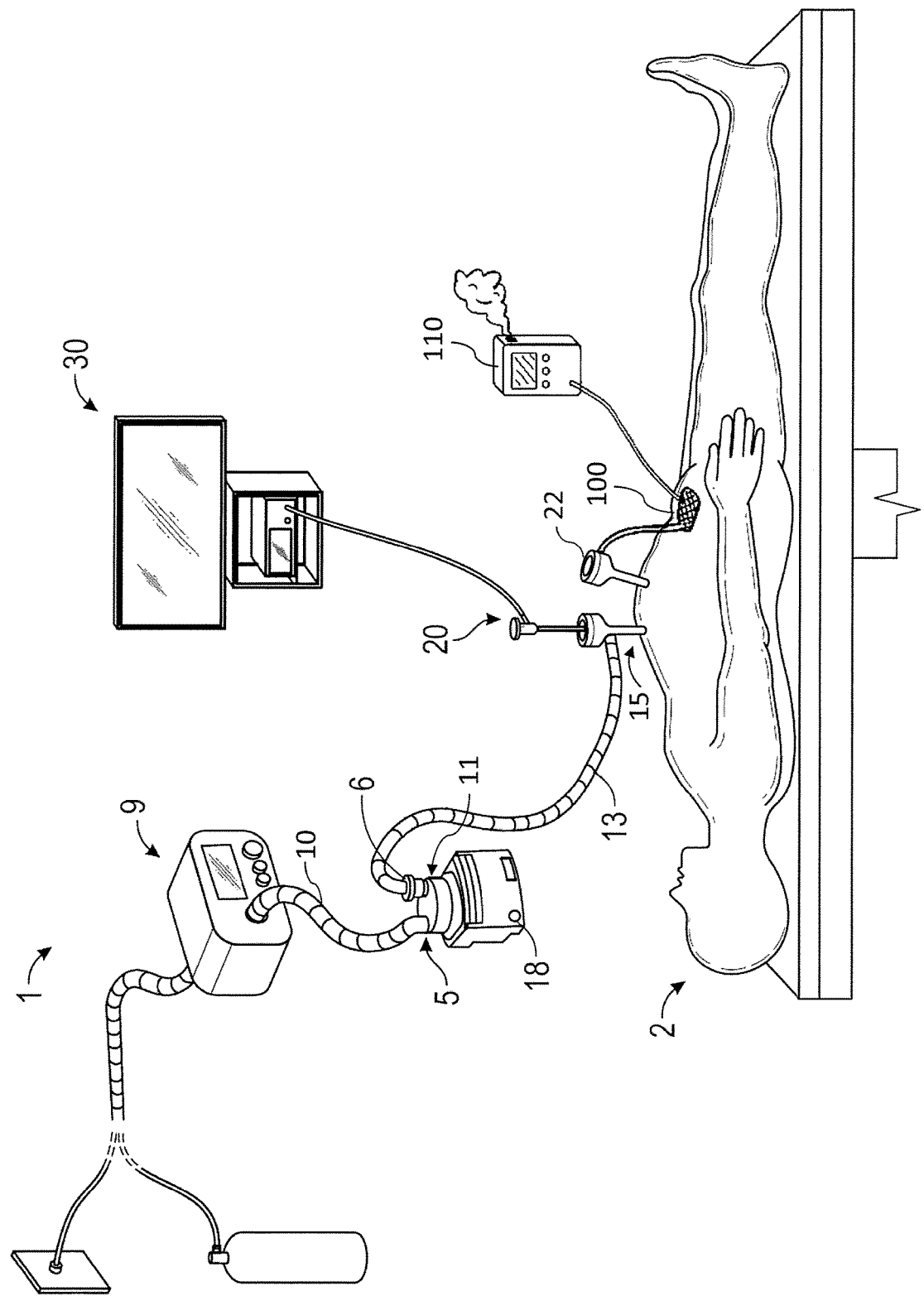
Figure 2E:
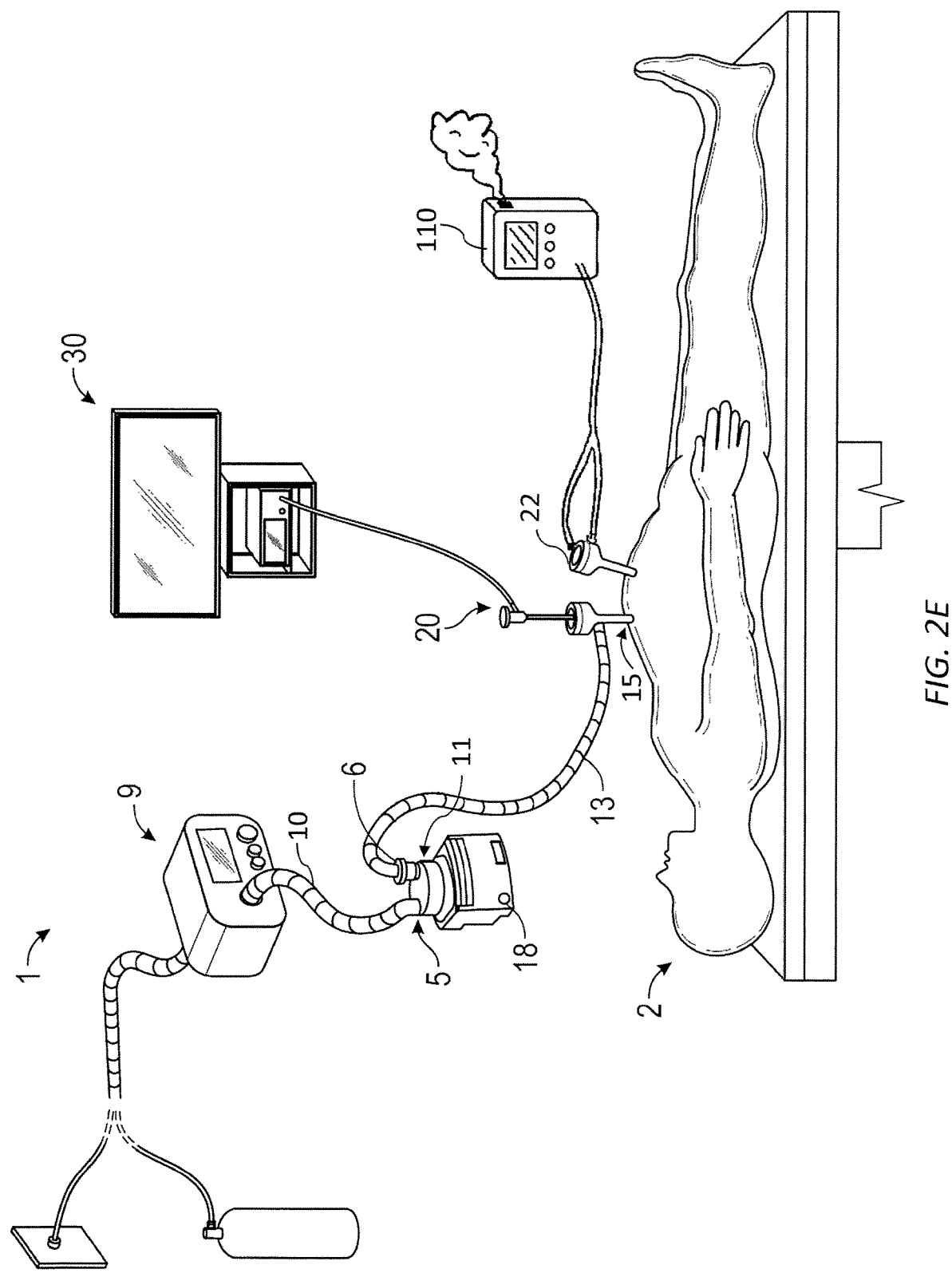

In FIG. 2B, the filter 100 (e.g., a smoke filter) is external to the cannula 15, for example the filter 100 may be attached to the cannula 15 using a Luer connector or other connector. Although, as described below, at least a portion of the filter 100, for example the humidity regulating element 104, may be disposed within the cannula 15 (see for example FIGS. 4 and 5). FIG. 2C shows the use of an instrument cannula 15 and a separate venting cannula 22 having a filter 100 attached to the venting cannula 22. Again, at least a portion of the filter 100, for example the humidity regulating element 104, may be disposed within the cannula 15. Any of the embodiments described herein may include a venting device 110. FIG. 2D illustrates a venting device 110 extending from a filter 100, and FIG. 2E illustrates the venting device 110 extending from the cannula 15. In FIG. 2E, the venting device 110 may be connected to the cannula 15 by one or more tubes or connections. For example, the venting device 110 may be connected to the cannula 15 by a Luer connection or other connector on the cannula 15 or directly into the cannula 15. The venting device 110 allows filtered smoke, vapor, or other gases to leak to atmosphere. The venting device 110 may be a passive venting device or an active venting device, for example including or capable of being connected to a vacuum or pump, as described herein. The venting device 110 may provide a feedback mechanism to control the leak rate.

In any of the configurations shown in FIGS. 2A-2E, the surgical instrument 20 introduced into the instrument cannula 15 may be coupled to an imaging device 30, which may have a screen. The imaging device 30 may be part of a surgical system, e.g., surgical stack, which may include a plurality of surgical tools and/or apparatuses. The gases delivery conduit 13 may be made of a flexible plastic and may be connected to a humidifier 5. The humidifier 5 may optionally be in serial connection to a gases supply 9 via a further conduit 10. A filter 6 may be connected downstream of the humidifier's outlet 11. The filter 6 may also be located along the further conduit 10 or at an inlet of the cannula 15. The filter 6 is configured to filter out pathogens and particulate matter in order to reduce infection or contamination of the surgical site from the humidifier or gases source.

The gases supply 9 may provide one or more insufflation gases, such as carbon dioxide or other suitable gases, to the humidifier 5. The gases supply 9 may provide a constant or intermittent flow of gases. The further conduit 10 may also be made of a flexible material such as, for example, plastic. The gases are humidified as they are passed through the humidifier 5, which can contain a volume of water. The water is heated in the humidifier to create water vapour that is mixed with the insufflation gases as the insufflation gases pass through the humidifier. The insufflation gases are also warmed as they pass through the humidifier to a predetermined temperature.

The gases may exit through the humidifier's outlet 11 and into the gases delivery conduit 13. The gases may move through the gases delivery conduit 13 into the surgical cavity of the patient 2 via the cannula 15, thereby inflating and maintaining the pressure within the cavity. Preferably, the gases leaving the outlet 11 of the humidifier 5 have a relative humidity of, for example, up to around 100%, for example, at 100%. As the gases travel along the gases delivery conduit 13, further condensation can occur so that humidification fluid vapor (e.g., water vapor) can condense on a wall of the gases delivery conduit 13. Further condensation can have undesirable effects, for example, detrimentally reducing the humidification fluid, e.g., water content of the gases delivered to the patient. In order to reduce and/or minimize or prevent the occurrence of condensation within the gases delivery conduit 13, a heating element, such as, for example, a heater wire may be provided within, throughout, or around the gases delivery conduit 13. The heater wire may be electronically connected to the humidifier, for example by an electrical cable to power the heater wire. In some embodiments, other heating elements could be included in addition or alternatively, e.g., a conductive ink, conductive polymers, or a flexible PCB. In some embodiments, other heating elements could be included in addition or alternatively. In some cases, the PCB could be flexible, or rigid and pre-shaped to an arcuate shape for example. In some embodiments, the heating element could be, for example, discrete Positive Temperature Coefficient ("PTC") heaters, or heaters including conductive plastic/polymer. Optionally, the heating element can include an inductive heating element. Optionally, the heating element can include a chemical heating element, for example, silica beads. Optionally, the cannula can be pre-heated prior to insertion.

A patient input 18 located on the humidifier 5 may allow a user (such as a surgeon or nurse) to set a desired gases temperature and/or gases humidity level to be delivered. Other functions can also optionally be controlled by the user input 18, such as control of the heating delivered by the heater wire. A controller can control the system 1, and in particular to control the flow rate, temperature, and/or humidity of gas delivered to the patient, to be appropriate for the type of medical procedure for which the system 1 is being used. The humidifier 5 may also include a display for displaying to the user the characteristics of the gas flow being delivered to the patient 2.

In some instances, during medical, e.g., surgical procedures, medicament may be introduced into the surgical cavity. The medicament may be nebulized or aerosolized by a nebulizer or aerosolizer, respectively. The medicament may be introduced through one of the surgical cannulas 15, 22 or may be introduced at the humidifier 5 (either upstream or downstream). Although filters described herein may be described as smoke filters or filters for filtering smoke, any of the filters described herein may be configured to filter out and/or trap other particulate matter such as the medicament, chemicals or other substances. The medicament may be collected in a container or receptacle within the filter apparatus such that it can be re-used. Alternatively, the medicament may be recycled or recirculated back into the surgical cavity.

In the illustrated configuration, the humidifier 5 is a separate device that is operatively coupled to the insufflator. Alternatively, the humidifier may be integrated into the insufflator such that the insufflator is a combination gases supply and humidifier. Such a combination device may include separate controllers or may include a single controller that controls the insufflator and the humidifier.

When in use, the humidifiers described above can be located outside an "operating sterile zone", adjacent, and/or integrated within the insufflator. As a result, the medical personnel would not be required to touch the humidifier when moving the cannula during the operation to maneuver the medical instruments within the surgical cavity. The humidifier may not need to be sterilized to the same extent as the medical instruments. Furthermore, the humidifier being located outside the "operating sterile zone" can reduce obstructions to the medical personnel during the operating procedure that may restrict movements of the medical personnel and/or the medical instruments in the already crowded space.

Figure 3A:
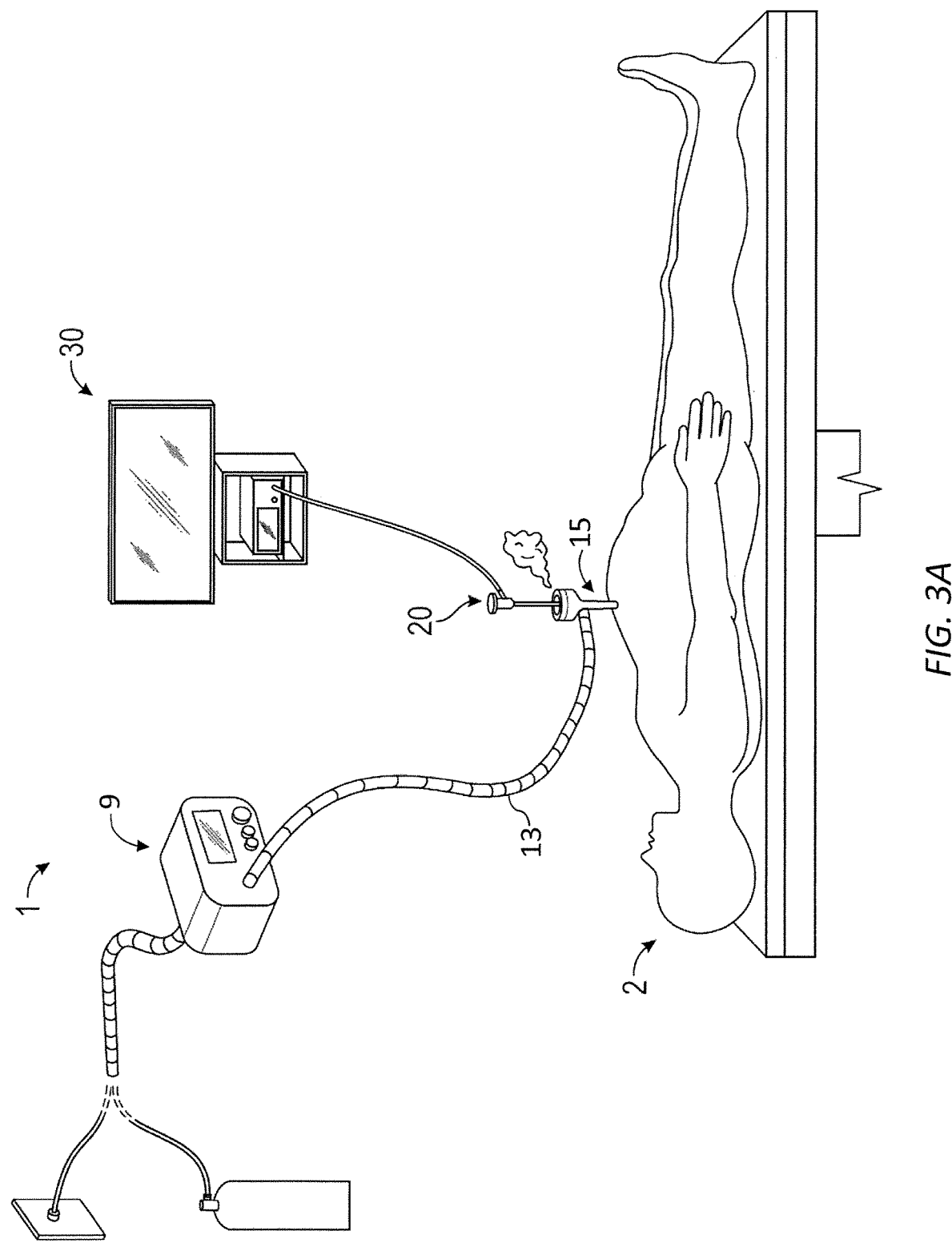
Figure 3B:
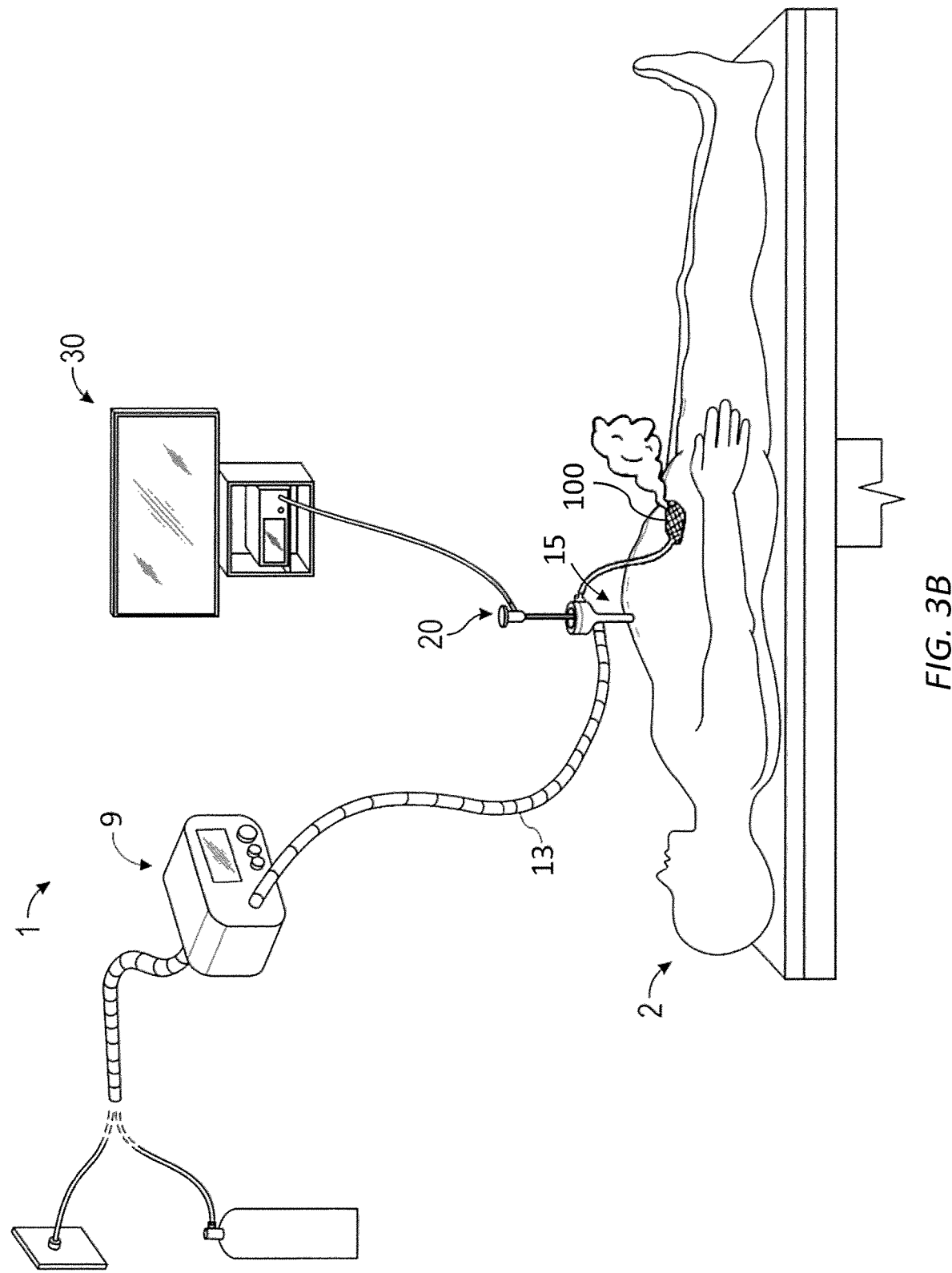
Figure 3C:
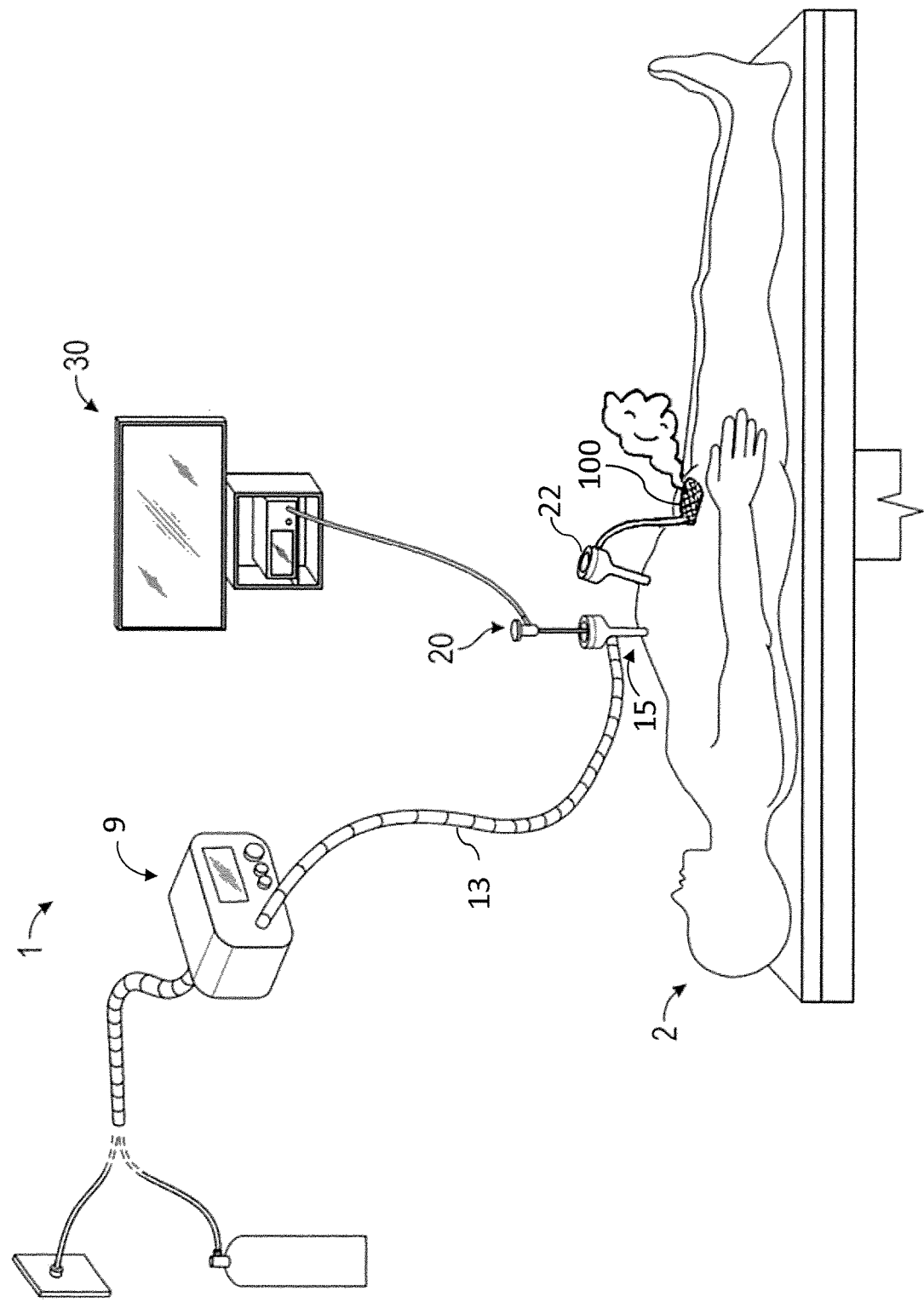

As shown in FIGS. 3A-3C, the cannula 15 and/or venting cannula 22 may also be used in a medical procedure without the humidifier. The gases supply 9 or gases source may be an insufflator, bottled gases, or a wall gases source. The gases supply 9 may provide the gases without humidification and/or heating.

Examples of Smoke Venting Filters

Any of the systems and methods described in FIGS. 4-42 may be implemented as a smoke venting filter attachment connected to a cannula, a retrofit/adaptor to an existing smoke venting filter design, or integrated into the cannula itself. Although the filters described herein may be discussed as smoke filters, and/or with respect to filtering particulate matter from smoke exhausted from the surgical site, the filters may additionally or alternatively filter out aerosols, such as aerosolized medicaments, and/or medicament vapor in the surgical site. The filters may also include structures and/or materials that filter out poisonous or harmful gases prior to venting to atmosphere. There may be a container or receptacle to collect the filtered medicament or other aerosol or gases. Alternatively, there may be at least some recycling and/or recirculation of the filtered medicament or other aerosol or gases.

The filters described herein may define a predetermined leak or venting rate to maintain a stable pneumo pressure. The leak rate is configured to balance the need to clear surgical smoke and the need to maintain substantial stability of the surgical cavity. The venting rate may be greater than or equal to the delivery flow rate. A venting rate greater than or equal to a gases delivery flow rate may prevent the surgical cavity from over-inflating or over-pressuring and/or causing damage. In some configurations, the venting rate does not exceed the capability of the insufflator to deliver gases at a given delivery flow rate. The smoke filter may include structures that control the venting rate such that the venting rate is less than or equal to the delivery flow rate. A venting rate equal to or less than the gases delivery flow rate may assist in maintaining a more stable pressure in the surgical cavity. Preferably, the venting rate is equal to the gases delivery flow rate to maintain a more stable surgical cavity. The venting rate is configured such that it does not negatively affect the surgical cavity stability. In a configuration where the venting flow rate is greater than the gases delivery flow rate, the venting flow rate is limited such that it does not deflate the surgical cavity. The venting flow rate and/or stability of pressure in the surgical cavity is based at least in part on the capacity of the insufflator to provide gases delivery flow at an appropriate rate.

The smoke filter includes a connector, e.g., a Luer connector, that has a bore that is equal to or larger than the outlet of the venting cannula. The bore reduces resistance to flow, and allows a predetermined flow of gases to be vented. Further, the rest of the filter apparatus components, e.g., the filter element and tube also define a gases pathway with reduced flow restrictions of reduced resistance to flow. The shape and dimensions of the filter are such that the predetermined leak rate is maintained (subject to the pressure within the cavity and the flow rate delivered by the insufflator).

The venting rate may be controlled by an active venting device or be a passive venting rate. For example, the smoke filter may include one or more valves to control the venting rate, e.g., the rate of gases being vented out of the cannula. The one or more valves may be passive or active.

Passive venting occurs due to a pressure gradient from the cavity out to atmosphere. Generally, there may be no vacuum or pump. Gases travel through a passive venting device due to this pressure gradient. Gases flow due to the natural pressure gradient that exists, e.g., the cavity is at a higher pressure than the filter and atmosphere. Passive venting can include valves that may be opened manually or automatically, but the force driving the smoke out is the natural pressure gradient as opposed to active venting. Passive valves, e.g., spring valves or umbrella valves, are configured to vent at a predetermined pressure. The venting pressure corresponds to a pressure that may be used to maintain a constant pressure in the surgical cavity and provide a desired venting rate.

Active venting provides venting due to an external force that is drawing gases and smoke out of the surgical cavity. For example, a vacuum, fan, or suction pump that creates a suction force to draw out the gases. Active valves are preferably actively controlled, for example electronically, to achieve a constant pressure in the surgical cavity and vent smoke and smoke plumes and gases at a predetermined rate to achieve optical clarity.

Figure 4:
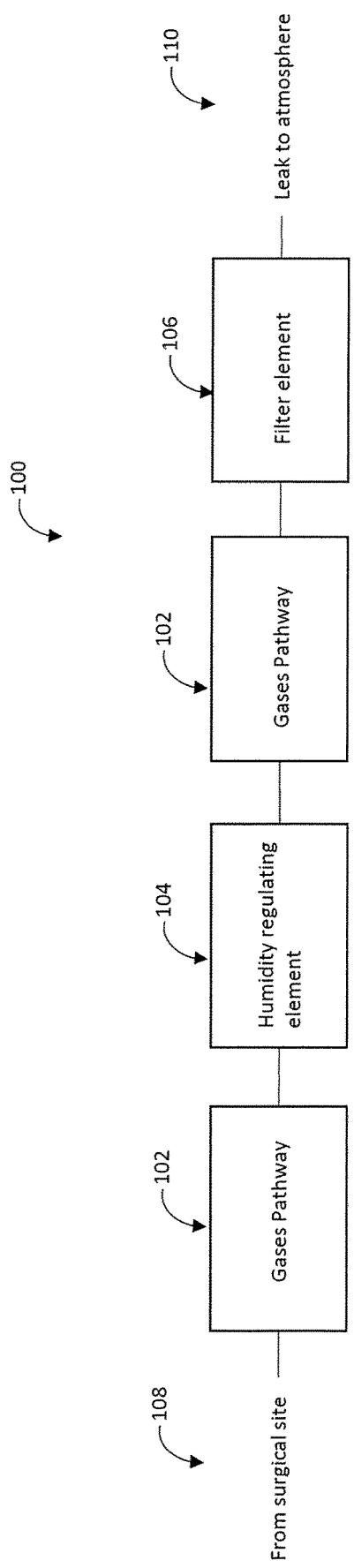
FIG. 4 illustrates a flow chart of a filter in a series configuration.
Figure 5:
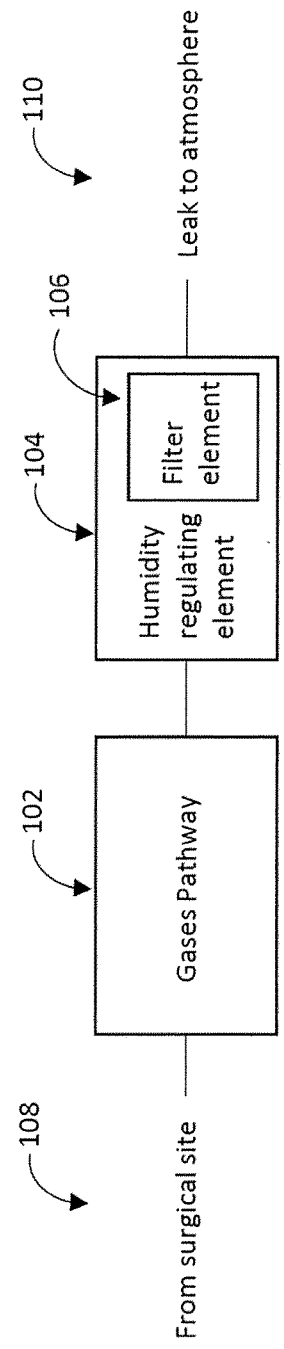
FIG. 5 illustrates a flow chart of a filter with a nested configuration.

As another example, the smoke filter may include passive openings, e.g. multiple openings or flow restricted openings, can be configured, e.g., shaped and structured to provide a desired venting rate. As shown in FIGS. 4 and 5, a first portion 108 of the smoke filter 100 is connected to a surgical site, for example by attachment to a cannula, while filtered smoke, vapor, or other gases leaks to atmosphere at a second portion 110. There may be an active or passive venting device at the second portion 110 as described above. The smoke filter 100 may include a gases pathway 102 to transport smoke and/or gases exhausted from a surgical site, a humidity regulating element 104 located along the gases pathway 102, and a filter element 106 located along the gases pathway 102 downstream of the humidity regulating element 104 such that the humidity regulating element 104 and the filter element 106 are in fluid communication with each other.

The gases pathway 102 is at least partially defined by a tube or conduit. The tube or conduit may provide a low resistance to flow for continuous flow. For example, the tube may be a flexible tube or alternatively may be a substantially inflexible tube. In some configurations, the gases pathway may be defined by a surgical cannula.

The humidity regulating element 104 and the filter element 106 may each include a single component or multiple components. The humidity regulating element 104 is configured to regulate humidity from the smoke and/or gases exhausted from the surgical site prior to the smoke and/or gases reaching the filter element 106, using any of the methods described herein. As non-limiting examples that are described in more detail below, the humidity regulating element 104 may regulate humidity based on a pore size of the filter element 106 or by bonding to a filter element 106. In some configurations, the humidity regulating element 104 removes or reduces humidity from the gas-path before the gas reaches the filter so that the humidity cannot condense on the filter and interact with the smoke particles. In some configurations, the humidity regulating element 104 condenses at least some moisture/humidity in the gas-path before the filter so that less humidity condenses on the filter and interact with the smoke particles. In some configurations, the humidity regulating element 104 is incorporated into the filter element 106 to allow moisture/humidity to pass through the filter without condensing so that it cannot interact with the smoke particles. In some configurations, humidity is regulated by increasing the filter surface area to reduce the chance of humidity and particle interactions, or reduce the density of these interactions. In some configurations, the humidity regulating element 104 also provides filtering, for example by including a desiccant.

The filter element 106 is configured to filter particulate matter from the smoke and/or gases exhausted from the surgical site. In some embodiments, the filter element 106 could include a particulate filter to filter particulate matter based on the pore size of the filter element 106, such as a HEPA or ULPA filter. Alternatively or additionally, the filter element 106 could include an activated carbon filter, a dust filter, and/or a desiccant to remove smoke or volatiles in the gases. The gases pathway 102 extends to atmosphere through the filter element 106 such that the filtered smoke and/or gases are vented to atmosphere after filtering.

As shown in FIG. 4, the humidity regulating element 104 may be in series with the filter element 106 such that the filter element 106 is spaced from and downstream of the humidity regulating element 104.

As another example, FIG. 5 shows that the humidity regulating element 104 and the filter element 106 may be in a nested configuration in the gases pathway 102. In some configurations, the filter element 106 may be at least partially or fully positioned within the humidity regulating element 104. In other configurations, the filter element 106 may at least partially surround or fully surround at least a portion of or the entirely of the humidity regulating element 104.

Figure 6:
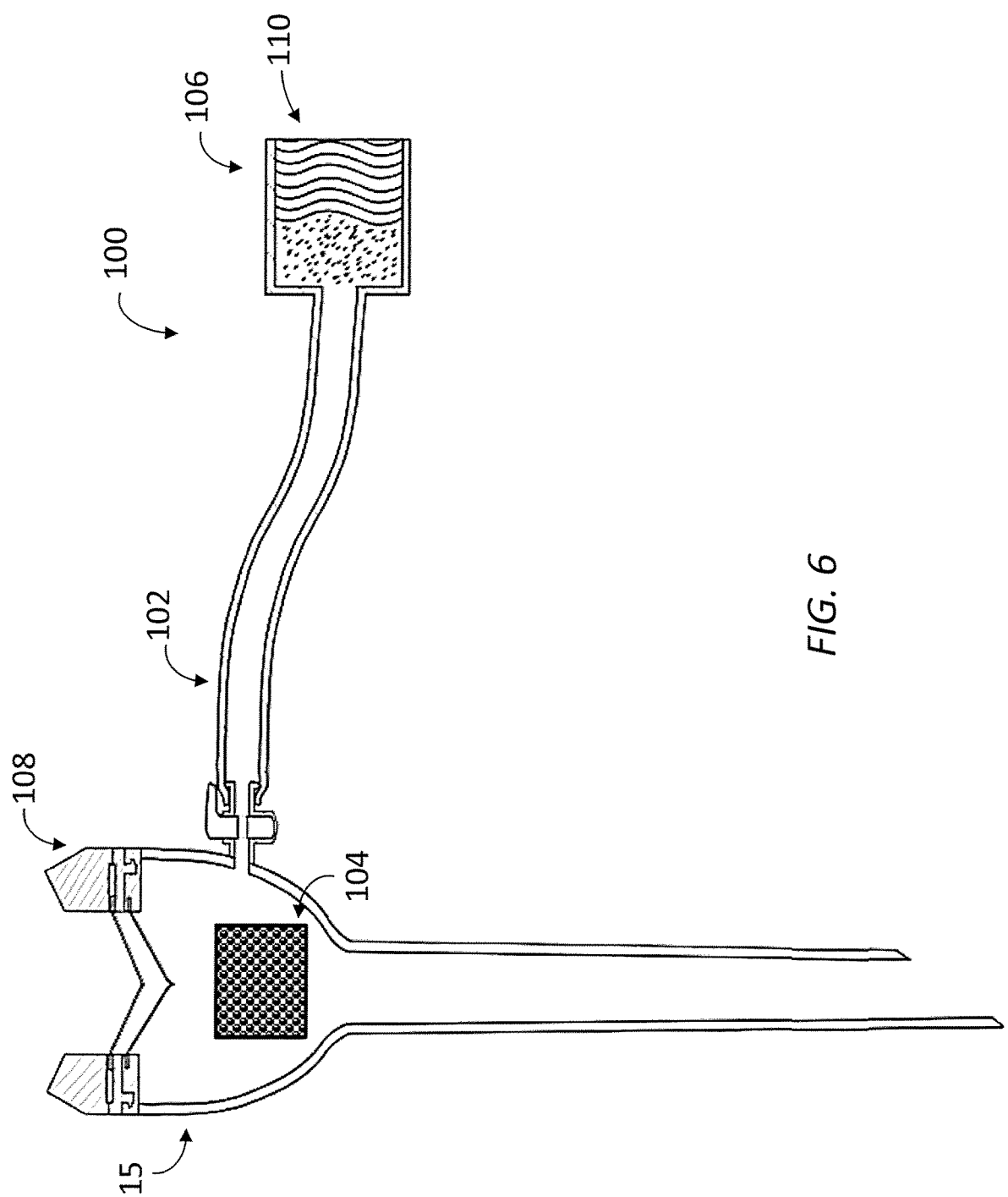
FIG. 6 illustrates a filter with at least a portion of the filter integrated into a cannula.
Figure 7:
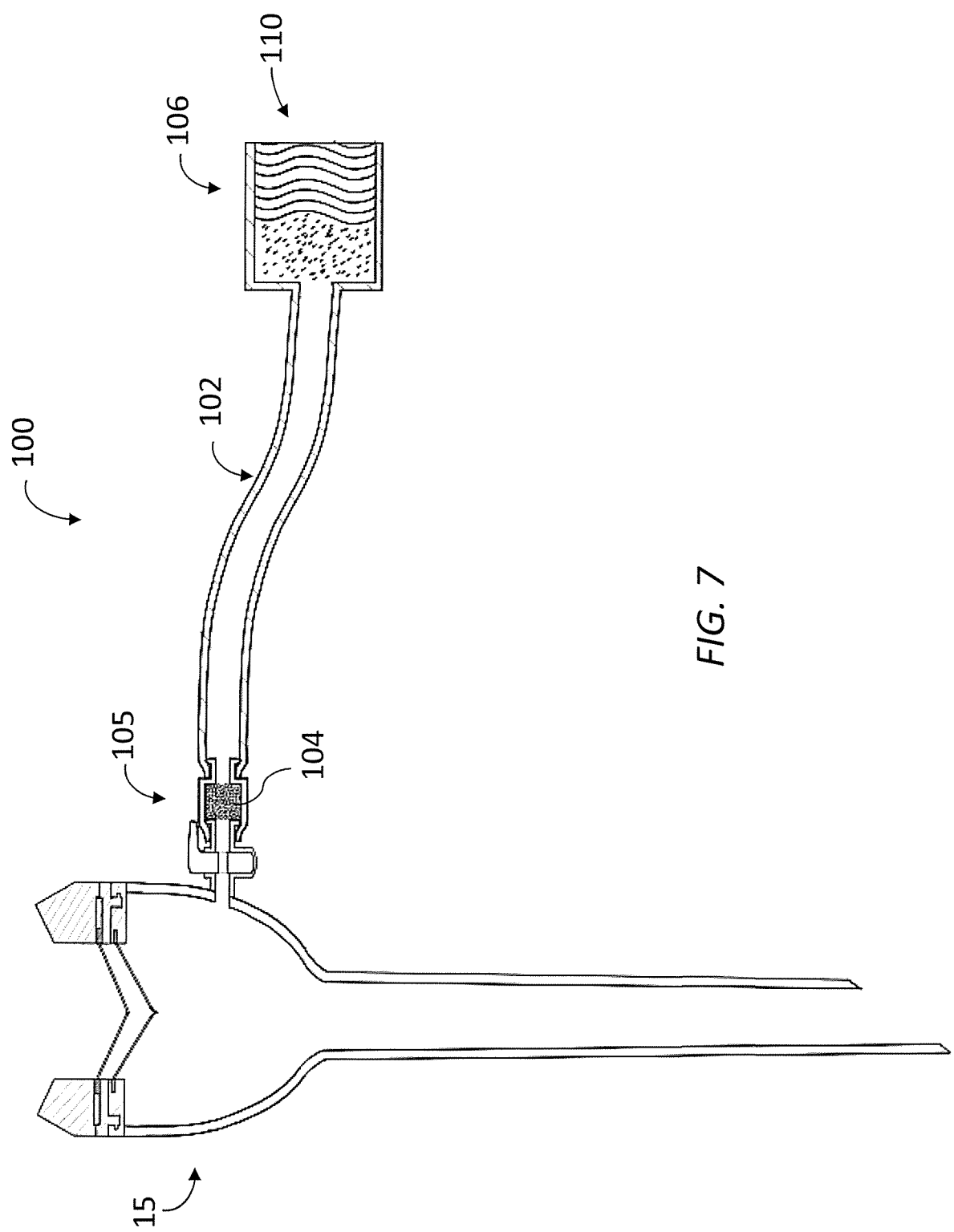
FIG. 7 illustrates a filter with at least a portion of the filter incorporated into a cannula attachment.
Figure 8:
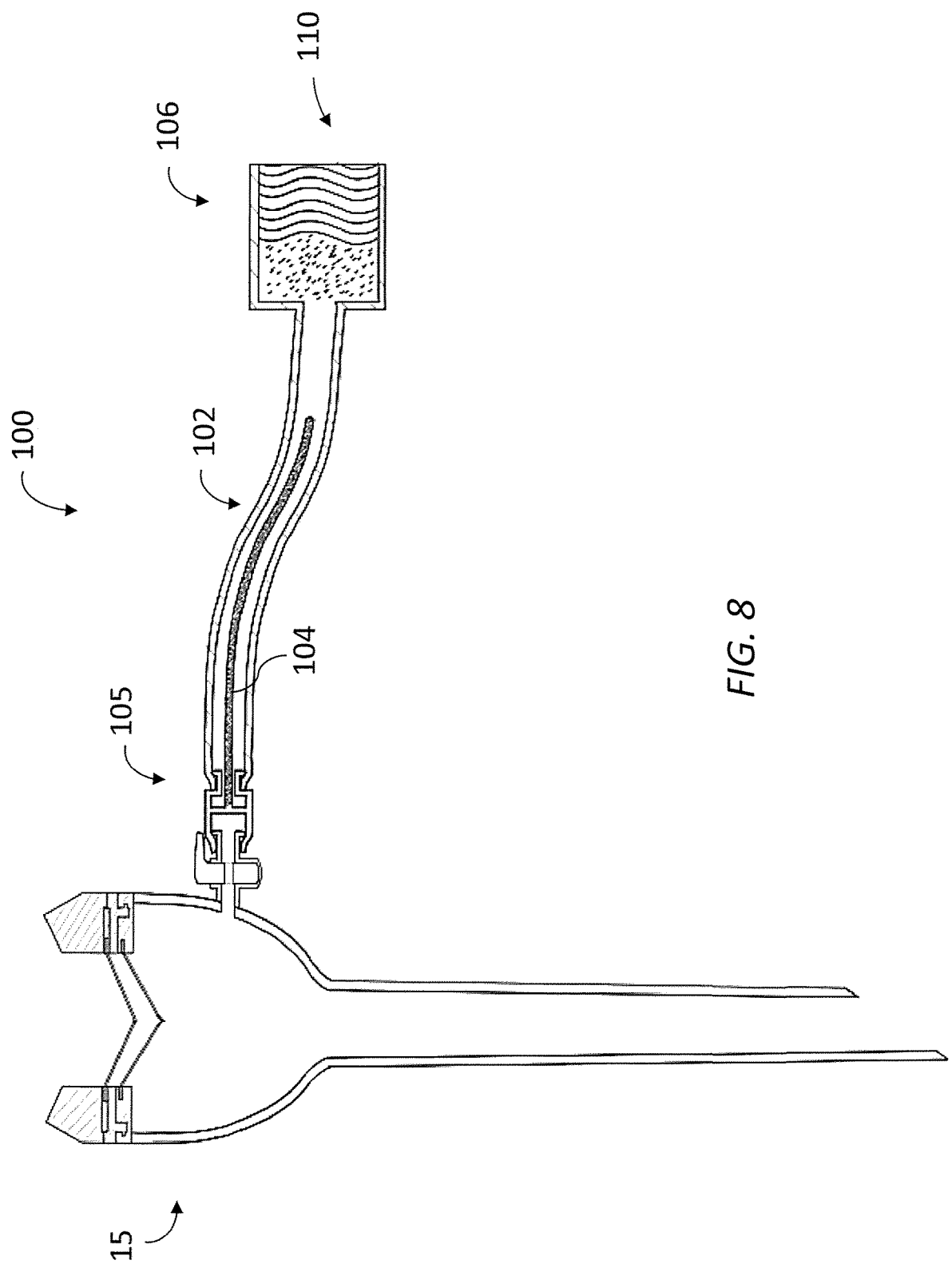
FIG. 8 illustrates a filter with an elongate structure (e.g., an insert rod) extending from a cannula attachment.

In some configurations, at least a portion of the smoke filter 100 may be integrated into the cannula 15. FIGS. 6 to 8 show the humidity regulating element 104 outside the filter element 106, e.g., in various elements of the cannula 15. For example, as shown in FIG. 6, the humidity regulating element 104 may be incorporated into the cannula 15. The humidity regulating element 104 removes moisture within the cannula 15, through any of the methods described below, before the gas is vented through the filter element 106.

In some configurations, as shown in FIG. 7, the humidity regulating element 104 may be incorporated into an attachment 105 to be connected to the cannula 15. The humidity regulating element 104 may heat the gas to a temperature above its dew point temperature or remove moisture, through any of the methods described below, before the gas is vented through the filter element 106. The attachment 105 may be a plastic adaptor or tubing to be connected to the cannula 15 and/or filter element 106 with a Luer or other connector.

In some configurations, a Luer connector can be configured to provide a leak-free and secure connection with less resistance to flow thereby increasing the overall performance of the surgical, e.g., insufflation system. In some configurations, a Luer lock connector is configured for use in a surgical, e.g., insufflation system. The Luer lock connector comprises: a body comprising a first end, a second end and an interior region; the interior region defining a gases flow passageway allowing insufflation gases to flow through the body from the first end to the second end; the body being operative to be coupled to a tubing arrangement at the first end and to a patient interface at the second end; and wherein, the second end is operative to be coupled to a patient interface fitting of the patient interface, the second end being further operative to lock and seal around an outer surface of the patient interface fitting when the Luer lock connector is coupled to the patient interface. Other Luer connectors that can be used or modified for use with configurations as disclosed herein can be found, for example, in PCT Pub. No. WO 2018/097738 to Boyes et al., which is hereby incorporated by reference in its entirety. For example, the Luer connector may include a neck region and an opening extending therethrough. The opening may have an inner diameter varying from a first diameter proximal to the neck region to a second diameter distal from the neck region. The first diameter may be less or smaller than the second diameter. As a fitting is inserted through the opening, the neck region is adapted to deform so to allow passage of the fitting. The Luer connector may include a confined area adapted to receive, engage and retain an end of the fitting. To do so, the inner diameter of the confined area may be, in some embodiments, greater than the inner diameter of the neck region. When connected, the neck region conforms around and/or presses the outer surface of the fitting thereby providing a tight seal between the Luer connector and the fitting.

In some configurations, as shown in FIG. 8, the humidity regulating element 104 may be an elongate structure (for example, an insert rod) extending from an attachment 105 to be connected to the cannula 15. The attachment 105 holds the elongate structure in place but allows the gas to flow along the gases pathway 102. The elongate structure may extend along at least a partial length of the tubing and toward the filter element 106. The humidity regulating element 104 may heat the gas to a temperature above its dew point temperature or remove moisture, through any of the methods described below, before the gas is vented through the filter element 106. For example, the humidity regulating element 104 may prevent the gases from condensing in the filter element 106 and prevent nucleation between humidity and smoke particles. This may be achieved by heating the gases so humidity remains in a vapor and/or state or using a hydrophilic coating or otherwise to direct humidity or moisture away from the filter element 106 to prevent condensation.

With reference to FIGS. 6-42, illustrative embodiments of the smoke filter is shown. The smoke filters in FIGS. 6-42 may include features and configurations of the smoke filter 100 discussed above. Any of the features smoke filters may be combined or substituted with any features described with respect to FIGS. 6-42. Accordingly, numerals used to identify features of the smoke filter 100 are incremented by factors of one hundred to identify like features of the smoke filters. This numbering convention generally applies to the remainder of the figures. Any component or step disclosed in any embodiment in this specification can be used in other embodiments. As noted elsewhere herein, while filters described herein may be described as smoke filters or filters for filtering smoke, any of the filters (e.g., smoke filters) described herein may be configured to filter out and/or trap other particulate matter such as the medicament, chemicals or other substances.

Smoke Venting Filters with Desiccant

In some configurations, the humidity regulating element may include a desiccant to remove humidity from the gas path. The desiccant may include a plurality of granules of desiccant material. For example, the desiccant may be medical grade silica and in granule/bead form to allow gas to flow through the material. Other non-limiting examples of desiccants that can be used, alone or in combination, can include activated charcoal, calcium sulfate, calcium chloride, activated alumina and molecular sieves, e.g., zeolites.

Figure 9:
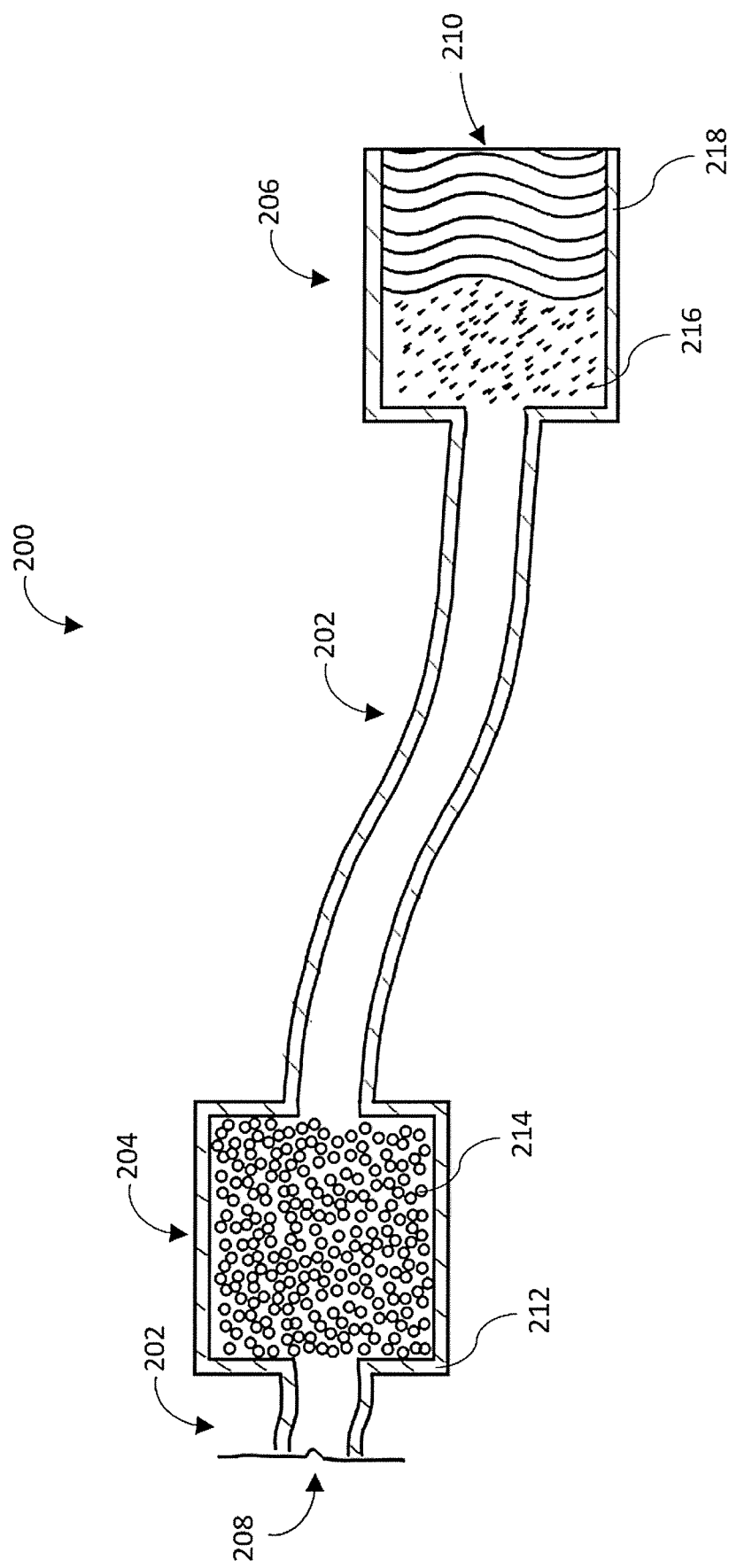
FIG. 9 illustrates a filter with a desiccant based humidity regulating element in series with a filter element.

As shown in FIG. 9, the smoke filter 200 may include a first portion 208 leading from a surgical site, a gases pathway 202 transporting smoke and/or gases exhausted from the surgical site, a humidity regulating element 204 located along the gases pathway 202, and a filter element 206 downstream of the humidity regulating element 204 such that the humidity regulating element 204 and the filter element 206 are in fluid communication with each other. At least a portion of the gases pathway 202 may be surrounded by a flexible plastic tubing or an inflexible tubing. The humidity regulating element 204 may include a housing 212 with a desiccant 214 located therein to remove or reduce humidity from the smoke and/or gases exhausted from the surgical site prior to the smoke and/or gases reaching the filter element 206. The filter element 206 may include one or more filter media 216, such as an activated carbon and/or a particulate filter media (such as ULPA or HEPA), located within a separate housing 218. The order of the one or more filter media 216 may be interchangeable. For example, the activated carbon may be upstream or downstream of the particulate filter media. In some configurations, the activated carbon and particulate filter media may be integrated into a single filter. The gases pathway 202 extends to atmosphere through the filter element 206 such that the filtered smoke and/or gases are vented to atmosphere at the second portion 210.

Figure 10C:
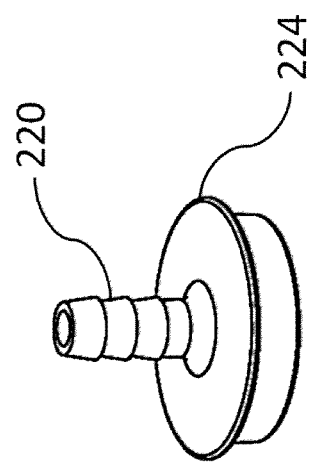
FIGS. 10A-10H illustrate various example humidity regulating elements.
Figure 10B:
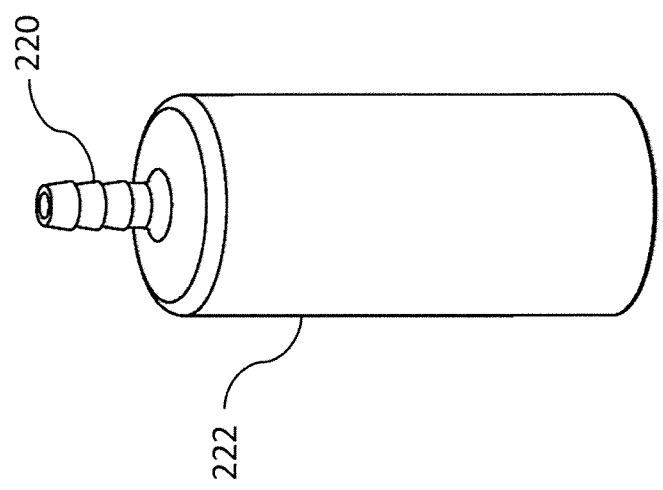
Figure 10A:
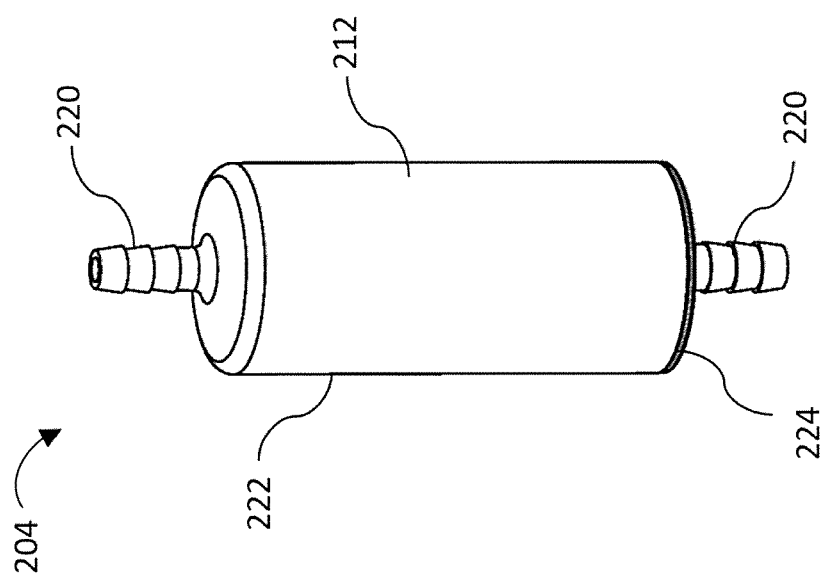

FIGS. 10A-10C illustrate an example housing 212 for holding the desiccant 214. The housing 212 may include one or more connectors 220 for joining to the gases pathway 202. The housing 212 may include a body portion 222 and a cap portion 224 that is removable or non-removable. The cap portion 224 may be removed so the housing 212 may be filled with the desiccant 214. As shown, the body portion 222 may have an elongate or cylindrical shape but may take on any other shape. A cylindrical shape is configured to achieve a predetermined level of drying, e.g., a predetermined level of humidity removal. Ideally, the gases/smoke are completely dried prior to reaching the filter. The housing 212 may also include additional walls or baffles therein to extend the flow path such that the humidified smoke residence time within the moisture reduction element, such as, for example, desiccant 214, is extended to promote and achieve drying of the vented smoke/gases. The walls or baffles may define a tortuous path through the housing.

Figures 10D, 10E, 10F:
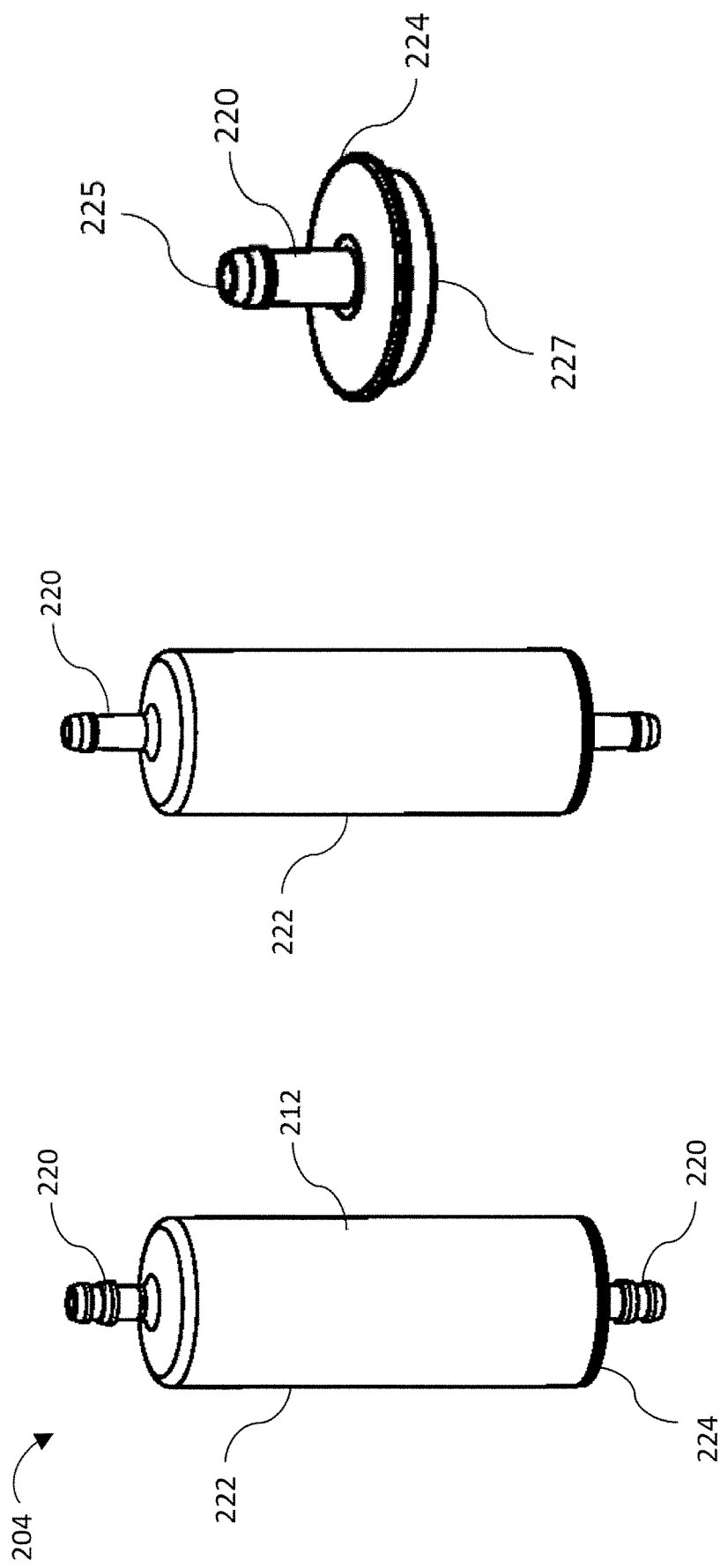

FIG. 10D illustrates another example of the housing 212 with a different type of connector 220 than FIGS. 10A-10C. The same or different connectors 220, for example Luer connectors, may be positioned at either end of the housing 212.

FIG. 10E illustrates yet another example of the housing 212 with a different type of Luer connector 220. The connectors 220 may each have one or more threads, rings, protrusions, or barbs 225 for sealing with another component. FIG. 10F shows the cap portion 224 of the housing 212 shown in FIG. 10E. The connector 220 of the cap portion 224 includes a single thread, ring, protrusion, or barb 225. The opposite end 227 of the cap portion 224 connects to the body portion 222. The opposite end 227 may have a continuous, annular structure.

Figure 10H:
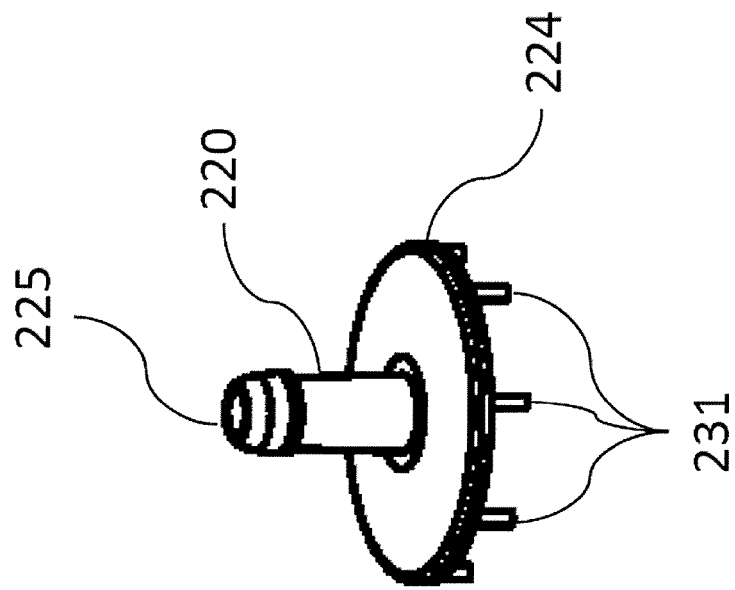
Figure 10G:
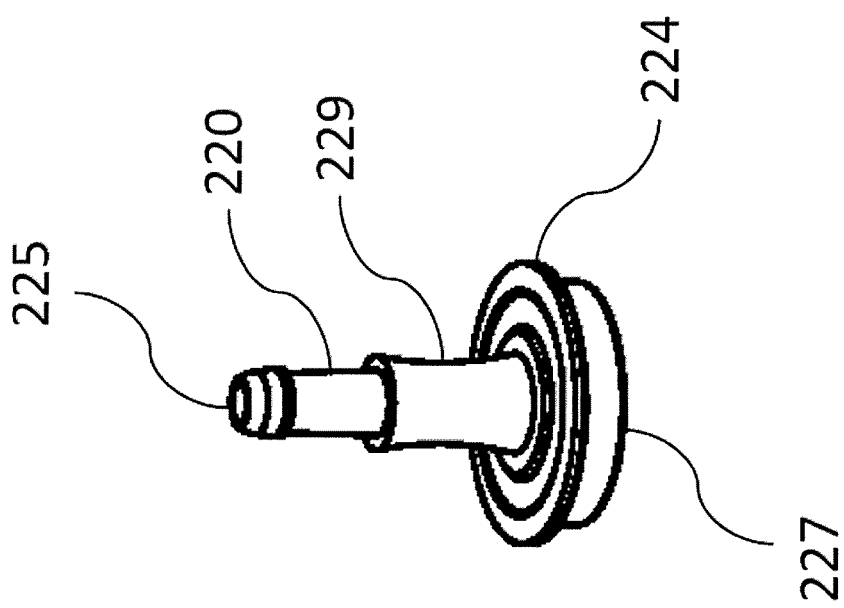

FIGS. 10G-10H illustrate different cap portions 224 that may be used with the housing 212, and may be either removable or non-removable. In FIG. 10G, the cap portion 224 includes a handle 229 that allows a user to grip the housing 212 and facilitates removal of the cap portion 224. FIG. 10H illustrates a cap portion 224 configured to press-fit with the body portion 222. The cap portion 224 has a plurality of structures 231, e.g., legs, that are press fit into corresponding receiving structures, e.g., apertures, in the body portion 222. Alternatively, the cap portion 224 may include a plurality of receiving structure to receive a plurality of structures on the body portion 222. The press fit connection allows the cap portion 224 to be removed and replaced and allows interchangeability of the cap portion 224. In some configurations, the cap portion 224 may include a filter integrated within the cap portion 224.

FIGS. 10I-10L illustrate an example housing 212 for holding the desiccant 214. The housing 212 may include one or more connectors 220 for joining to the gases pathway. As illustrated, the housing 212 has a substantially square shape, but other shapes are possible. The housing 212 may include a body portion 222 and a cap portion 224 that is removable or non-removable. The housing 212 may be filled with the desiccant 214. There is no separate filter media in the housing 212. One or more filter elements may be positioned downstream of the housing 212.

Figure 11:
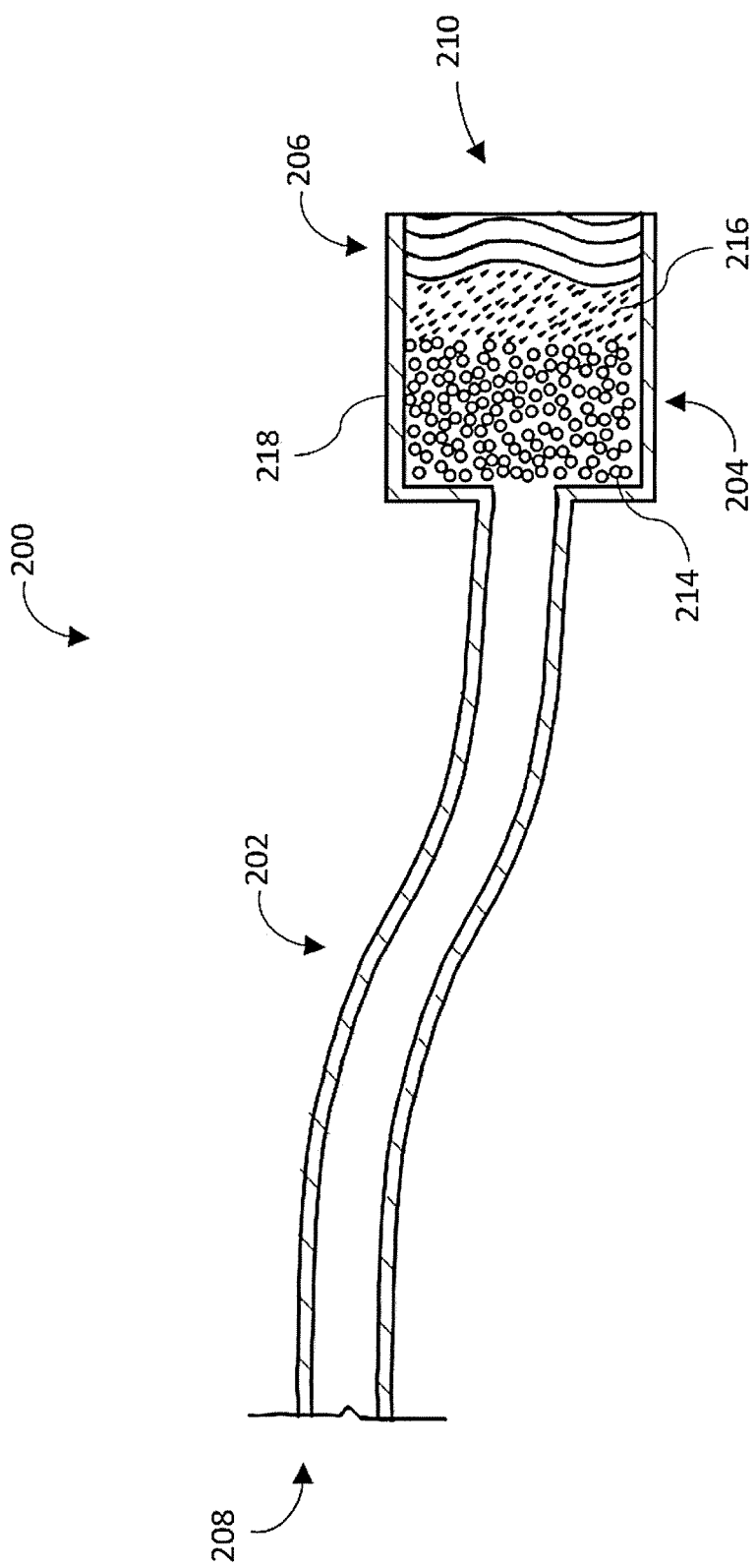
FIG. 11 illustrates a filter with a desiccant based humidity regulating element in a nested configuration with a filter element.

FIG. 11 illustrates another configuration of the smoke filter 200. The smoke filter 200 may include a first portion 208 leading from a surgical site, a gases pathway 202 transporting smoke and/or gases exhausted from the surgical site, a humidity regulating element 204 located along the gases pathway 202, and a filter element 206 in fluid communication with the humidity regulating element 204. At least a portion of the gases pathway 202 may be surrounded by a flexible plastic tubing or an inflexible tubing. The humidity regulating element 204 may be at least partially or fully housed within the tubing of the gases pathway 202 and/or the filter element 206. As shown, the filter element 206 may include one or more filter media 216, such as an activated carbon and/or particulate filter media (such as a ULPA or HEPA filter), located within a housing 218. The humidity regulating element 204 may include a desiccant 214 located within the housing 218 and upstream from the filter media 216 to remove or reduce humidity from the smoke and/or gases exhausted from the surgical site prior to the smoke and/or gases reaching the filter media 216. Viewed another way, the filter media 216 may be at least partially or entirely located within a housing of the humidity regulating element 204 and downstream from the desiccant 214. The gases pathway 202 extends to atmosphere through the filter element 206 such that the filtered smoke and/or gases are vented to atmosphere at the second portion 210.

Figure 11B:
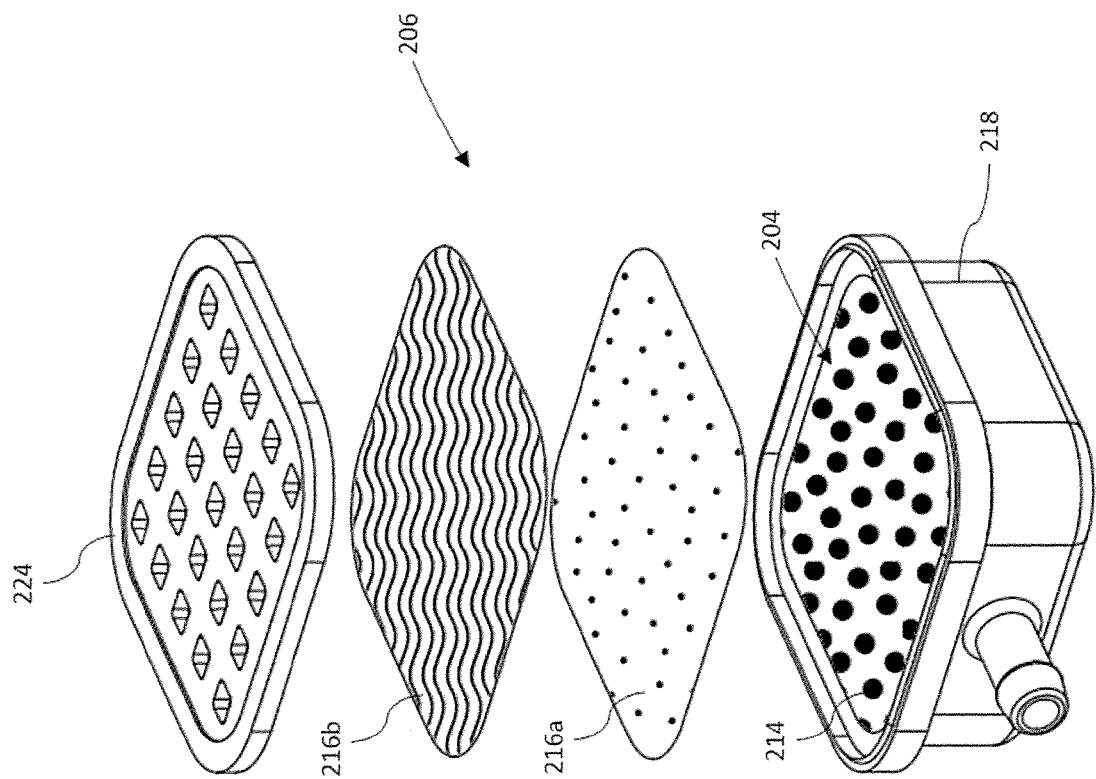
FIGS. 11A and 11B illustrate a filter with a desiccant based humidity regulating element and a filter element with one or more filter media.
Figure 11A:
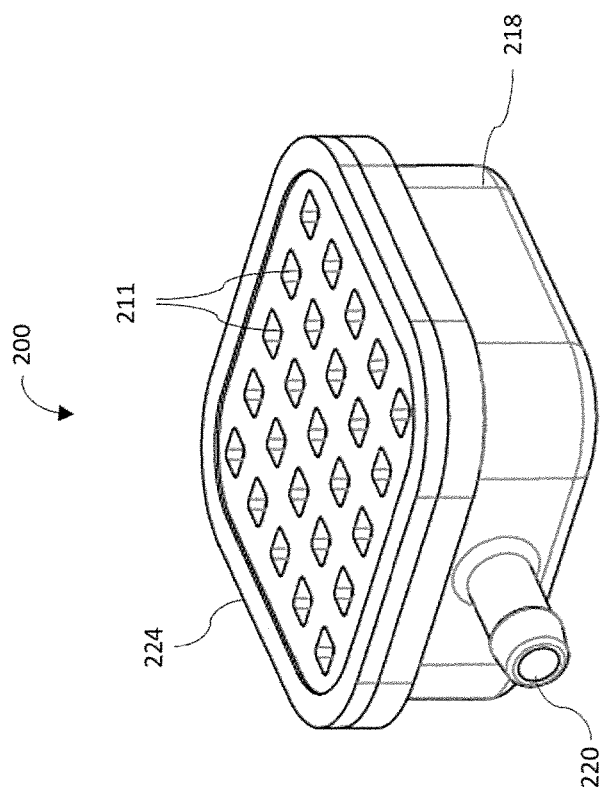
Figure 12B:
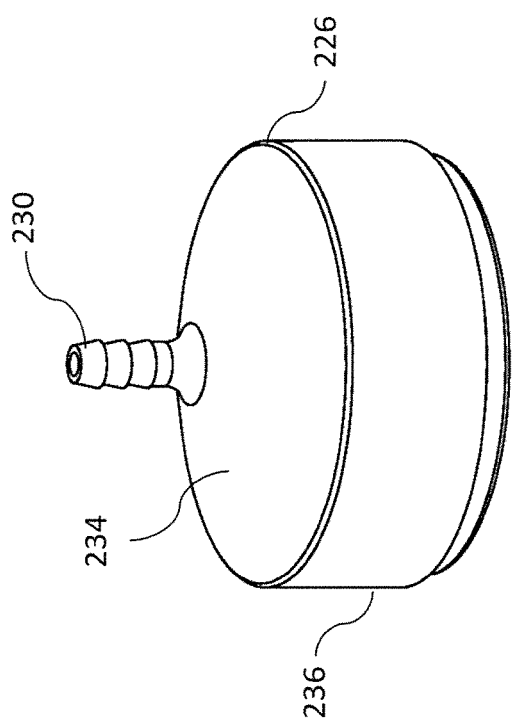
FIGS. 12A-12I illustrate various example humidity regulating elements nested within a filter element.
Figure 12D:
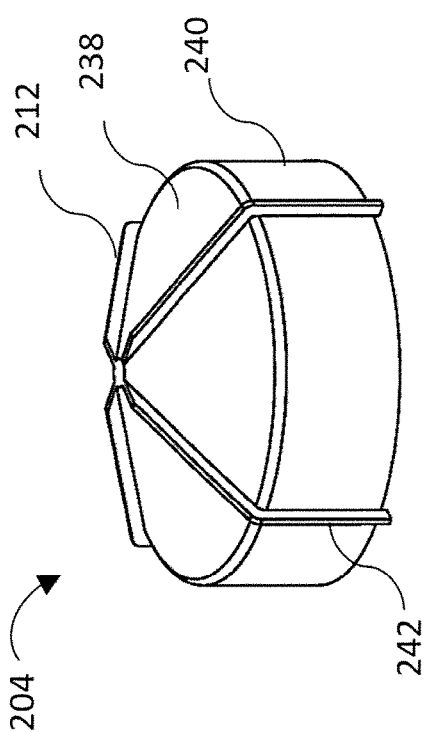
Figure 12A:
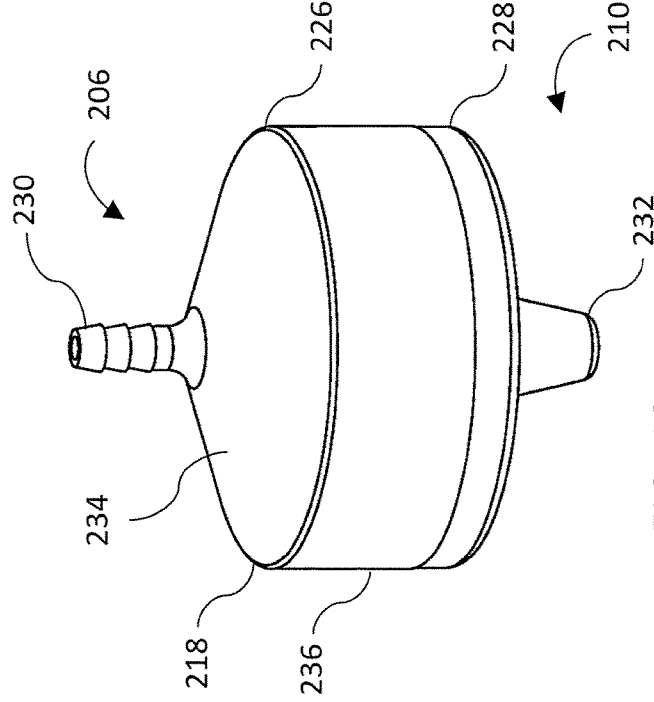
Figure 12C:
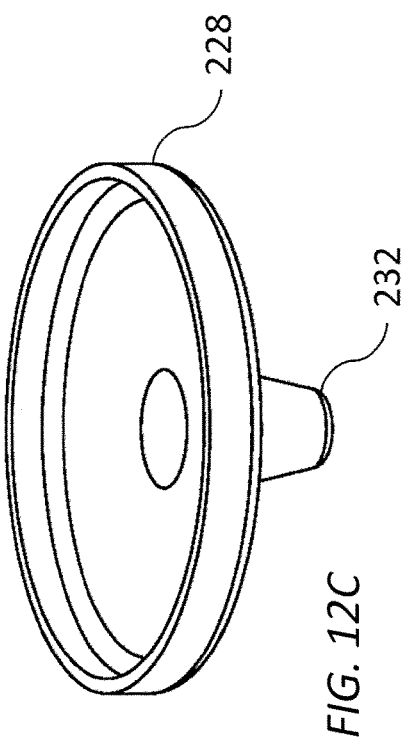
Figure 12E:
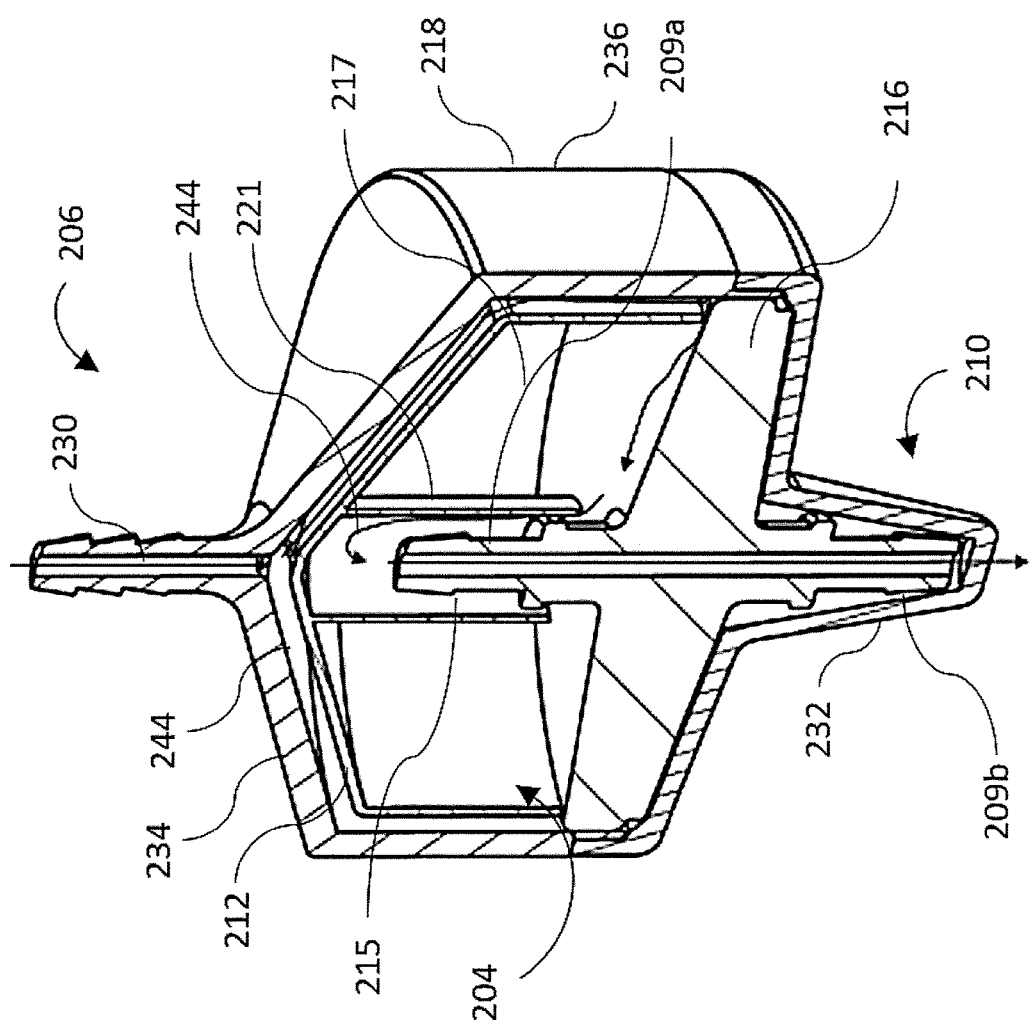

FIGS. 11A and 11B illustrates a possible configuration of the filter 200. As shown in FIG. 11A, the housing 218 may include a connector 220 configured to be placed in connection with the gases pathway 202. As illustrated, the housing 218 has a substantially square shape, but other shapes are possible. The filter 200 may include a cap 224 that may be removable or non-removable from the housing 218. The filtered smoke and/or gases are vented to atmosphere through one or more outlets 211 in the cap 224 and/or housing 218. An axis extending through any or all of the one or more outlets 211 may be parallel to or perpendicular to an axis extending through the connector 220. For example, as shown in FIG. 11A, the cap 224 includes a plurality of outlets 211 arranged in an array. The cap 224 includes a number of parallel rows including the same number of outlets 211. As shown in FIG. 11B, the housing 218 may contain a humidity regulating element 204 and/or a filter element 206 in fluid communication with the humidity regulating element 204. The humidity regulating element 204 may include a desiccant 214 located within the housing 218 and upstream from the filter media 216a, 216b within the same housing 218 to remove or reduce humidity from the smoke and/or gases exhausted from the surgical site prior to the smoke and/or gases reaching the filter media. The filter media 216a, 216b may be positioned between the humidity regulating element 214 and the one or more outlets 211. The filter element 206 may include one or more filter media such as a first filter media 216a and/or a second filter media 216b. One of the first or second filter media 216a, 216b may include activated carbon, particulate filter (such as a ULPA or HEPA filter), or other filter media. FIG. 12E illustrates an example filter 206 and humidity regulating element 204. The filter housing 218 (FIG. 12A) houses a separate housing 212 of the humidity regulating element 204 (FIG. 12D). The filter housing 218 may include an inlet connector 230 for connecting to the gases pathway 202 and an outlet connector 232 at the second portion 210 of the filter 206 (e.g., smoke filter) for filtered smoke and/or gases to be vented to atmosphere. The outlet connector 232 may be on the opposite side of the filter 206 as the inlet connector 230. As illustrated, the outlet connector 232 may be coaxial with the inlet connector 230. The filter housing 218 may also include a tapered wall portion 234 extending from the inlet connector 230 and a cylindrical sidewall portion 236 extending from the tapered wall portion 234. As shown, a diameter of the cylindrical sidewall portion 236 is greater than a length of the cylindrical sidewall portion 236 but other shapes and dimensions are possible. The filter housing 218 may include a body portion 226 (FIG. 12B) and a cap portion 228 (FIG. 12C) that can be either removable or non-removable). The cap portion 228 may be removed so the filter media 216 and/or desiccant 214 may be positioned in the housing 218.

FIG. 12D illustrates the separate housing 212 of the humidity regulating element 204. The separate housing 212 may include a tapered wall portion 238 and a cylindrical sidewall portion 240 generally sized and shaped to be positioned within the tapered wall portion 234 and the cylindrical sidewall portion 236 of the filter housing 218. The separate housing 212 may include one or more guide elements 242 extending along the tapered wall portion 238 and/or the cylindrical sidewall portion 240. When assembled, the guide element(s) 242 separate the separate housing 212 from the inner surface of the filter housing 218 and form a gases passageway 244 (see FIG. 12E). The filter element 216 may be nested within or downstream from the separate housing 212. The filter element 216 may be removably connected to the separate housing 212 to allow for replacement or changing of the filter and/or refilling the desiccant within the separate housing 212.

Figure 12F:
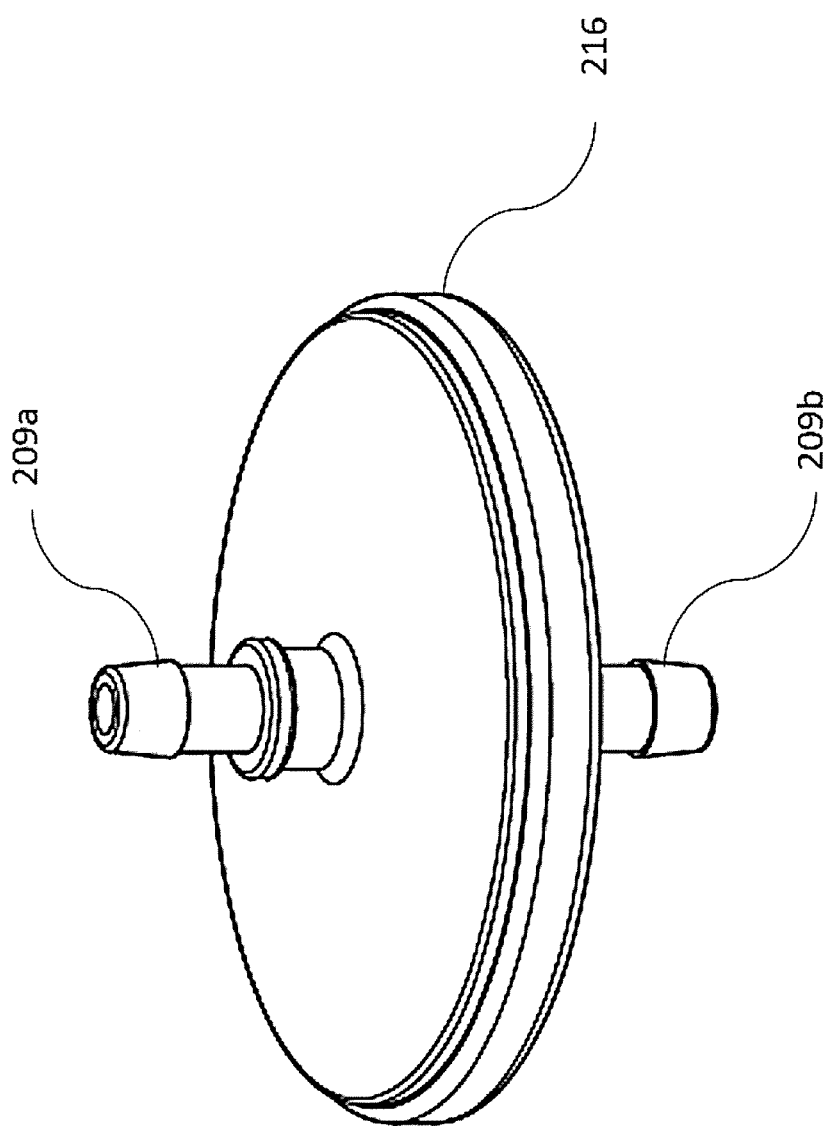
Figure 12H:
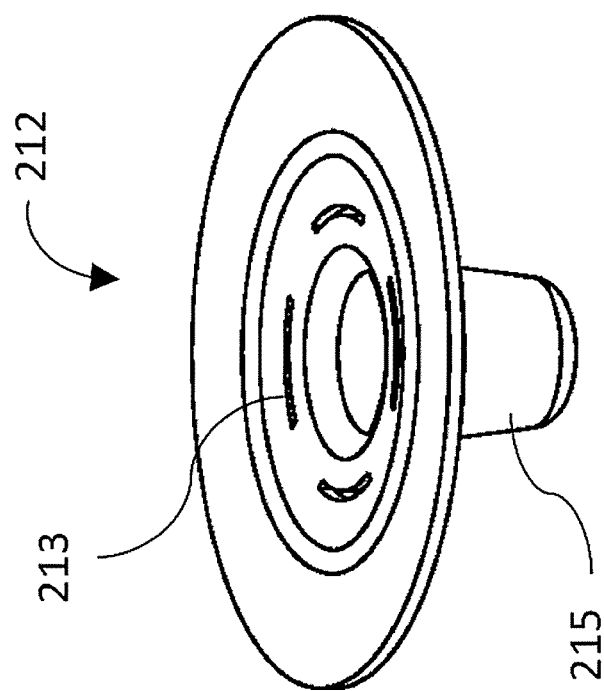
Figure 12G:
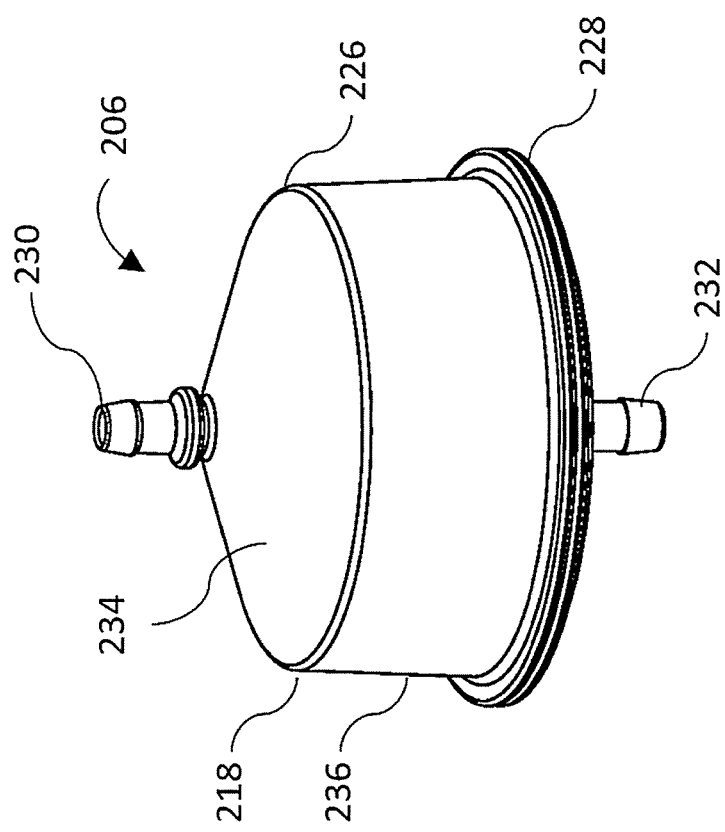

FIG. 12E illustrates the flow of one or more gases through the filter 206. Although the inlet connector 230 is aligned with the filter element inlet 209a and/or the outlet connector 232, one or more gases passageways force fluid in a non-longitudinal flow path. For example, gases flow into the inlet connector 230 and are forced through a defined gases passageway 244 formed between the outer surface of the separate housing 212 and the inner surface of the filter housing 218. The passageway 244 may generally direct the gases along an inner periphery of the filter housing 218 and in a direction generally toward the outlet connector 232. Gases flow out of the gases passageway 244 and into an interior of the separate housing 212. The gases flow centrally and through a region 217 within the separate housing 212 having the desiccant. From the desiccant, gases flow through the filter element 216 located downstream from the desiccant. To reach the filter element 216, the gases may be forced through a defined passageway 244 within a lumen 221 of the separate housing 212. The passageway 244 may be disposed between the lumen 221 of the separate housing 212 and the inlet 209a of the filter element 216. The filter element inlet 209a may be concentric with the lumen 221. To travel through the passageway 244, the gases may be forced to flow in a direction toward the inlet connector 230 before being forced through the filter inlet 209a in a direction toward the outlet connector 232. The filtered gases flow out of the outlet connector 232 to atmosphere. This construction forces all of the flow of gases and smoke to travel through the desiccant before travelling out of the filter element 216. The separate housing 212 and the filter housing 218 provide a wide area to help increase residence time of the gases and/or smoke within the region 217 having the desiccant. In other words, the separate housing 212 and the filter housing 218 reduce the velocity of the gases and/or smoke entering the separate housing 212 and filter housing 218, hence increasing residence time. This removes or reduces the humidity content of the gases and/or smoke prior to entering the filter element 216, thereby reducing clogging of the filter element 216. FIG. 12F shows the filter element 216 alone. The filter element 216 may have an inlet 209a configured to receive the gases from the region 217 and an outlet 209b. The inlet 209a may be disposed within the lumen 221 of the separate housing 212 and coaxial with the inlet connector 230. The outlet 209b of the filter media 216 may be disposed within the outlet connector 232 and coaxial with the outlet connector 232.

Figure 12I:
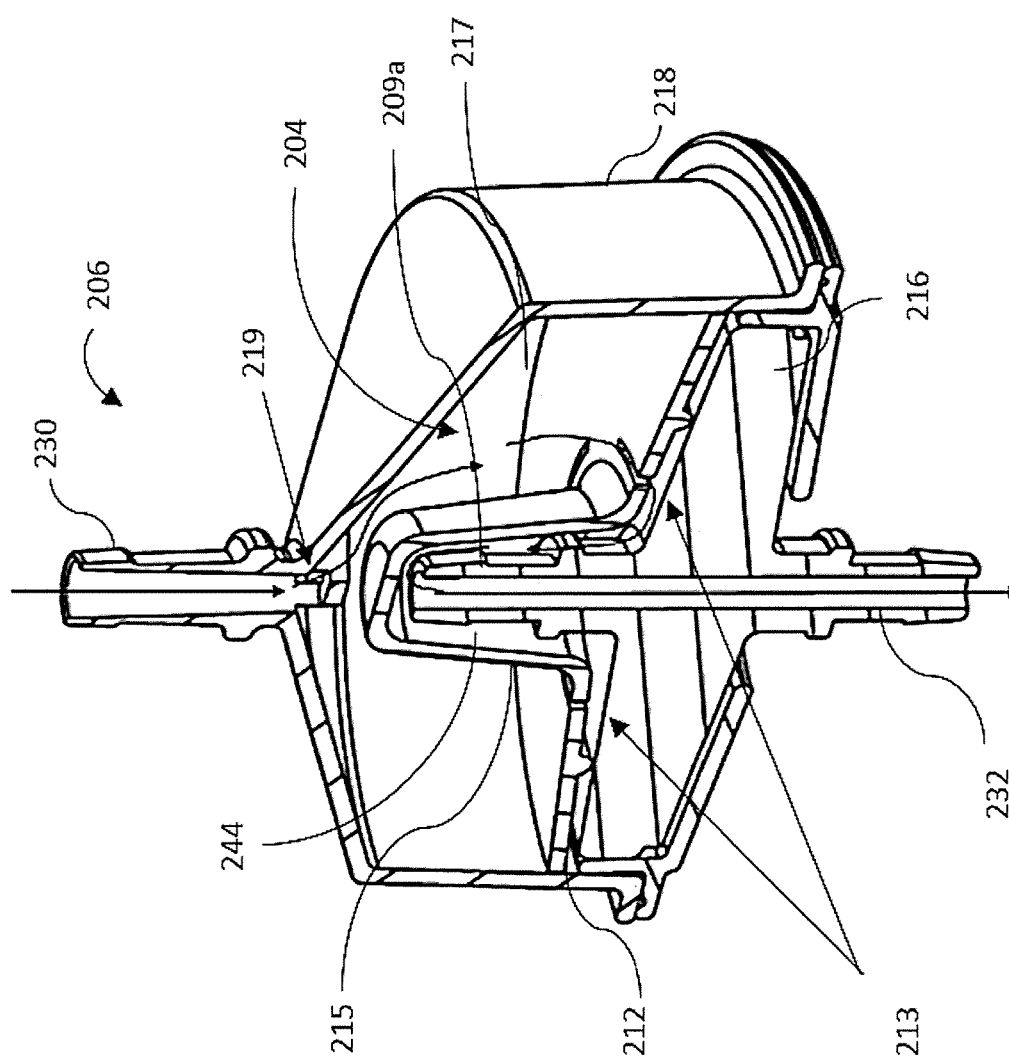

FIG. 12I illustrates another example filter 206 and humidity regulating element 204, which can include any features of the example shown in FIGS. 12A-12F. The filter housing 218 (FIG. 12G) houses a separate housing or inner wall structure 212 (FIG. 12H) for separating desiccant from the filter element 216. The separate housing or inner wall structure 212 includes one or more openings 213 to allow gases to flow through the inner wall structure 212. The one or more openings 213, e.g., two, three, four, or more, are shaped and sized to control the venting rate out of the filter and ensure an adequate dwell time in the desiccant to cause drying of the gases/smoke. FIG. 12I illustrates the flow of one or more gases through the filter 206. Although the inlet connector 230 is coaxial with the filter element inlet 209a and/or the outlet connector 232, one or more gases passageways force fluid in a non-longitudinal flow path. For example, gases flow into the inlet connector 230 and through one or more openings 219 at a distal end of the inlet connector 230 and into the region 217 having the desiccant (not shown). Each of the one or more openings 219 has a smaller diameter than the inlet connector 230. The gases flow around a tapered structure 215 of the separate housing 212 and through the region 217 in a direction generally toward the openings 213. From the region 217 having the desiccant, gases flow through the openings 213 in the inner wall structure 212 and toward the inlet 230 and into the tapered structure 215, for example in the passageway 244 between the tapered structure 215 and the filter media inlet 209a. The filter media inlet 209a may be concentric with the tapered structure 215. The tapered structure 215 may include a closed end closest to the inlet connector 230 and an open end closest to the outlet 232. To travel through the passageway 244, the gases may be forced to flow in a direction toward the inlet 230 before being forced through the inlet 209a in a direction toward the outlet 232. The natural pressure gradient eventually drives the gases through the filter 216 and out of the outlet 232. The filtered gases flow out of the outlet 232 to atmosphere. The filter media 216 may resemble the filter media 216 shown in FIG. 12F. The outlet connector 232 may be the same structure as the filter media outlet 216b or different structures as shown in FIG. 12F.

Figure 13:
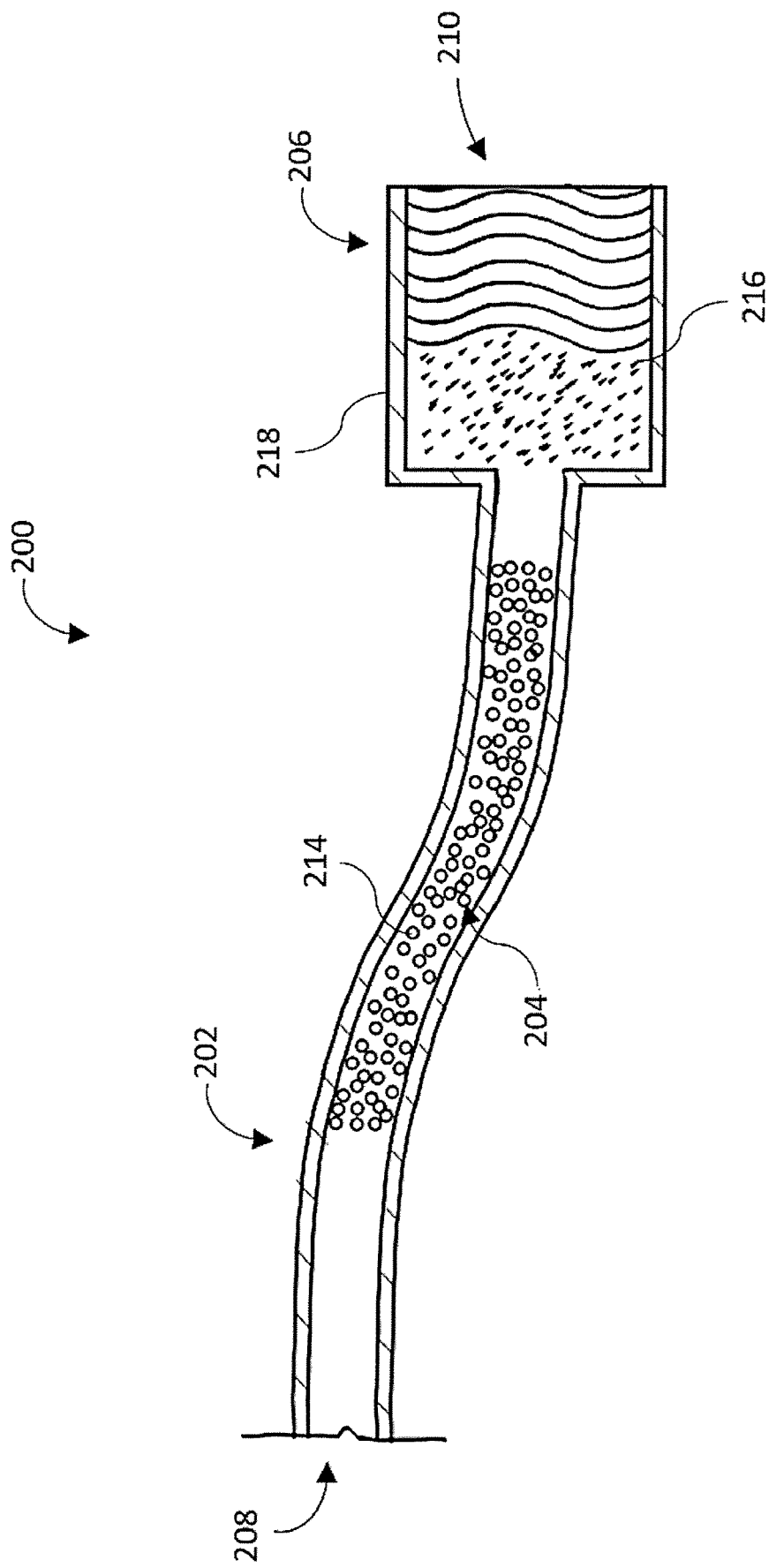
FIG. 13 illustrates a filter with a desiccant based humidity regulating element within a tubing.

FIG. 13 illustrates yet another configuration of the smoke filter 200. The smoke filter 200 may include a first portion 208 leading from a surgical site, a gases pathway 202 transporting smoke and/or gases exhausted from the surgical site, a humidity regulating element 204 located along the gases pathway 202, and a filter element 206 in fluid communication with the humidity regulating element 204. At least a portion of the gases pathway 202 may be surrounded by a flexible plastic tubing or an inflexible tubing. The humidity regulating element 204, which may include a desiccant 214, may be at least partially or fully housed within the tubing of the gases pathway 202 to remove or reduce humidity from the smoke and/or gases exhausted from the surgical site prior to the smoke and/or gases reaching the downstream filter element 206. The filter element 206 may include one or more filter media 216, such as an activated carbon and/or particulate filter media (such as ULPA or HEPA), located within a housing 218. The gases pathway 202 extends to atmosphere through the filter element 206 such that the filtered smoke and/or gases are vented to atmosphere at the second portion 210.

Figure 14:
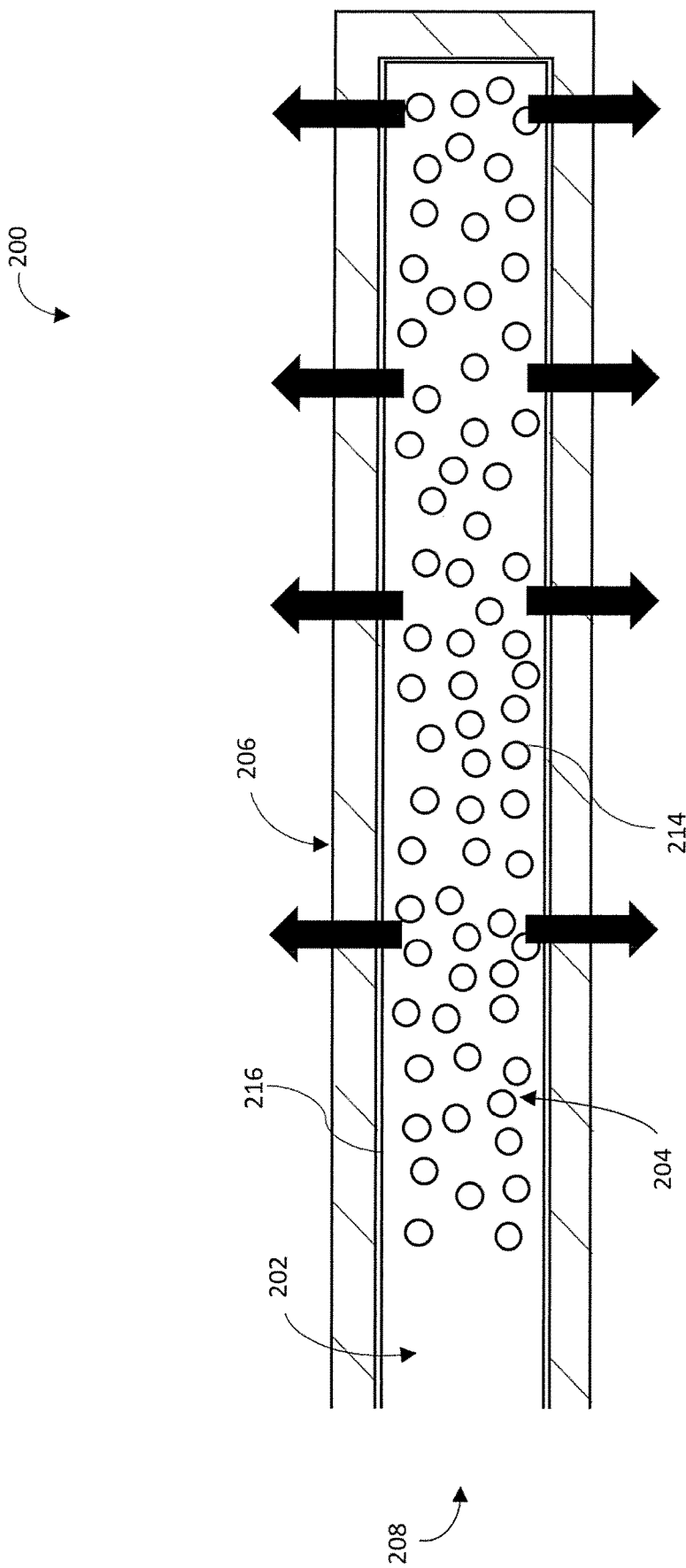
FIG. 14 illustrates a nested, desiccant based humidity regulating element and filter element within a flexible tubing.

FIG. 14 illustrates another configuration of the smoke filter 200. The smoke filter 200 may include a first portion 208 leading from a surgical site, a gases pathway 202 transporting smoke and/or gases exhausted from the surgical site, a humidity regulating element 204 located along the gases pathway 202, and a filter element 206 in fluid communication with the humidity regulating element 204. The humidity regulating element 204 and the filter element 206 may be in a nested configuration. For example, the humidity regulating element 204 may be at least partially or fully housed within the outer wall of the gases pathway 202 and/or the filter element 206. The filter element 206 may form an outer wall of the gases pathway 202. The humidity regulating element 204 may include a desiccant 214 located within a lumen of the tubing or the filter element 206. The desiccant 214 removes or reduces humidity from the smoke and/or gases exhausted from the surgical site prior to the smoke and/or gases reaching the filter element 206. The filter element 206 may include one or more filter media 216, such as an activated carbon and/or particulate filter media (such as ULPA or HEPA), located along a length of the gases pathway 202. The gases pathway 202 extends to atmosphere through the filter element 206 such that the filtered smoke and/or gases are vented to atmosphere.

Figure 15:
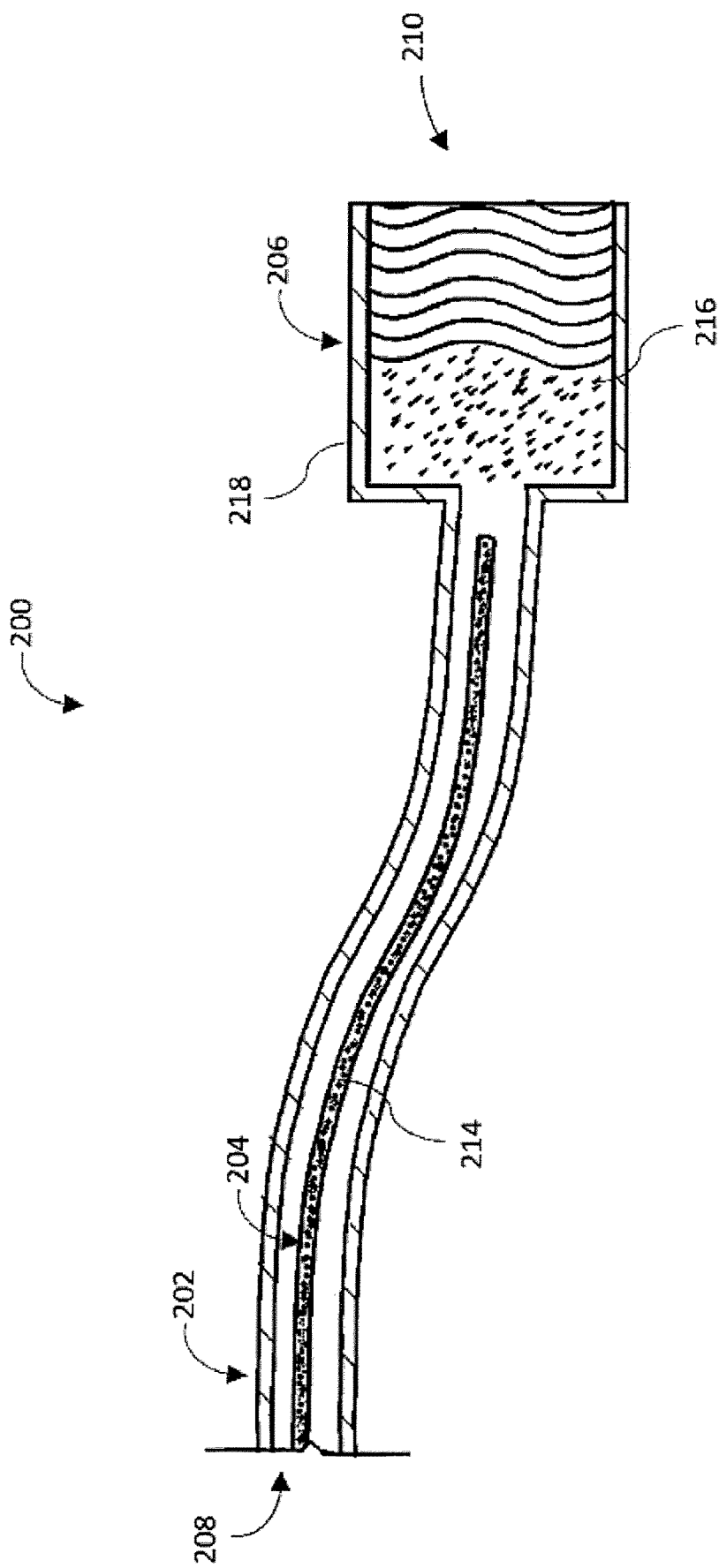
FIG. 15 illustrates a filter with a humidity regulating element having a desiccant based rod extending through a flexible tubing.

FIG. 15 illustrates yet another configuration of the smoke filter 200. The smoke filter 200 may include a first portion 208 leading from a surgical site, a gases pathway 202 transporting smoke and/or gases exhausted from the surgical site, a humidity regulating element 204 located along the gases pathway 202, and a filter element 206 in fluid communication with the humidity regulating element 204. At least a portion of the gases pathway 202 may be surrounded by a flexible plastic tubing. The humidity regulating element 204 may include a desiccant 214 at least partially or fully housed within the tubing of the gases pathway 202 to remove or reduce humidity from the smoke and/or gases exhausted from the surgical site prior to the smoke and/or gases reaching the downstream filter element 206. The desiccant 214 may be formed into an elongate structure (e.g., a rod) that extends at least partly through a lumen of the tubing. The filter element 206 may include one or more filter media 216, such as an activated carbon and/or particulate filter media (ULPA or HEPA), located within a housing 218. The gases pathway 202 extends to atmosphere through the filter element 206 such that the filtered smoke and/or gases are vented to atmosphere at the second portion 210.

Smoke Venting Filters with Wicking Material

In some configurations, the humidity regulating element may include a wicking material or hydrophilic material to remove and/or reduce humidity from the gas path or absorb moisture.

Figure 16:
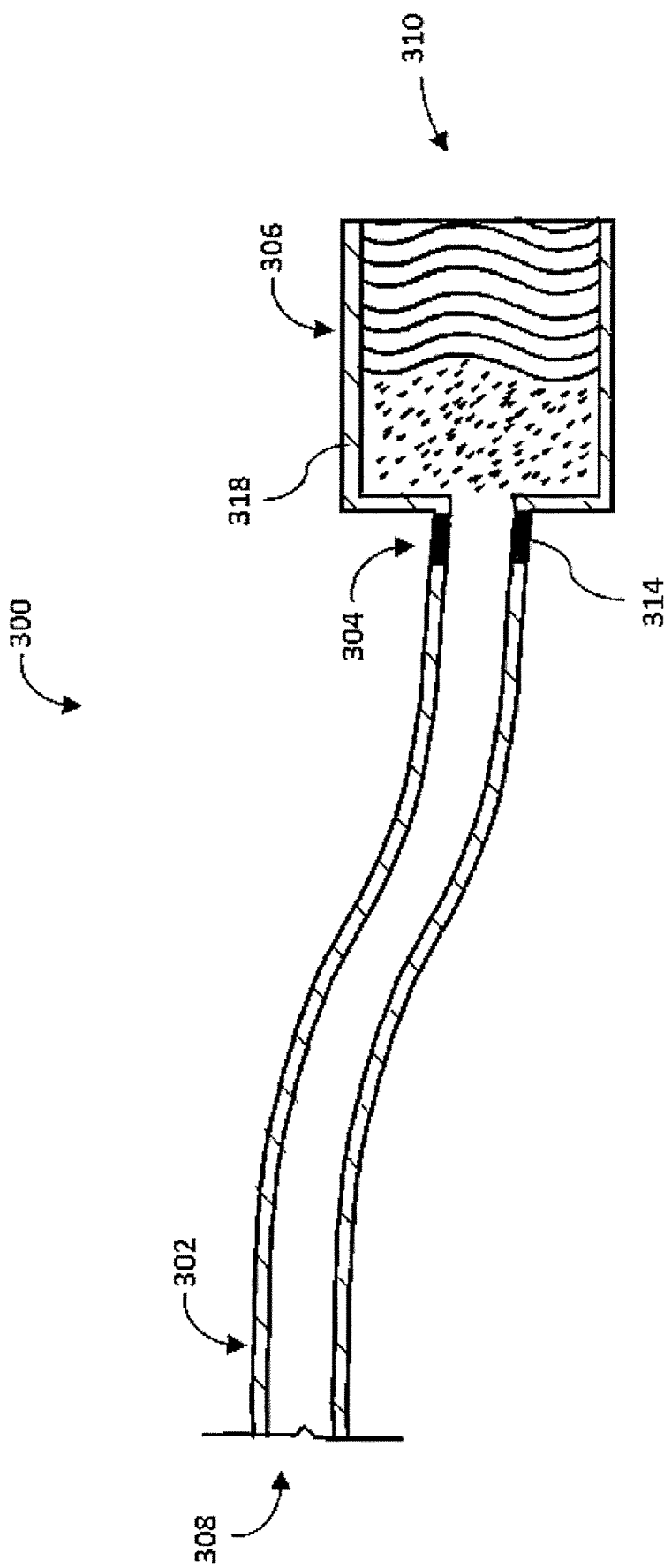
FIG. 16 illustrates a filter with a desiccant based humidity regulating element at a neck portion between a flexible tubing and a filter element.

As shown in FIG. 16, the smoke filter 300 may include a first portion 308 leading from a surgical site, a gases pathway 302 transporting smoke and/or gases exhausted from the surgical site, a humidity regulating element 304 located along the gases pathway 302, and a filter element 306 downstream of the humidity regulating element 304 such that the humidity regulating element 304 and the filter element 306 are in fluid communication with each other. At least a portion of the gases pathway 302 may be surrounded by a flexible plastic tubing or an inflexible tubing. The humidity regulating element 304 may include a wicking or hydrophilic material 314 upstream of the filter element 306 to absorb the humidity from the gas and/or absorb water/liquid condensed out of the vented gas. The wicking or hydrophilic material 314 may be positioned at a neck portion between the tubing and the filter element 306 or elsewhere between the surgical site and the filter element 306. The wicking or hydrophilic material 314 may be formed as a localized ring or toroidal element disposed along the gases pathway 302. The ring of wicking or hydrophilic material 314 may be coaxial with the tubing of the gases pathway 302. The filter element 306 may include one or more filter media 316, such as an activated carbon and/or particulate filter media (such as ULPA or HEPA), located within a housing 318. The gases pathway 302 extends to atmosphere through the filter element 306 such that the filtered smoke and/or gases are vented to atmosphere at the second portion 310.

Figure 17:
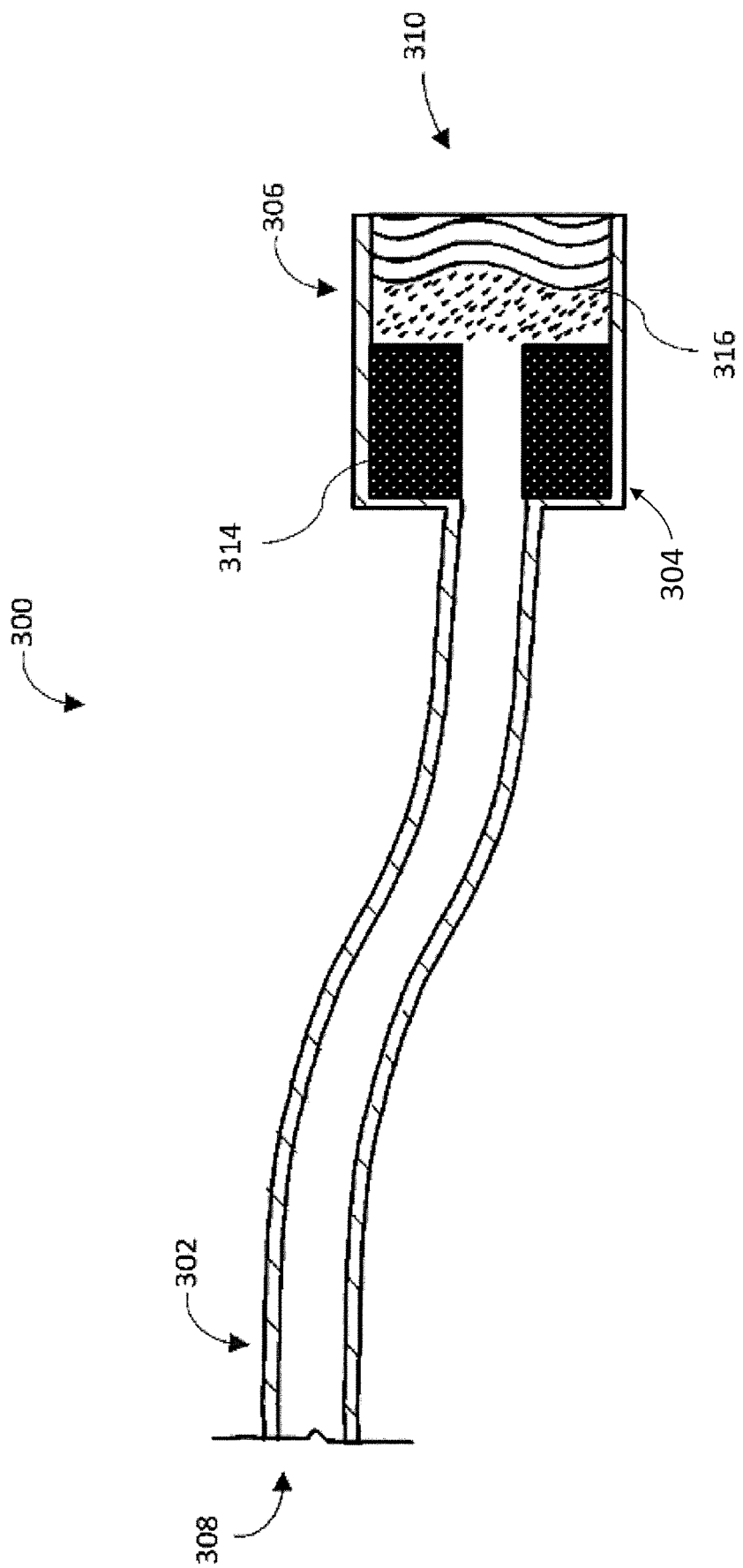
FIG. 17 illustrates a filter with a humidity regulating element having a wicking material within a filter element.

FIG. 17 illustrates another configuration of the smoke filter 300. The smoke filter 300 may include a first portion 308 leading from a surgical site, a gases pathway 302 transporting smoke and/or gases exhausted from the surgical site, a humidity regulating element 304 located along the gases pathway 302, and a filter element 306 in fluid communication with the humidity regulating element 304. At least a portion of the gases pathway 302 may be surrounded by a flexible plastic tubing or an inflexible tubing. The humidity regulating element 304 and the filter element 306 may be in a nested configuration. For example, the humidity regulating element 304 may be at least partially or fully housed within the tubing of the gases pathway 302 and/or the filter element 306. As shown, the filter element 306 may include one or more filter media 316, such as an activated carbon and/or particulate filter media (such as ULPA or HEPA), located within a housing 318. The humidity regulating element 304 may include a wicking material 314 located within the housing 318 and upstream from the filter media 316 to absorb moisture from the smoke and/or gases exhausted from the surgical site prior to the smoke and/or gases reaching the filter media 316. Viewed another way, the filter media 316 may be at least partially or entirely located within a housing of the humidity regulating element 304 and downstream from the wicking material 314. The gases pathway 302 extends to atmosphere through the filter element 306 such that the filtered smoke and/or gases are vented to atmosphere at the second portion 310.

Figure 18:
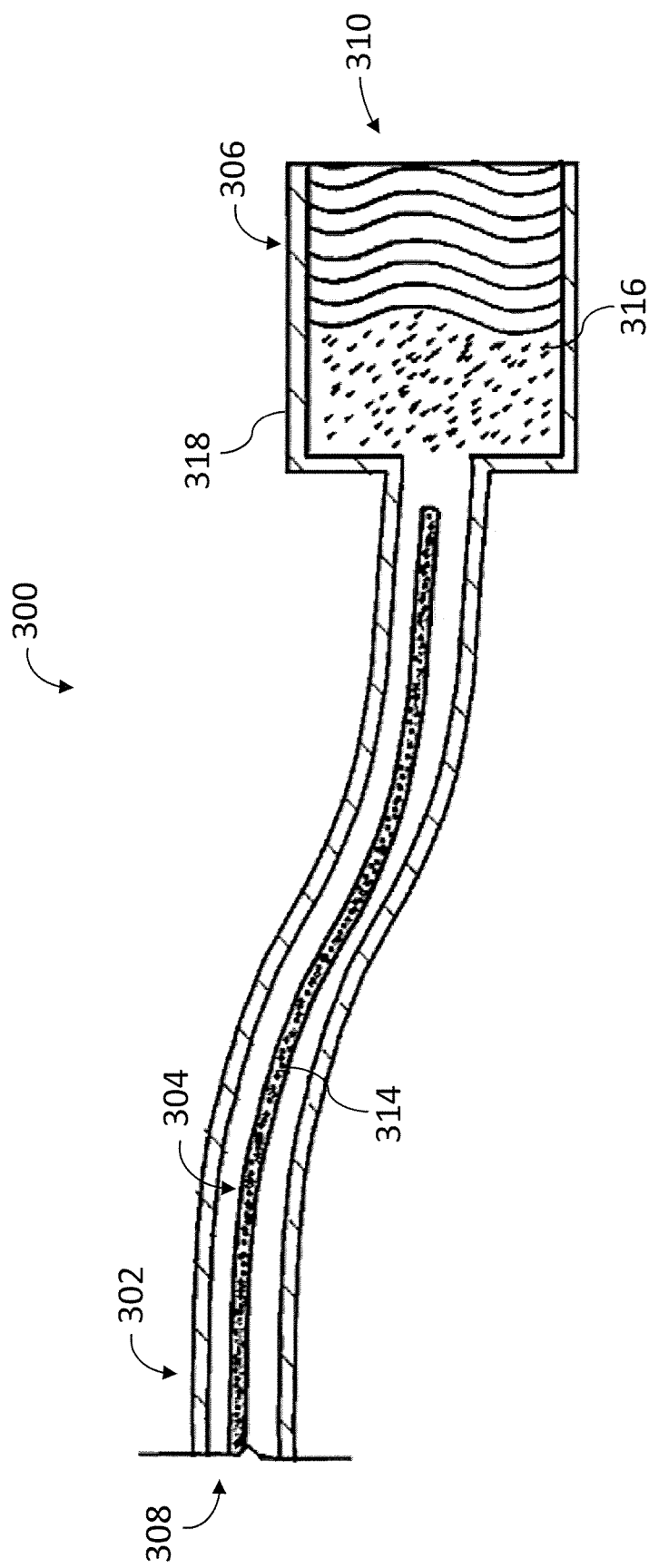
FIG. 18 illustrates a filter with a humidity regulating element having an internal rod with a wicking material that extends through a flexible tubing.

FIG. 18 illustrates yet another configuration of the smoke filter 300. The smoke filter 300 may include a first portion 308 leading from a surgical site, a gases pathway 302 transporting smoke and/or gases exhausted from the surgical site, a humidity regulating element 304 located along the gases pathway 302, and a filter element 306 in fluid communication with the humidity regulating element 304. At least a portion of the gases pathway 302 may be surrounded by a flexible plastic tubing or an inflexible tubing. The humidity regulating element 304 may include a wicking material 314 at least partially or fully housed within the tubing of the gases pathway 302 to absorb moisture from the smoke and/or gases exhausted from the surgical site prior to the smoke and/or gases reaching the downstream filter element 306. The wicking material 314 may be formed into a thin rod that extends through a lumen of the tubing. The filter element 306 may include one or more filter media 316, such as an activated carbon and/or particulate filter media (such as ULPA or HEPA), located within a housing 318. The gases pathway 302 extends to atmosphere through the filter element 306 such that the filtered smoke and/or gases are vented to atmosphere at the second portion 310.

Figure 19:
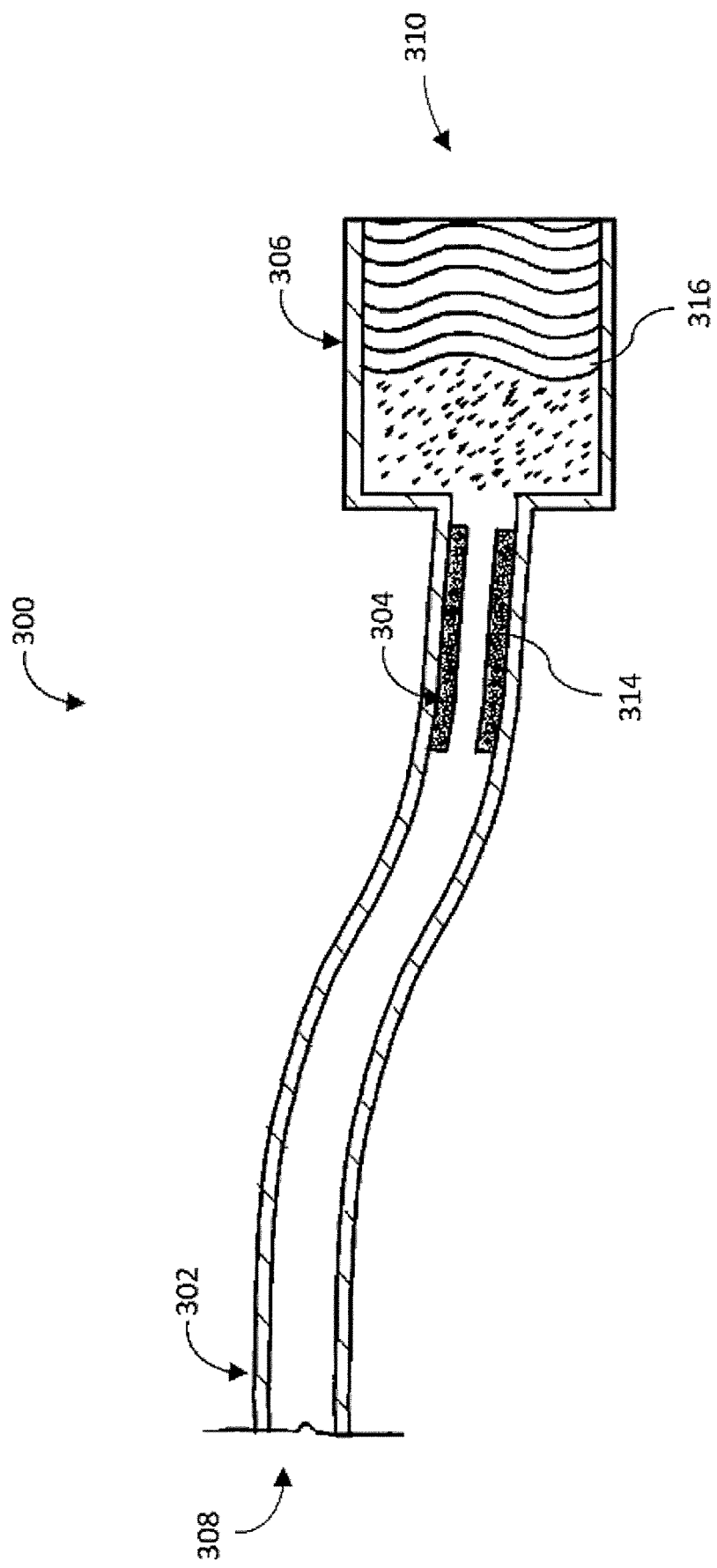
FIG. 19 illustrates a filter with a humidity regulating element having a wicking material within a flexible tubing.

FIG. 19 illustrates another configuration of the smoke filter 300. The smoke filter 300 may include a first portion 308 leading from a surgical site, a gases pathway 302 transporting smoke and/or gases exhausted from the surgical site, a humidity regulating element 304 located along the gases pathway 302, and a filter element 306 downstream of the humidity regulating element 304 such that the humidity regulating element 304 and the filter element 306 are in fluid communication with each other. At least a portion of the gases pathway 302 may be surrounded by a flexible plastic tubing or an inflexible tubing. The humidity regulating element 304 may include a wicking or hydrophilic material 314 upstream of the filter element 306 to absorb the humidity from the gas and/or absorb water/liquid condensed out of the vented gas. The wicking or hydrophilic material 314 may be positioned along an inner wall of the tubing, for example the wicking 314 may be formed as a localized ring or toroidal element disposed within the tubing. The ring of wicking or hydrophilic material 314 may be concentric and/or coaxial with the tubing of the gases pathway 302. The downstream filter element 306 may include one or more filter media 316, such as an activated carbon and/or particulate filter media (such as ULPA or HEPA), located within a housing 318. The gases pathway 302 extends to atmosphere through the filter element 306 such that the filtered smoke and/or gases are vented to atmosphere at the second portion 310.

Smoke Venting Filters for Condensing Humidity

In some configurations, the humidity regulating element may passively or actively cause condensation of the humidity. The smoke filters may include a feature for collecting the condensed water/liquid or allowing the condensed water/liquid to escape.

Figure 20:
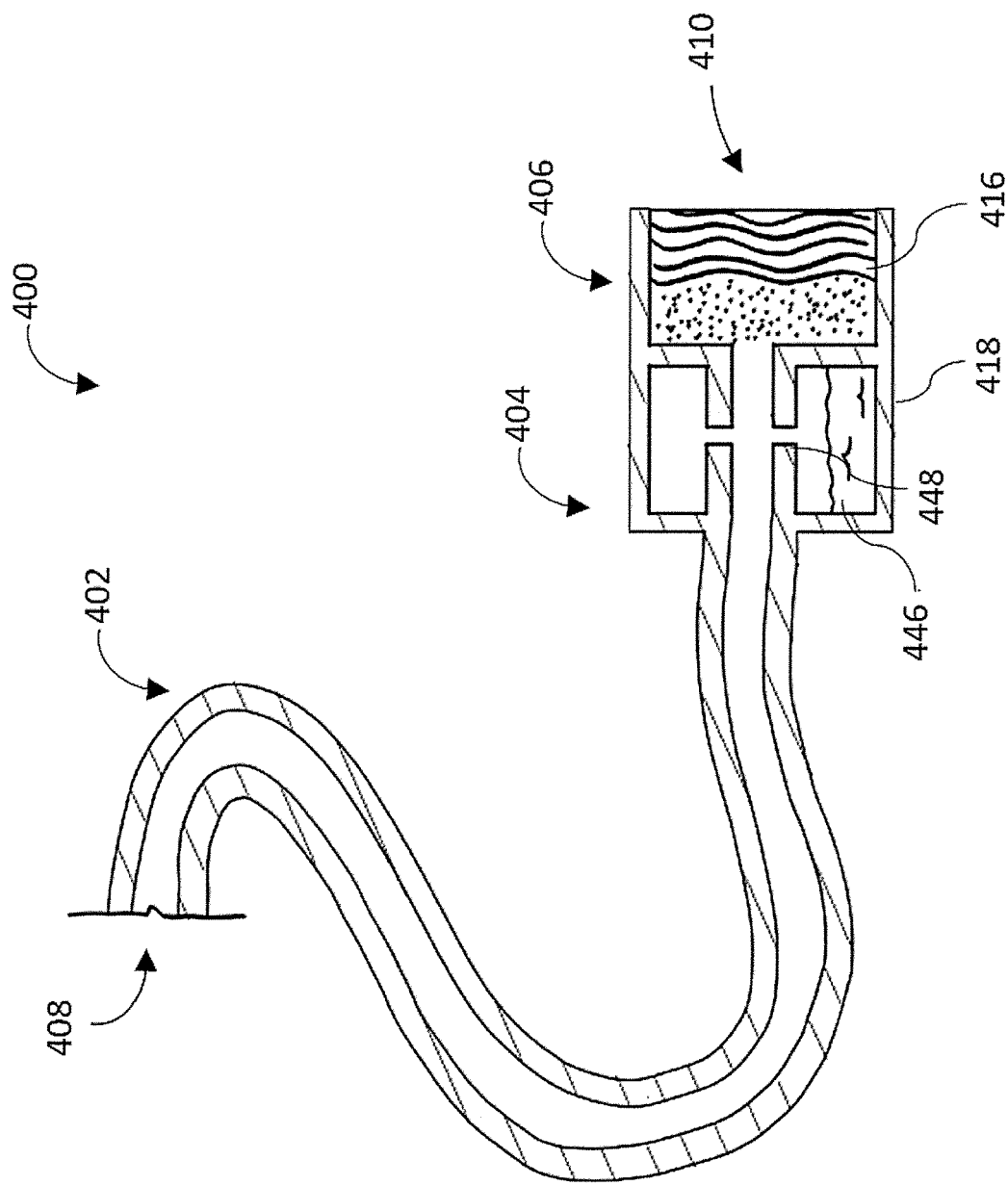
FIG. 20 illustrates a filter with a humidity regulating element having a reservoir.

FIG. 20 illustrates a configuration of the smoke filter 400 including a reservoir 446. The smoke filter 400 may include a first portion 408 leading from a surgical site, a gases pathway 402 transporting smoke and/or gases exhausted from the surgical site, a humidity regulating element 404 located along the gases pathway 402, and a filter element 406 in fluid communication with the humidity regulating element 404. At least a portion of the gases pathway 402 may be surrounded by a flexible plastic tubing or an inflexible tubing. The tubing may also form a part of the humidity regulating element 404. For example, the tubing may have sufficient length to naturally cool the gases over its length. The tubing having a lower temperature than upstream portions of the system. The humidity regulating element 404 may also include a reservoir 446 for collecting condensation formed from the cooled gas over the length of the tubing before it reaches the filter element 406. The reservoir 446 may extend at least partially or fully around the gases pathway 402. The tubing may include one or more outlets 448 to permit the condensed water/liquid to drip into the reservoir 446. As shown, the filter element 406 may include one or more filter media 416, such as an activated carbon and/or particulate filter media (such as ULPA or HEPA), located within a housing 418. The reservoir 446 of the humidity regulating element 404 may be located within the housing 418 and upstream from the filter media 416 to collect condensed moisture and to stop the condensed moisture from dripping into the filter media 416. Viewed another way, the filter media 416 may be at least partially or entirely located within a housing of the reservoir 446. The gases pathway 402 extends to atmosphere through the filter element 406 such that the filtered smoke and/or gases are vented to atmosphere at the second portion 410.

Figure 21:
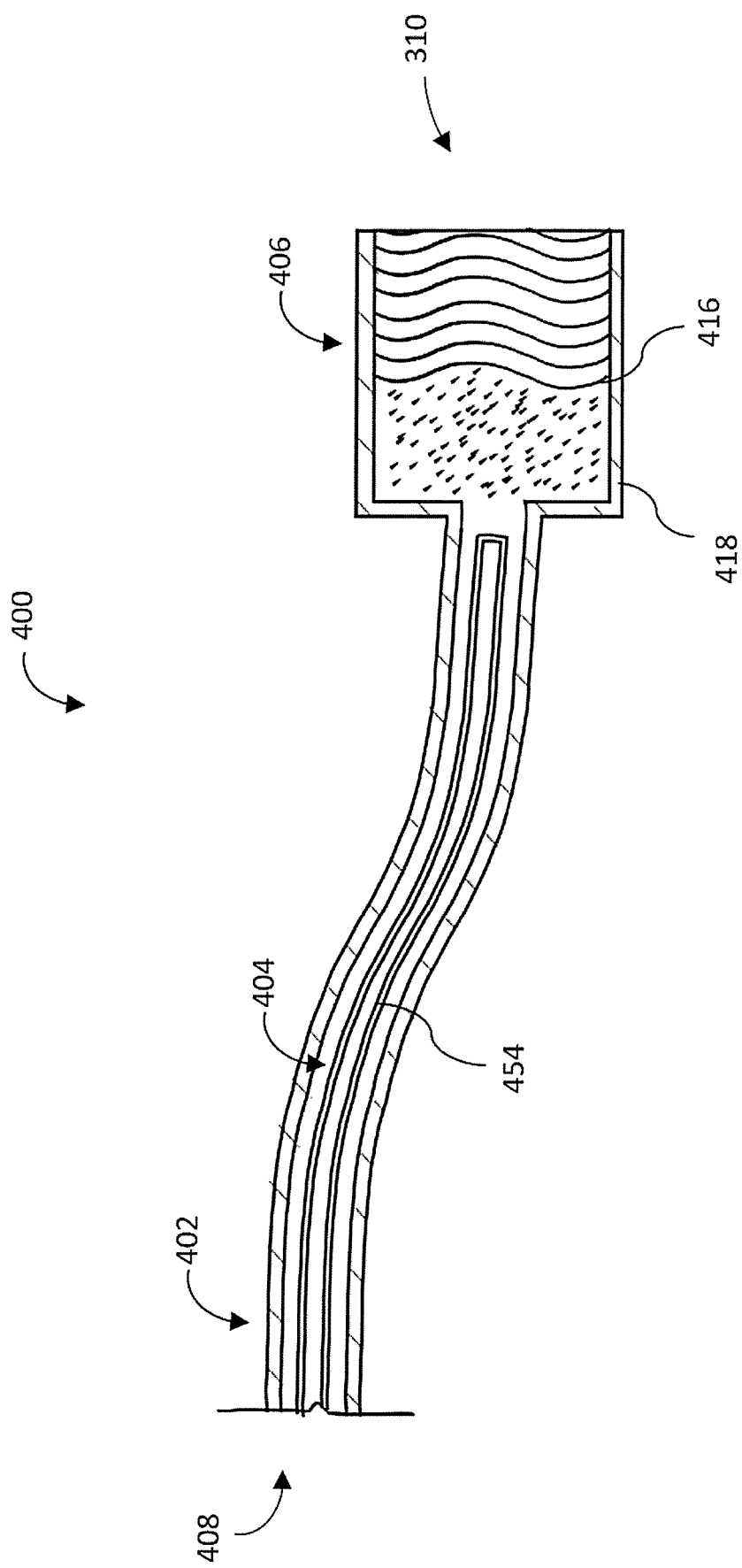
FIG. 21 illustrates a filter with a humidity regulating element having a reservoir disposed within a flexible tubing.

FIG. 21 illustrates another configuration of a smoke filter 400 having a reservoir 454. The smoke filter 400 may include a first portion 408 leading from a surgical site, a gases pathway 402 transporting smoke and/or gases exhausted from the surgical site, a humidity regulating element 404 located along the gases pathway 402, and a filter element 406 in fluid communication with the humidity regulating element 404. At least a portion of the gases pathway 402 may be surrounded by a flexible plastic tubing or an inflexible tubing. The tubing may also form a part of the humidity regulating element 404. The tubing may have sufficient length to naturally cool the gases over its length. The tubing may have a lower temperature than upstream portions of the system. The humidity regulating element 404 may also include a reservoir 454 disposed within the tubing. The reservoir 454 may include a permeable membrane with an internal lumen to store the condensed moisture before it reaches the downstream filter element 406. The permeable membrane allows vapor and/or liquid moisture to pass through the membrane. As shown, the filter element 406 may include one or more filter media 416, such as an activated carbon and/or particulate filter media (such as ULPA or HEPA), located within a housing 418. The gases pathway 402 extends to atmosphere through the filter element 406 such that the filtered smoke and/or gases are vented to atmosphere at the second portion 410.

Figure 22:
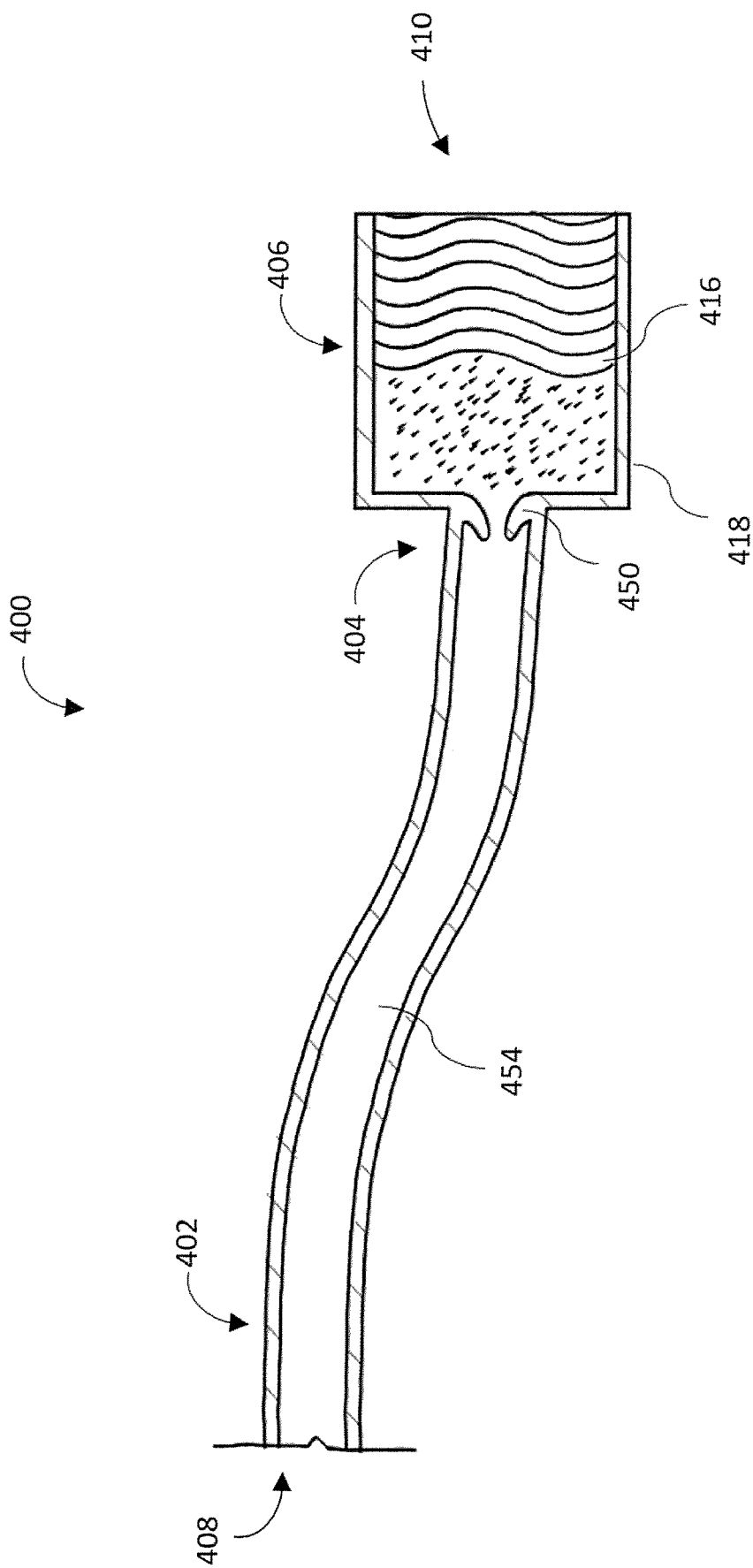
FIG. 22 illustrates a filter with a humidity regulating element having a fluid, e.g., water trap.

FIG. 22 illustrates yet another configuration of a smoke filter 400 having a fluid, e.g., water trap 450. The smoke filter 400 may include a first portion 408 leading from a surgical site, a gases pathway 402 transporting smoke and/or gases exhausted from the surgical site, a humidity regulating element 404 located along the gases pathway 402, and a filter element 406 in fluid communication with the humidity regulating element 404. At least a portion of the gases pathway 402 may be surrounded by a flexible plastic tubing or an inflexible tubing. The tubing may also form a part of the humidity regulating element 404. The tubing may have sufficient length to naturally cool the gases over its length. The humidity regulating element 404 may also include a fluid, e.g., water trap 450 disposed at the neck between the tubing and the filter element 406. The fluid, e.g., water trap 450 prevents condensed moisture from reaching the filter element 406. The filter element 406 may include one or more filter media 416, such as an activated carbon and/or particulate filter media (such as ULPA or HEPA), located within a housing 418. The gases pathway 402 extends to atmosphere through the filter element 406 such that the filtered smoke and/or gases are vented to atmosphere at the second portion 410.

Figure 23:
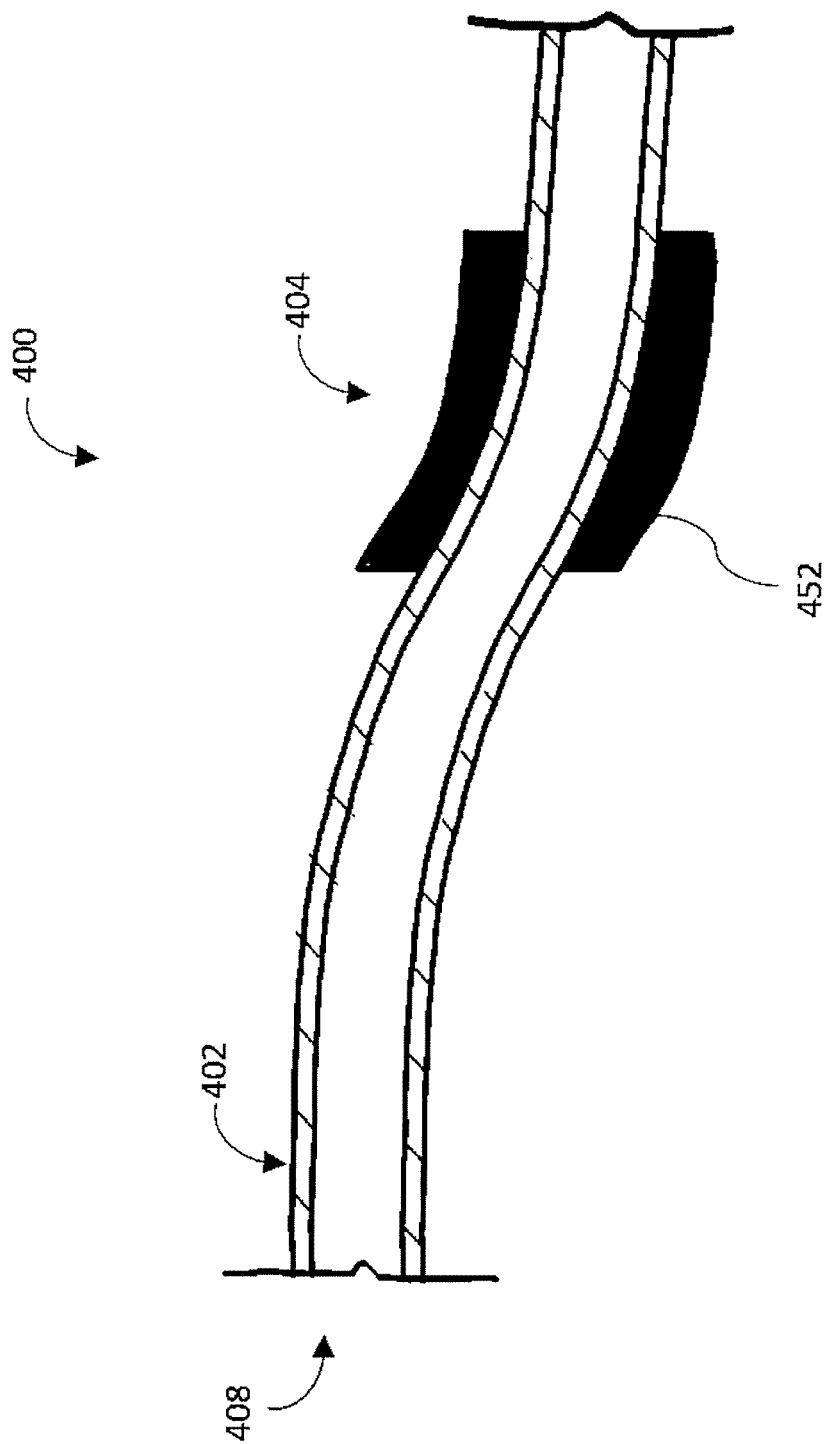
FIG. 23 illustrates a filter having a passive heatsink.

FIG. 23 illustrates another configuration of the smoke filter 400. The smoke filter 400 may include a first portion 408 leading from a surgical site, a gases pathway 402 transporting smoke and/or gases exhausted from the surgical site, a humidity regulating element 404 located along the gases pathway 402, and a filter element (not shown) in fluid communication with the humidity regulating element 404. At least a portion of the gases pathway 402 may be surrounded by a flexible plastic tubing or an inflexible tubing. The humidity regulating element 404 may include a passive heatsink 452 that naturally cools the gas locally to force condensation. The passive heatsink 452 may include a thermally conductive material such as metal. As shown, the passive heatsink 452 may be disposed around the tubing of the gases pathway 402 but may be located elsewhere such as in line with the tubing or within the tubing. The humidity regulating element 404 may also include a feature for collecting the condensed moisture before it reaches the filter element, such as a reservoir, trap, permeable wall, wicking material, desiccant material, or other feature described above. Similar to the previously described smoke filters 400, the filter element may be positioned downstream of the humidity regulating element 404 and may include one or more filter media, such as an activated carbon and/or particulate filter media (such as ULPA or HEPA), located within a housing. The gases pathway 402 extends to atmosphere through the filter element such that the filtered smoke and/or gases are vented to atmosphere at the second portion.

Figure 24A:
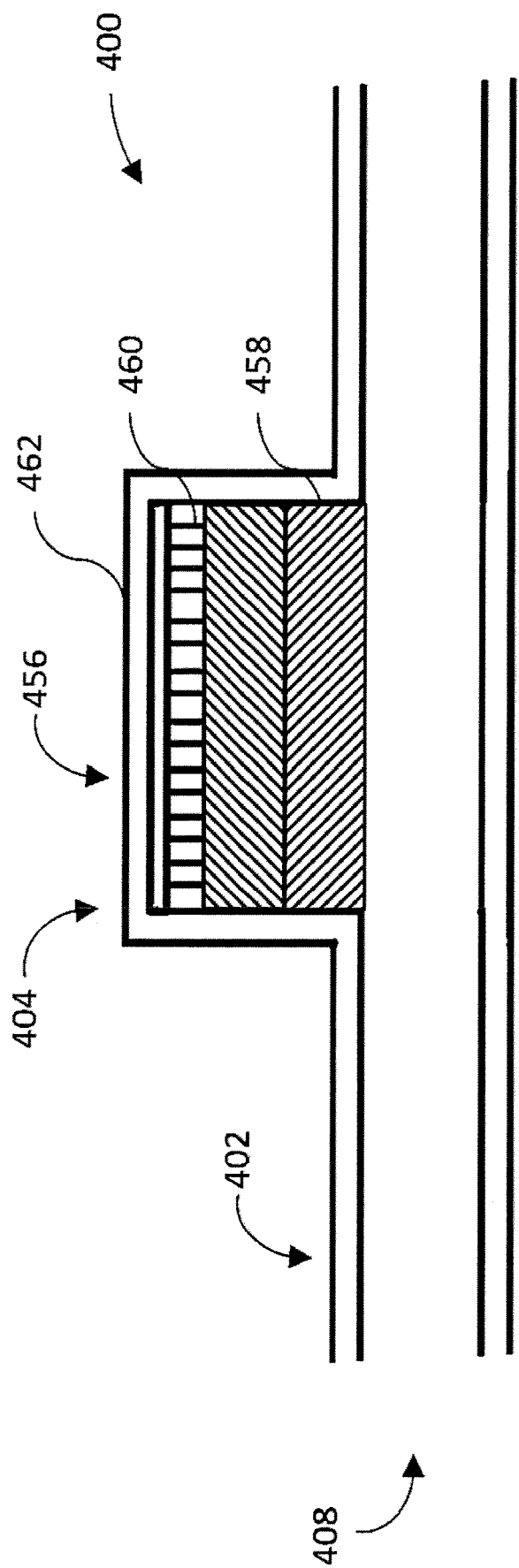
FIGS. 24A and 24B illustrate a filter having a cooling mechanism.
Figure 24B:
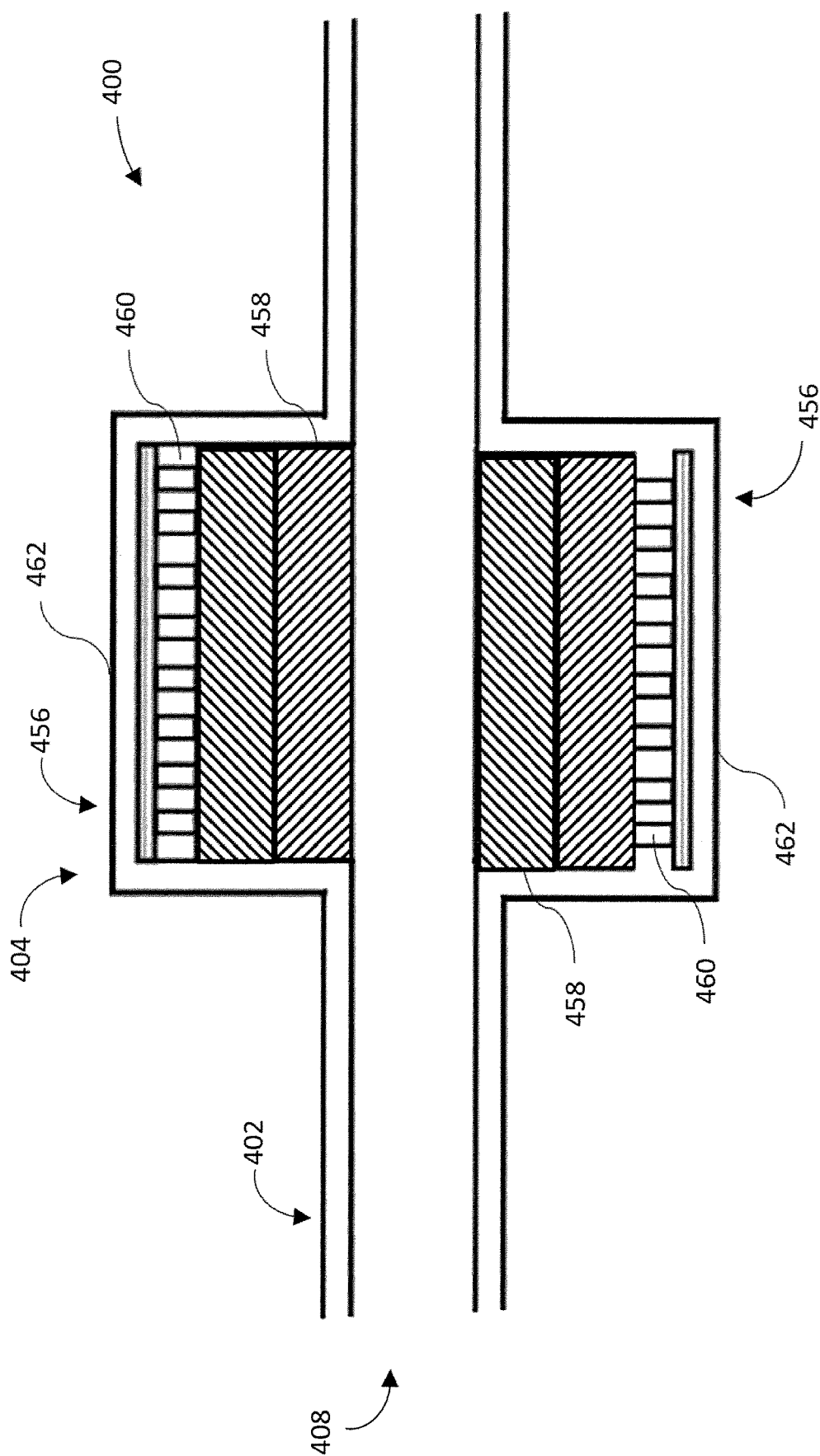

FIGS. 24A and 24B illustrates another configuration of the smoke filter 400 having a cooling mechanism 456 that may partially (FIG. 24A) or fully (FIG. 24B) surround the gases pathway 402. The smoke filter 400 may include a first portion 408 leading from a surgical site, a gases pathway 402 transporting smoke and/or gases exhausted from the surgical site, a humidity regulating element 404 located along the gases pathway 402, and a filter element (not shown) in fluid communication with the humidity regulating element 404. At least a portion of the gases pathway 402 may be surrounded by a flexible plastic tubing or an inflexible tubing. The humidity regulating element 404 may include a cooling mechanism 456 disposed along the tubing. For example, the cooling mechanism 456 may include a Peltier cooler 458 to cool down the vented gas to force condensation and a cooling element 460 on a hot side of the Peltier cooler 458 to improve the cooling effect. The cooling element 460 may include a heat sink, fan, and/or other active cooling element to improve cooling. The cooling mechanism 456 may also include an insulation layer 462 to prevent the outer surface from getting too hot. The cooling mechanism 456 may be powered externally or through a battery. The humidity regulating element 404 may also include a feature for collecting the condensed moisture before it reaches the filter element, such as a reservoir, trap, permeable wall, wicking material, desiccant material, or other feature described above. Similar to the previously described smoke filters 400, the filter element may be positioned downstream of the humidity regulating element 404 and may include one or more filter media, such as an activated carbon and/or particulate filter media (such as ULPA or HEPA), located within a housing. The gases pathway 402 extends to atmosphere through the filter element such that the filtered smoke and/or gases are vented to atmosphere at the second portion.

Figure 25:
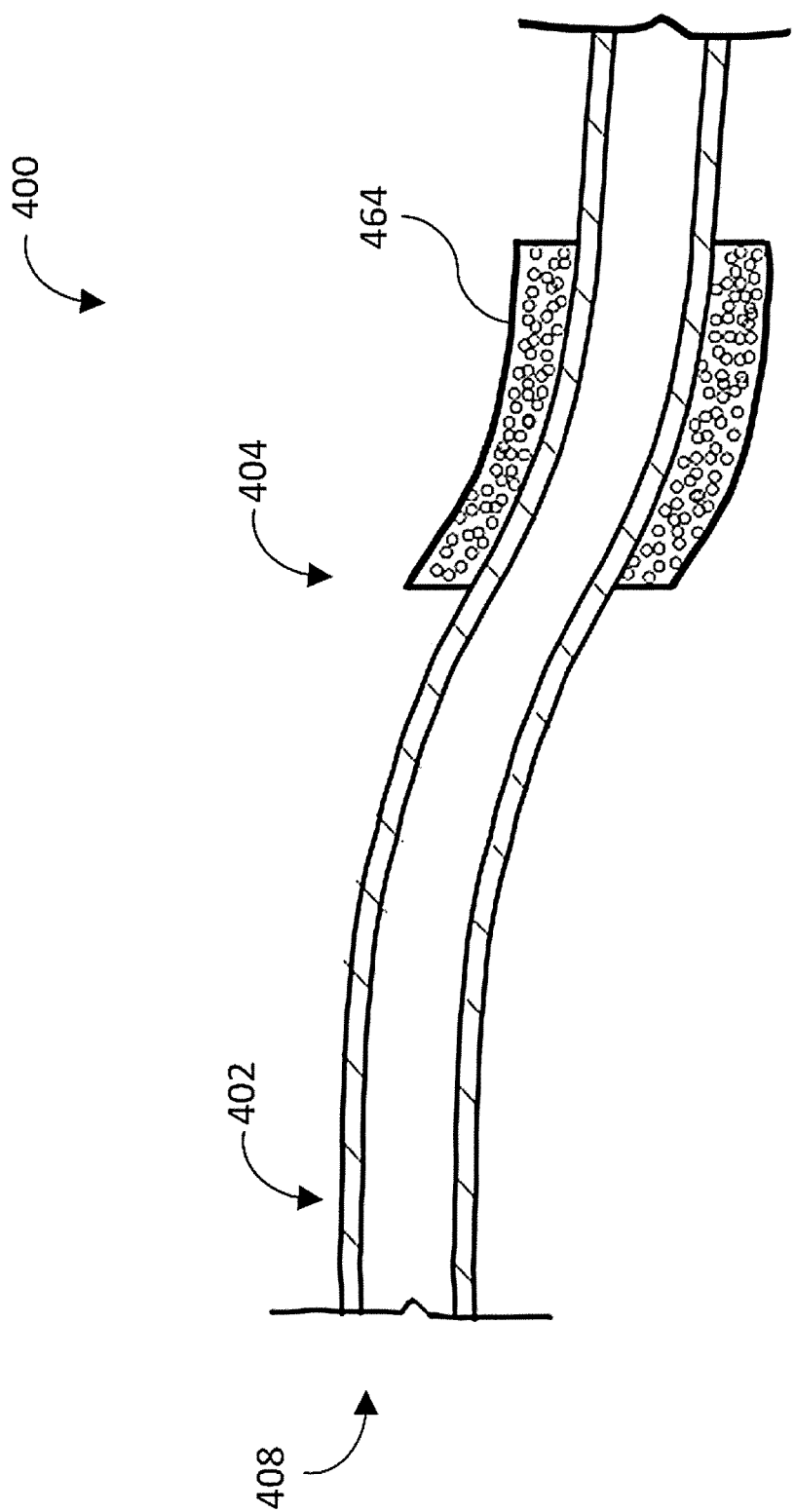
FIG. 25 illustrates a filter having a chemical cooler.

FIG. 25 illustrates another configuration of the smoke filter 400. The smoke filter 400 may include a first portion 408 leading from a surgical site, a gases pathway 402 transporting smoke and/or gases exhausted from the surgical site, a humidity regulating element 404 located along the gases pathway 402, and a filter element (not shown) in fluid communication with the humidity regulating element 404. At least a portion of the gases pathway 402 may be surrounded by a flexible plastic tubing or an inflexible tubing. The humidity regulating element 404 may include a chemical cooler 464 to cool the tubing along a certain length. The chemical cooler 464 could be activated by the mixing of compounds, for example by shaking or breaking of a barrier separating the compounds. As shown, the chemical cooler 464 may be a sleeve at least partially or fully disposed around the tubing of the gases pathway 402 but may be located elsewhere such as in line with the tubing or within the tubing. The humidity regulating element 404 may also include a feature for collecting the condensed moisture before it reaches the filter element, such as a reservoir, trap, permeable wall, wicking material, desiccant material, or other feature described above. Similar to the previously described smoke filters 400, the filter element may be positioned downstream of the humidity regulating element 404 and may include one or more filter media, such as an activated carbon and/or particulate filter media (such as ULPA or HEPA), located within a housing. The gases pathway 402 extends to atmosphere through the filter element such that the filtered smoke and/or gases are vented to atmosphere at the second portion.

Smoke Venting Filters with Heating Elements

In some configurations, the humidity regulating element includes a heating element to maintain the gas temperature above its dew point temperature and prevent condensation.

Figure 26:
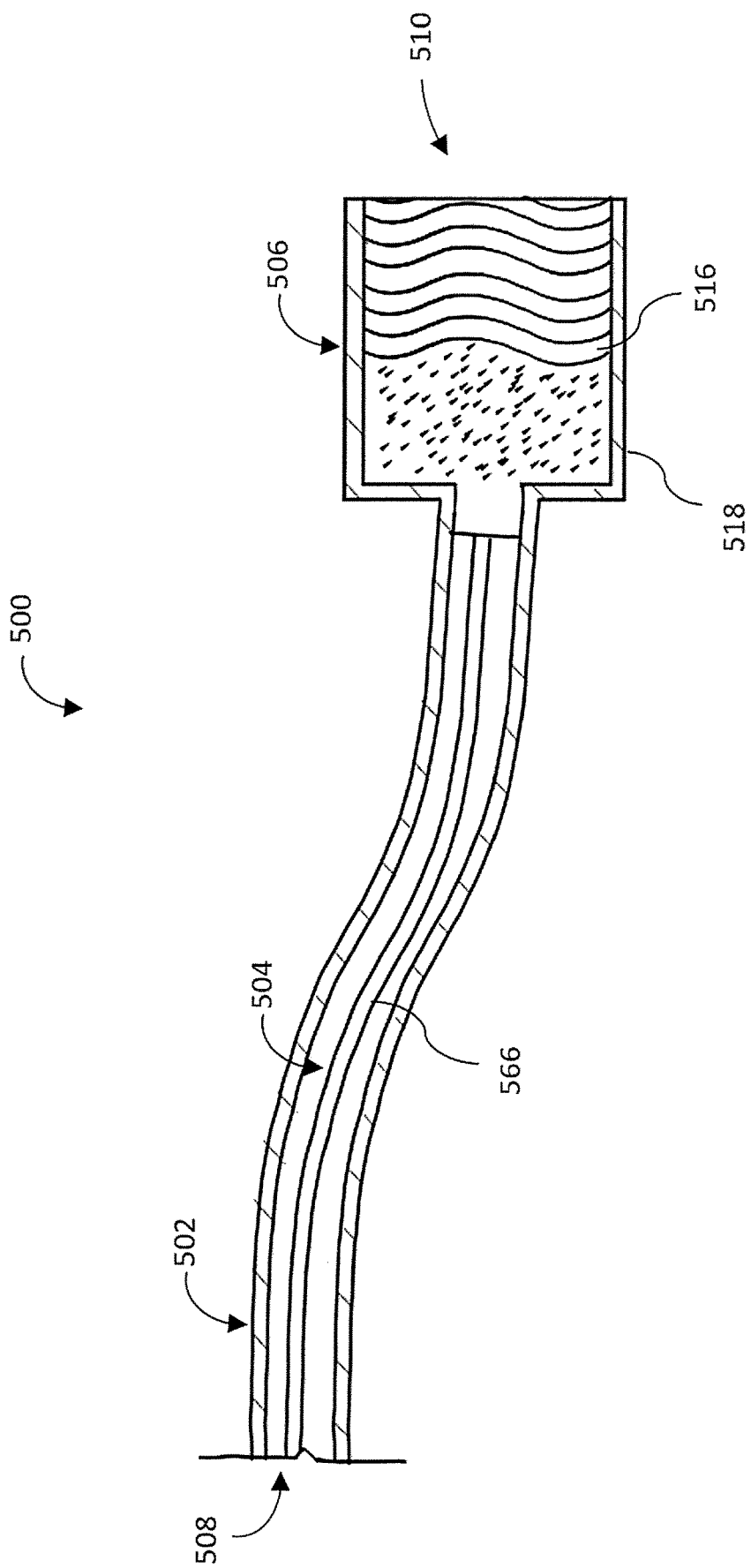
FIG. 26 illustrates a filter with a heating wire extending through a flexible tubing.

As shown in FIG. 26, the smoke filter 500 may include a first portion 508 leading from a surgical site, a gases pathway 502 transporting smoke and/or gases exhausted from the surgical site, a humidity regulating element 504 located along the gases pathway 502, and a filter element 506 downstream of the humidity regulating element 504 such that the humidity regulating element 504 and the filter element 506 are in fluid communication with each other. At least a portion of the gases pathway 502 may be surrounded by a flexible plastic tubing or an inflexible tubing. The humidity regulating element 504 may include a heating wire 566 to heat and maintain the gases above the dew point temperature so that no condensation occurs along the tubing or at the filter element 506. The heating wire 566 could be limited to the tubing or also extend into or around the filter element 506. The heating wire 566 may be powered externally or using a battery. The filter element 506 may include one or more filter media 516, such as an activated carbon and/or particulate filter media (such as ULPA or HEPA), located within a housing 518. The gases pathway 502 extends to atmosphere through the filter element 506 such that the filtered smoke and/or gases are vented to atmosphere at the second portion 510.

Figure 27:
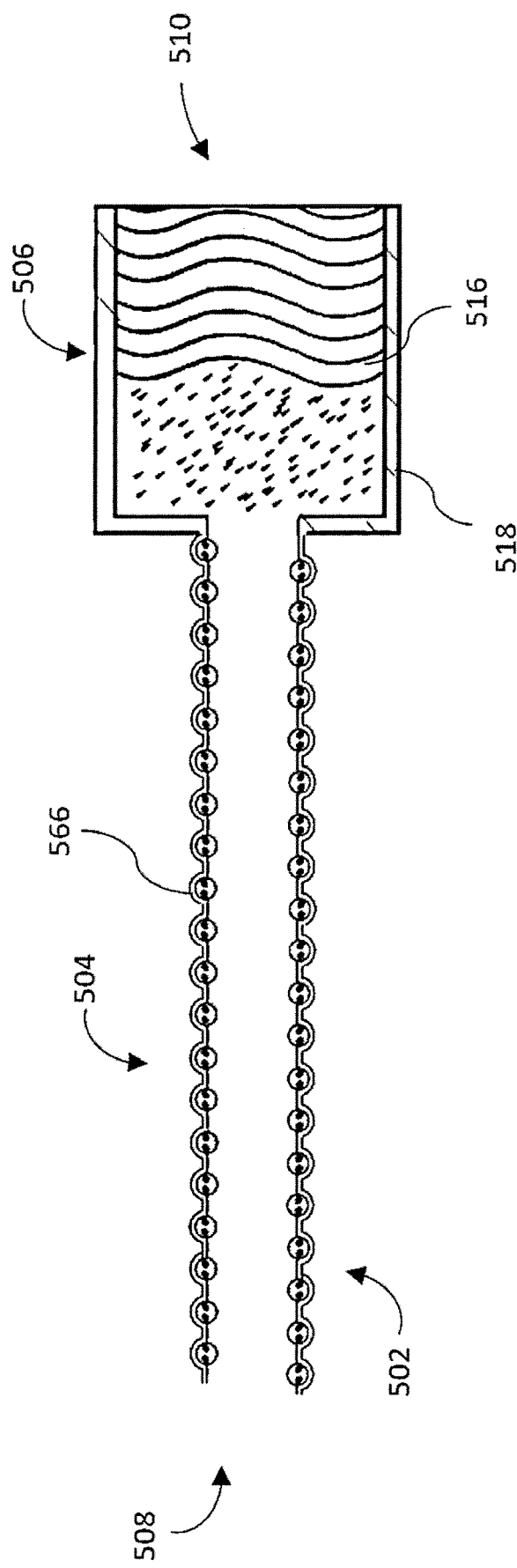
FIG. 27 illustrates a filter with a heating wire integrated into a flexible tubing.

Although FIG. 26 illustrates the heating wire 566 disposed within the tubing and/or filter element 506, the heating wire 566 may alternatively be external to, for example wrapped around or formed into, the tubing and/or the filter element 506. For example, FIG. 27 illustrates a humidity regulating element 504 having a spiral wound tube with an embedded heater wire 566. The heater wire 566 heats and maintains the gases above the dew point temperature so that no condensation occurs along the tubing or at the downstream filter element 506. The heater wire 566 may be over molded in plastic bead or may be tightly or loosely positioned over a tube or in a tube, for example between inner and outer layers of the tube. The downstream filter element 506 may include one or more filter media 516, such as an activated carbon and/or particulate filter media (such as ULPA or HEPA), located within a housing 518. The gases pathway 502 extends to atmosphere through the filter element 506 such that the filtered smoke and/or gases are vented to atmosphere at the second portion 510.

Figure 28:
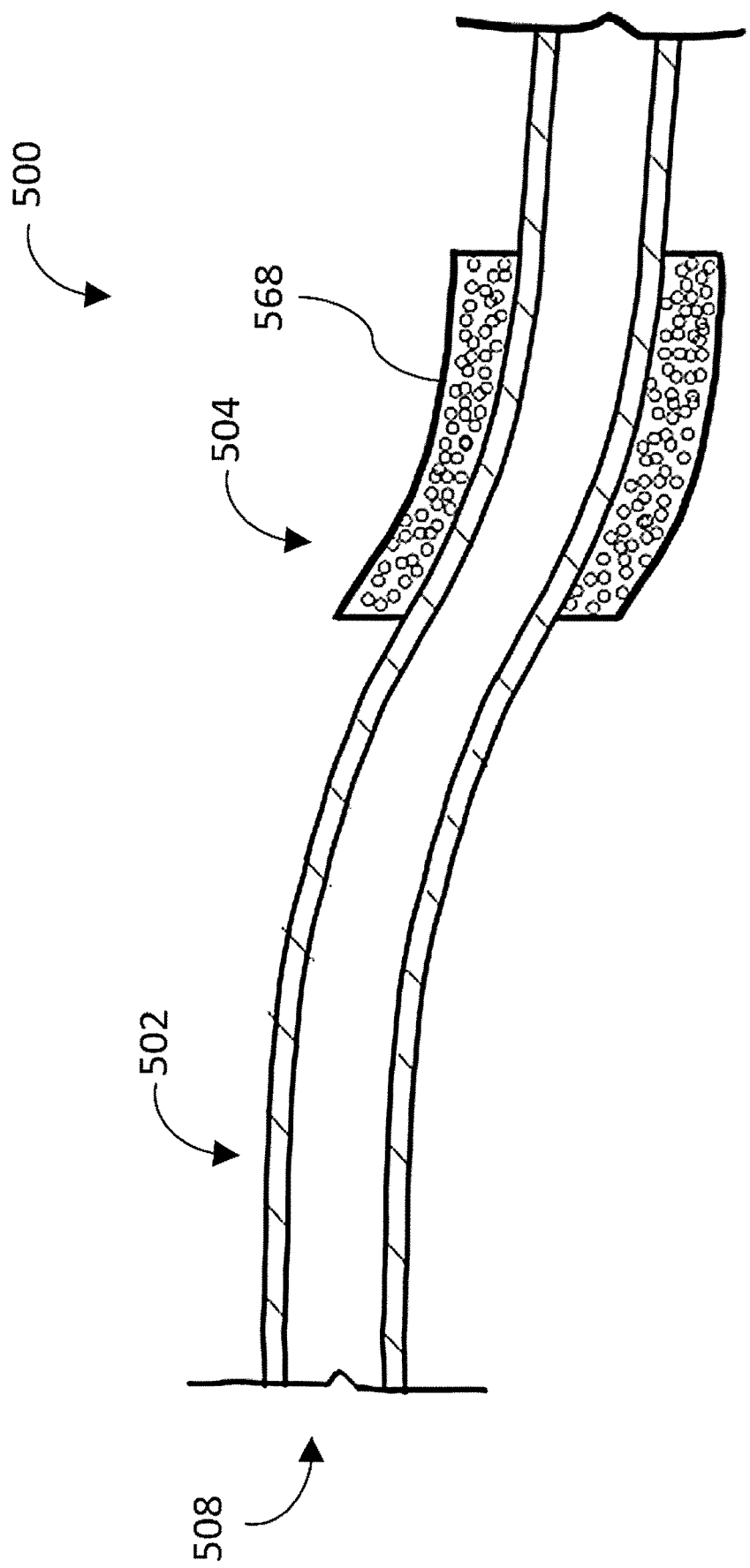
FIG. 28 illustrates a filter having a chemical heater.

FIG. 28 illustrates another configuration of the smoke filter 500 including a chemical heater 568. The smoke filter 500 may include a first portion 508 leading from a surgical site, a gases pathway 502 transporting smoke and/or gases exhausted from the surgical site, a humidity regulating element 504 located along the gases pathway 502, and a filter element (not shown) in fluid communication with the humidity regulating element 504. At least a portion of the gases pathway 502 may be surrounded by a flexible plastic tubing or an inflexible tubing. The humidity regulating element 504 may include a chemical heater 568 to heat and maintain the gases above the dew point temperature to reduce saturation and prevent condensation along the tubing or at the downstream filter element 506. The chemical heater 568 may be activated by the mixing of compounds, for example by shaking or breaking a barrier separating the compounds. As shown, the chemical heater 568 may be formed as a sleeve at least partially or fully disposed around the tubing of the gases pathway 502 but may be located elsewhere such as in line with the tubing or within the tubing. Similar to the previously described smoke filters 500, the filter element may be positioned downstream of the humidity regulating element 504 and may include one or more filter media, such as an activated carbon and/or particulate filter media (such as ULPA or HEPA), located within a housing. The gases pathway 502 extends to atmosphere through the filter element such that the filtered smoke and/or gases are vented to atmosphere at the second portion.

Smoke Venting Filters with Permeable Tubing

In some configurations, the humidity regulating element include a water permeable membrane tubing to allow vapor and/or liquid moisture to escape.

Figure 29:
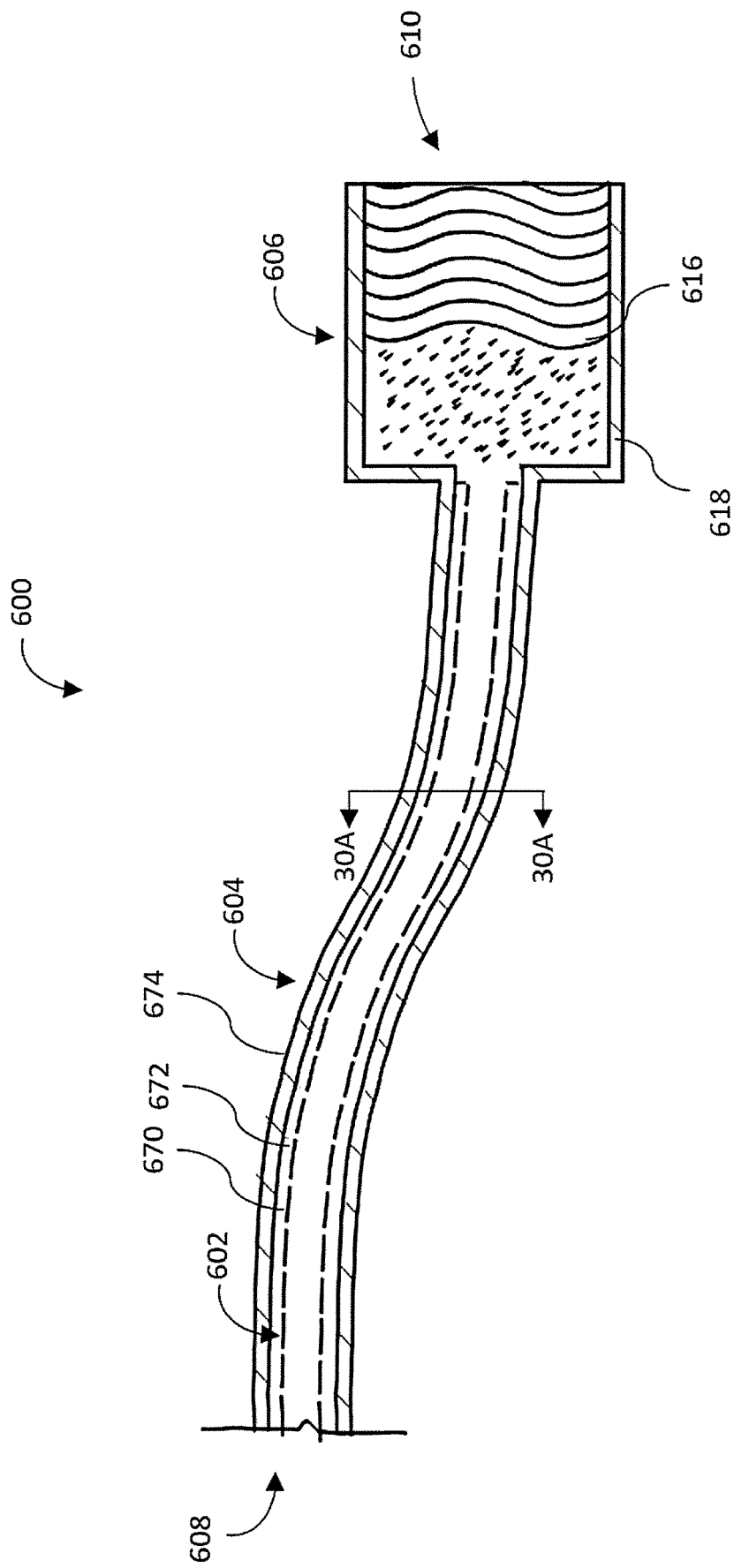
FIG. 29 illustrates a filter having a permeable inner tube.

As shown in FIG. 29, the smoke filter 600 may include a first portion 608 leading from a surgical site, a gases pathway 602 transporting smoke and/or gases exhausted from the surgical site, a humidity regulating element 604 located along the gases pathway 602, and a filter element 606 downstream of the humidity regulating element 604 such that the humidity regulating element 604 and the filter element 606 are in fluid communication with each other. At least a portion of the gases pathway 602 may be surrounded by a flexible plastic tubing or an inflexible tubing. The humidity regulating element 604 may include an inner tube 670 disposed within an outer wall 674 and an outer lumen 672 therebetween. The inner tube 670 may include a membrane or breathable material that is vapor and/or liquid moisture permeable. For example, the membrane or breathable material may be water vapor permeable but does not allow the passage of liquid water. The inner tube 670 allows humidity to escape due to the humidity gradient between the outer lumen 672 and the humid air coming out of the pneumoperitoneum. The outer lumen 672 may be used to store water/liquid absorbed through the inner tube 670. The outer wall 674 may include a hydrophilic material to keep absorbed moisture outside of the inner tube 670. The filter element 606 may include one or more filter media 616, such as an activated carbon and/or particulate filter media (such as ULPA or HEPA), located within a housing 618. The gases pathway 602 extends to atmosphere through the filter element 606 such that the filtered smoke and/or gases are vented to atmosphere at the second portion 610.

The membrane allows water vapor to pass through the wall of the membrane. For example, the membrane may be formed of a foamed breathable material. The breathable material may be a blend of polymers or a composite material of multiple polymers. The foamed breathable material includes a plurality of voids in the breathable material. The breathable material may comprise a thermoplastic elastomer with a polyether soft segment. The breathable foamed material can comprise a copolyester thermoplastic elastomer with a polyether soft segment.

Alternatively, the breathable membrane is formed from a breathable material that is water vapor and/or liquid permeable. For example, the breathable membrane may allow the passage of water vapor without allowing the passage of liquid water. The breathable material may comprise an activated perflourinated polymer having extreme hydrophobic properties. Alternatively, the breathable material comprises hydrophilic thermoplastics such as for example hydrophilic polyester block copolymer. In a further alternative, the breathable material may comprise woven treated fabrics exhibiting breathable characteristics.

Figure 30A:
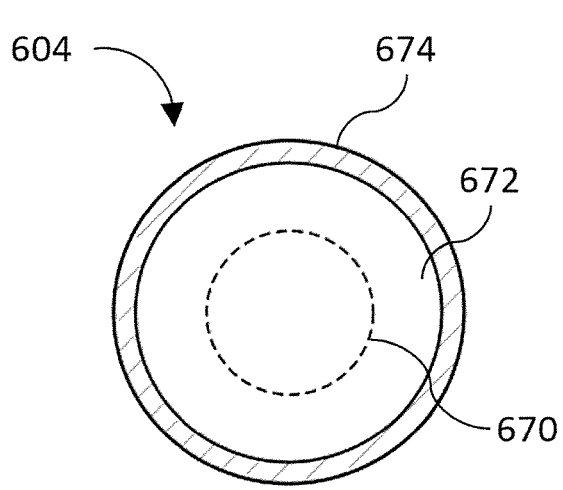
FIGS. 30A-30E illustrate cross-sections of different filters having a permeable inner tube.
Figure 30B:
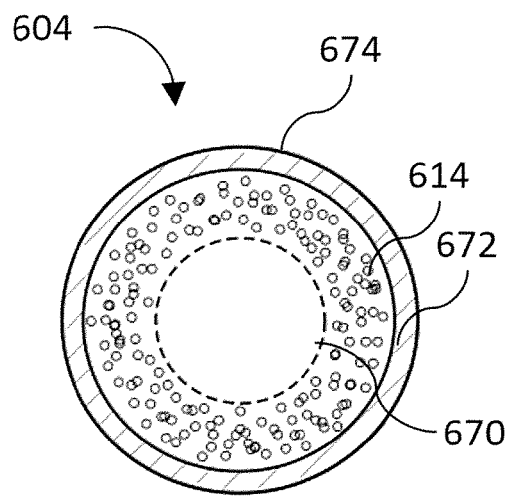
Figure 30C:
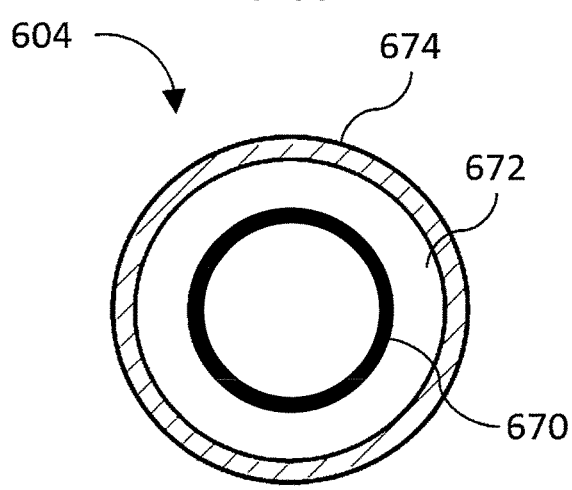
Figure 30D:
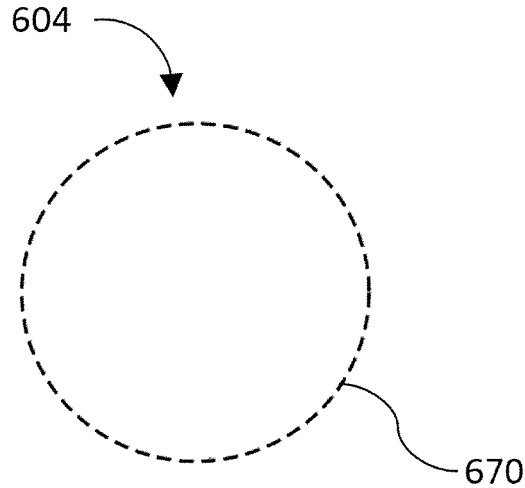
Figure 30E:
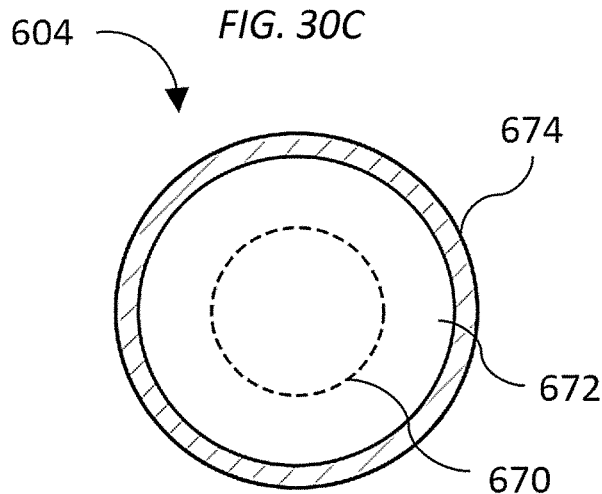

FIGS. 30A-30E illustrate various cross-sections of permeable membranes for removing vapor and/or liquid moisture before the gas reaches the filter element 606. FIG. 30A illustrates a cross-section of the humidity regulating element 604 shown in FIG. 29 along line 30A-30A. The humidity regulating element 604 includes an inner permeable wall 670 and a solid outer wall 674 with an outer lumen 672 disposed therebetween to hold condensed moisture. FIG. 30B illustrates a humidity regulating element 604 with an inner permeable wall 670 and a solid outer wall 674 with a desiccant or water wicking material 614 disposed within the outer lumen 672 to increase the transfer of vapor and/or liquid moisture through the inner permeable wall 670. FIG. 30C illustrates a humidity regulating element 604 with an inner tube 670, an outer tube 674, and an outer lumen 672 disposed therebetween. The inner tube 670 may have an ionic exchange membrane to extract moisture from gases passing through the inner lumen of the inner tube 670. FIG. 30D illustrates a humidity regulating element 604 with an inner tube 670 having a permeable membrane. FIG. 30E illustrates a humidity regulating element 604 including an inner permeable tube 670, an outer wall 674, and an outer lumen 672 disposed therebetween. The humidity regulating element 604 may include an airflow supplied along the outer lumen 672 to carry away vapor and/or liquid moisture and increase the transfer potential across the inner permeable tube 670.

Filter Elements for Smoke Venting Filters

As described above, the filter element may include one or more filter media, such as an activated carbon and/or particulate filter media (such as ULPA or HEPA), located within a housing. The gases pathway 602 extends to atmosphere through the filter element 606 such that the filtered smoke and/or gases are vented to atmosphere at the second portion 610. However, other filter element configurations are possible. The filter element configurations described below may be used alone or in combination with the other smoke filters described herein.

Figure 31:
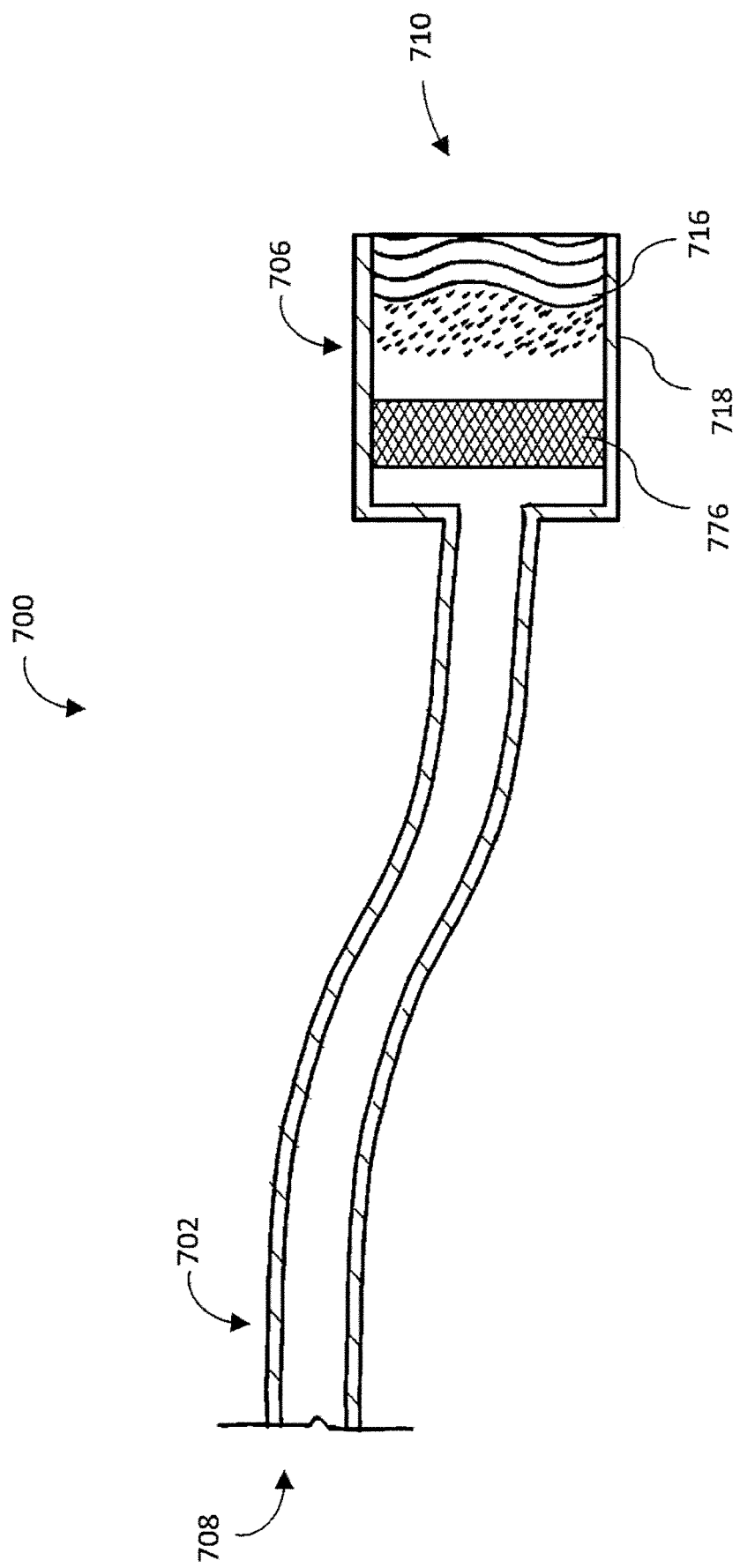
FIG. 31 illustrates a filter having an additional filter stage.
Figure 32:
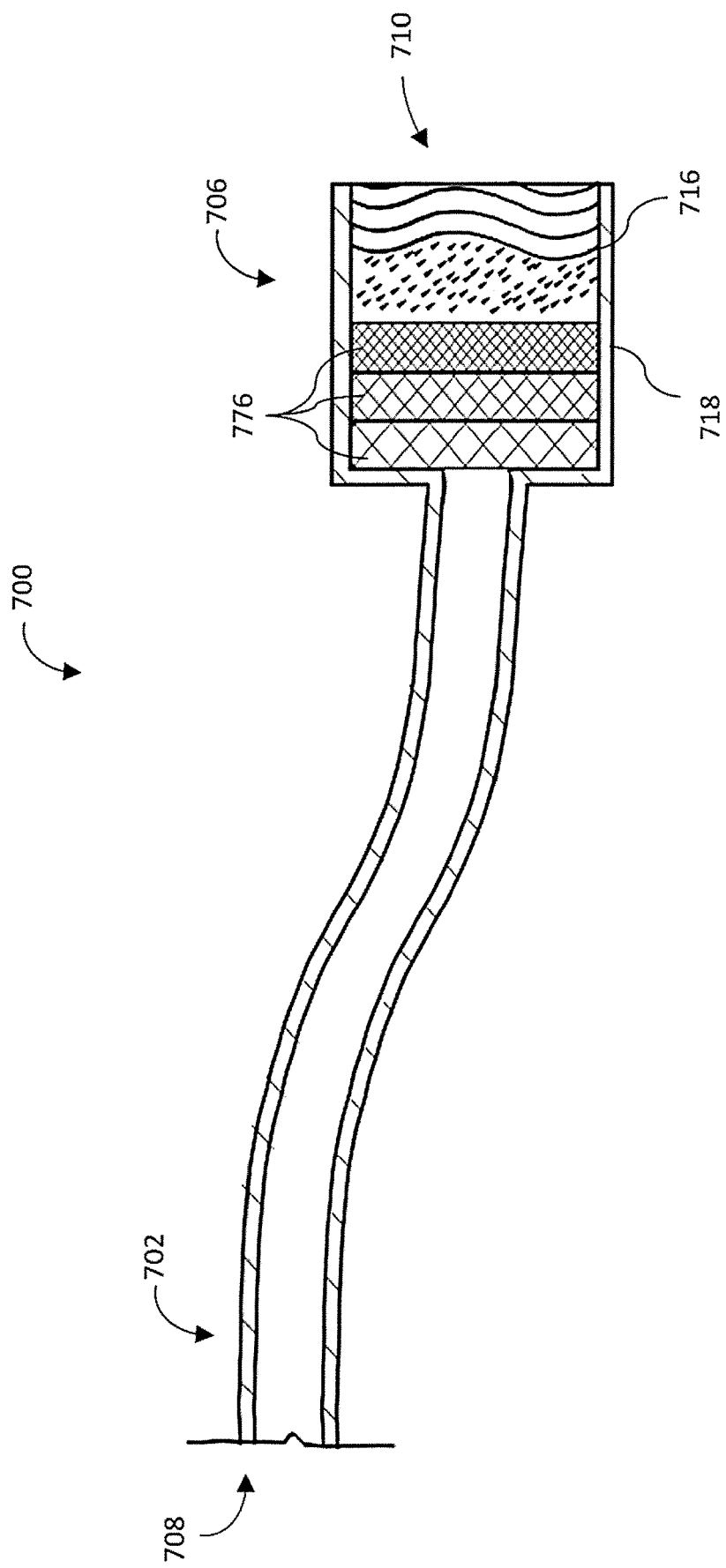
FIG. 32 illustrates a filter having multiple, additional filter stages.

FIGS. 31 and 32 illustrate a smoke filter 700 having a first portion 708 leading from a surgical site, a gases pathway 702 transporting smoke and/or gases exhausted from the surgical site, and a filter element 706. At least a portion of the gases pathway 702 may be surrounded by a flexible plastic tubing or an inflexible tubing. The filter element 706 may include one or more filter media 716, such as an activated carbon and/or particulate filter media (such as ULPA or HEPA), located within a housing 718. The gases pathway 702 extends to atmosphere through the filter element 706 such that the filtered smoke and/or gases are vented to atmosphere at the second portion 710.

The smoke filter 700 may also include a humidity regulating element upstream of or within the filter element 706. For example, the filter element 706 may also include one or more additional filter stages 776 in-line with, for example upstream of, the filter media 716 and within the housing 718. FIG. 31 illustrates the filter element 706 with one additional filter stage 776. The additional filter stage 776 may filter larger particles so that particle filtering is distributed across multiple filters. This prevents the downstream filter media 716 from being overloaded and clogged with larger particles from the humidity interaction. The downstream filter media 716 may have a smaller pore size than the filter stage 776.

FIG. 32 illustrates a filter element 706 with multiple filter stages 776, for example two, three, or more filter stages, that remove larger particles and lower the load on the downstream filter media 716. The filter stages 776 may include progressively smaller pore sizes toward the filter media 716. For example, the filter stages 776 may include a desiccant and/or activated carbon filter.

Figure 33:
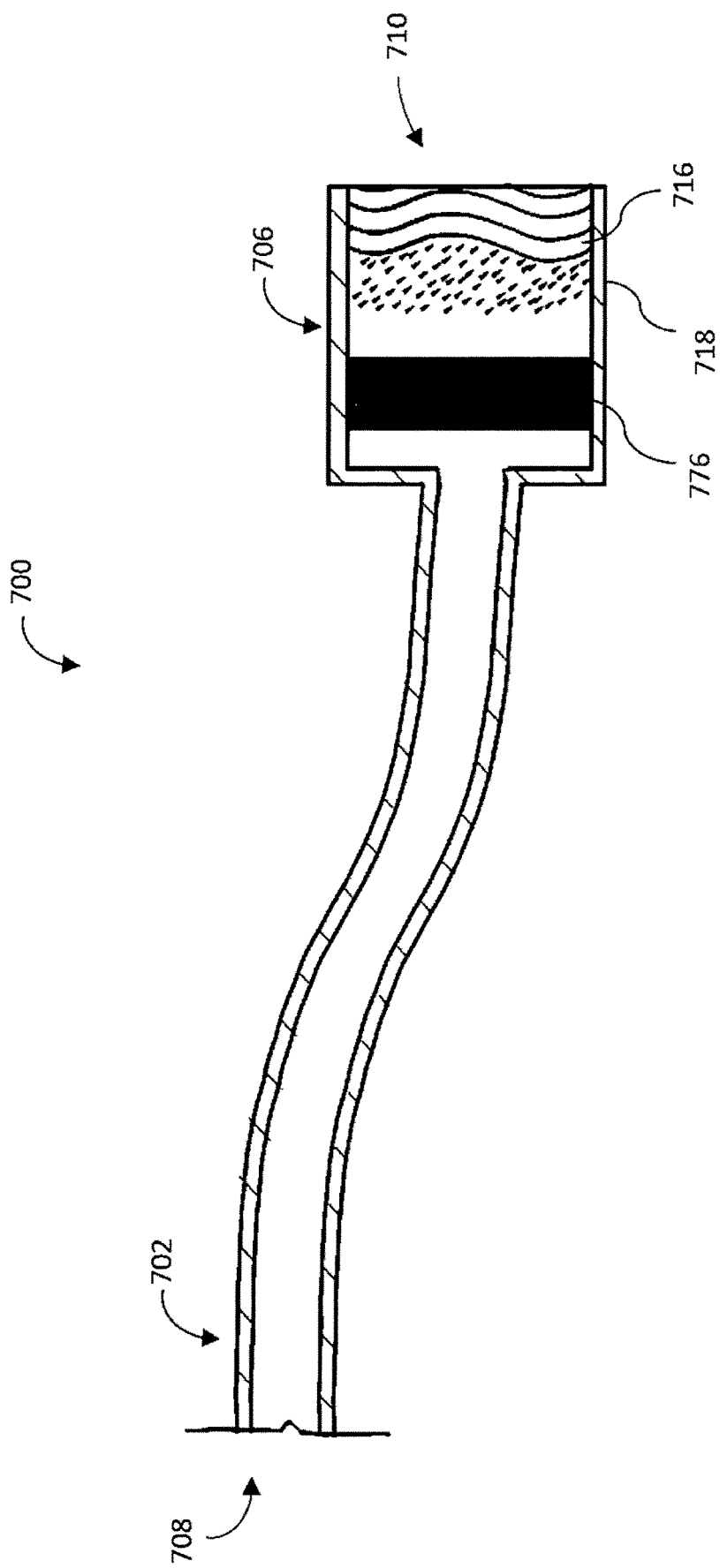
FIG. 33 illustrates a filter having a humidity filter.

FIG. 33 illustrates another smoke filter 700 with an additional filter stage 776 within the housing 718 and upstream of the filter media 716. The filter stage 776 pre-filters humidity out of the gas before the gas reaches the filter media 716. For example, the filter stage 776 may include a coalescing filter mechanism or a hydrophilic filter material.

Figure 34:
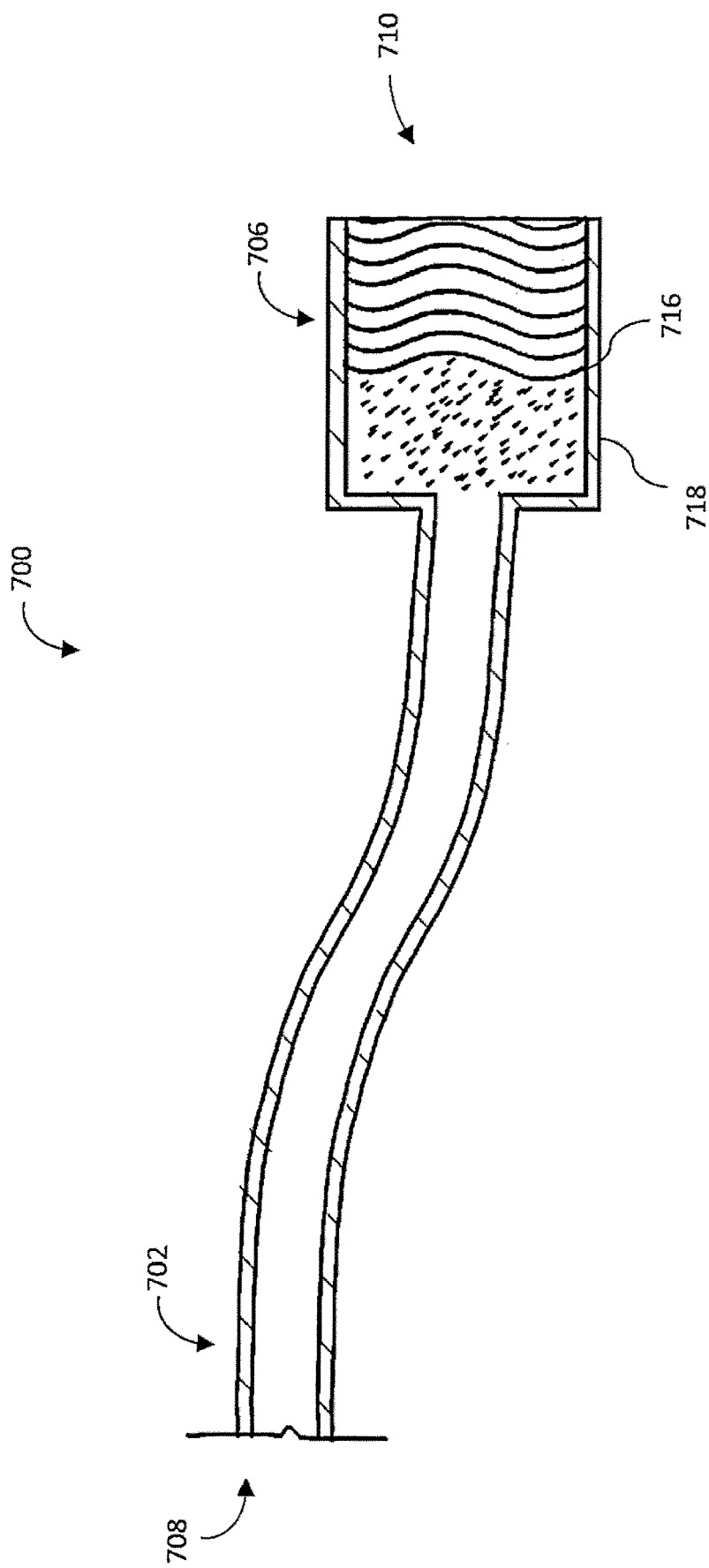
FIG. 34 illustrates a filter with a filter element having a hydrophobic material or coating.

FIG. 34 illustrates a smoke filter 700 having a first portion 708 leading from a surgical site, a gases pathway 702 transporting smoke and/or gases exhausted from the surgical site, and a filter element 706. At least a portion of the gases pathway 702 may be surrounded by a flexible plastic tubing or an inflexible tubing. The filter element 706 may include one or more filter media 716, such as an activated carbon and/or particulate filter media (such as ULPA or HEPA), located within a housing 718. The one or more filter media 716 may be manufactured or coated with a hydrophobic chemical or material to prevent absorption of water droplets into the filter media 716 and/or to prevent water nucleation on the filter media 716. The hydrophobic material or coating stops moisture from clogging the filter media 716. The gases pathway 702 extends to atmosphere through the filter element 706 such that the filtered smoke and/or gases are vented to atmosphere at the second portion 710.

Smoke Venting Filters with Pressure Changes

In some configurations, the humidity regulating element include a pressure device to manipulate pressures in the gas path and force humidity to condense before reaching the filtering element.

Figure 35:
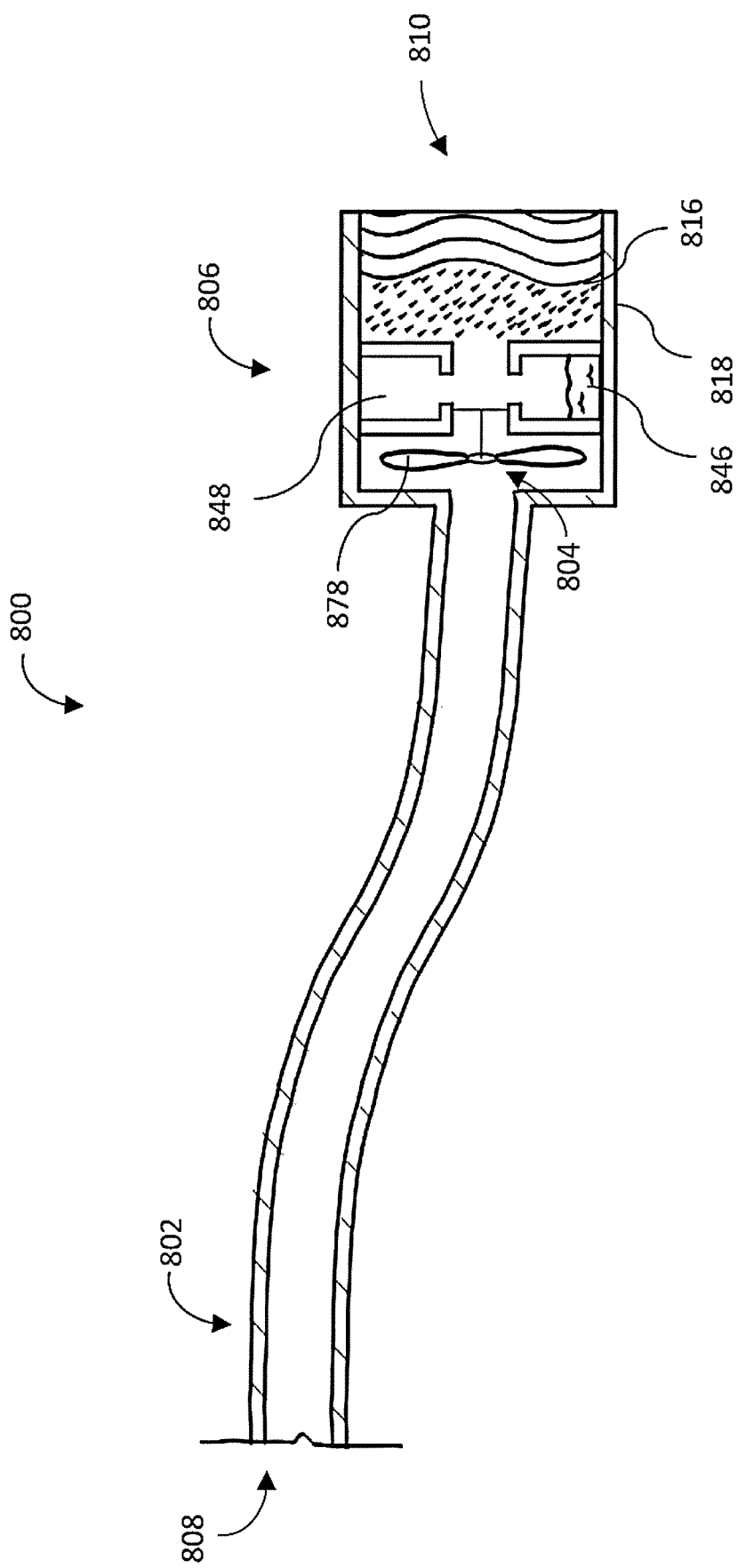
FIG. 35 illustrates a filter with a humidity regulating element having a pressure change device.

For example, FIG. 35 illustrates a smoke filter 800 with a pressure device 878. The smoke filter 800 may include a first portion 808 leading from a surgical site, a gases pathway 802 transporting smoke and/or gases exhausted from the surgical site, a humidity regulating element 804 located along the gases pathway 802, and a filter element 806 in fluid communication with the humidity regulating element 804. At least a portion of the gases pathway 802 may be surrounded by a flexible plastic tubing or an inflexible tubing. The humidity regulating element 804 may be at least partially or fully housed within the tubing of the gases pathway 802 and/or the filter element 806. As shown, the filter element 806 may include one or more filter media 816, such as an activated carbon and/or particulate filter media (such as ULPA or HEPA), located within a housing 818. The humidity regulating element 804 may include a pressure device 878, such as a fan, impeller, or pump, configured to manipulate pressures in the gases pathway 802 to force humidity to condense before it reaches the filter media 816. The pressure device 878 may be powered externally or through a battery. The humidity regulating element 804 may also include a reservoir 846 to collect the moisture condensed by the pressure change. The reservoir 846 may extend at least partially or fully around the gases pathway 802. The tubing may include one or more outlets 848 to allow the condensed moisture to drip into the reservoir 846. The pressure device 878 and/or the reservoir 846 may be positioned within the filter element housing 818. Viewed another way, the filter media 816 may be at least partially or entirely located within a housing of the humidity regulating element 804 and downstream from the pressure device 878 and the reservoir 846. The gases pathway 802 extends to atmosphere through the filter element 806 such that the filtered smoke and/or gases are vented to atmosphere at the second portion 810.

Figure 36:
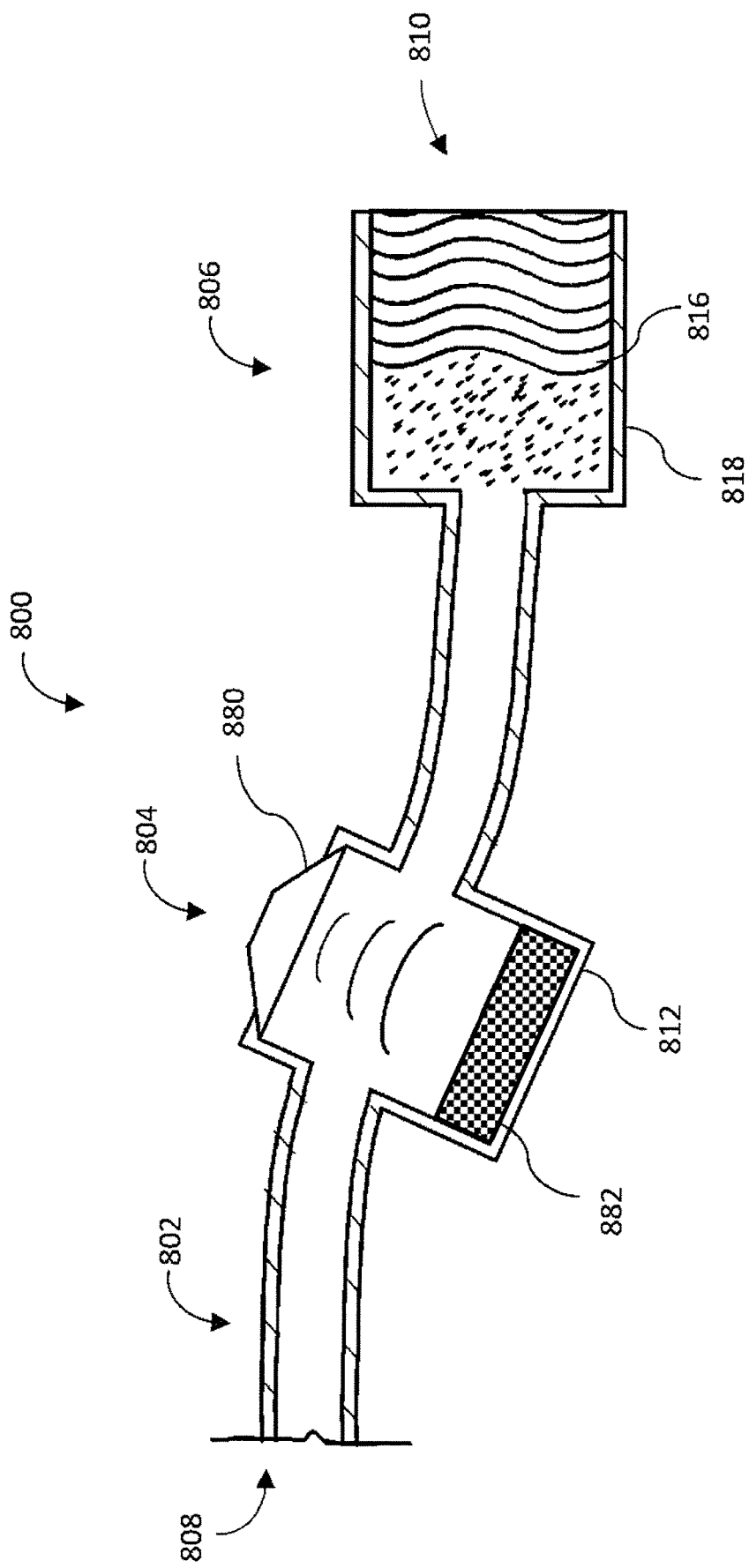
FIG. 36 illustrates a filter with a humidity regulating element having an acoustic device, such as, for example, a speaker.

FIG. 36 illustrates another example of a smoke filter 800 with an acoustic device 880, such as a speaker. The smoke filter 800 may include a first portion 808 leading from a surgical site, a gases pathway 802 transporting smoke and/or gases exhausted from the surgical site, a humidity regulating element 804 located along the gases pathway 802, and a filter element 806 downstream of the humidity regulating element 804 such that the humidity regulating element 804 and the filter element 806 are in fluid communication with each other. At least a portion of the gases pathway 802 may be surrounded by a flexible plastic tubing or an inflexible tubing. The humidity regulating element 804 may include a housing 812 with a pressure device such as an acoustic device 880, such as a speaker, that produces sound waves to cause a pressure change and condense moisture in the gas flow. The speaker device 880 may be powered by a battery or wired. The humidity regulating element 804 may also include an absorbent material 882 disposed within the housing 812 to trap water condensed by the acoustic device 880. The housing 812 or other structure may provide an acoustic resonance chamber to help reach an effective pressure to force condensation. Alternatively or additionally, the humidity regulating element 804 may include a reservoir, trap, permeable wall, desiccant material, wicking material, or other feature to prevent the condensed moisture from reaching the downstream filter element 806. The filter element 806 may include one or more filter media 816, such as an activated carbon and/or particulate filter media (such as ULPA or HEPA), located within a separate housing 818. The gases pathway 802 extends to atmosphere through the filter element 806 such that the filtered smoke and/or gases are vented to atmosphere at the second portion 810.

Other Smoke Venting Filters

Figure 37:
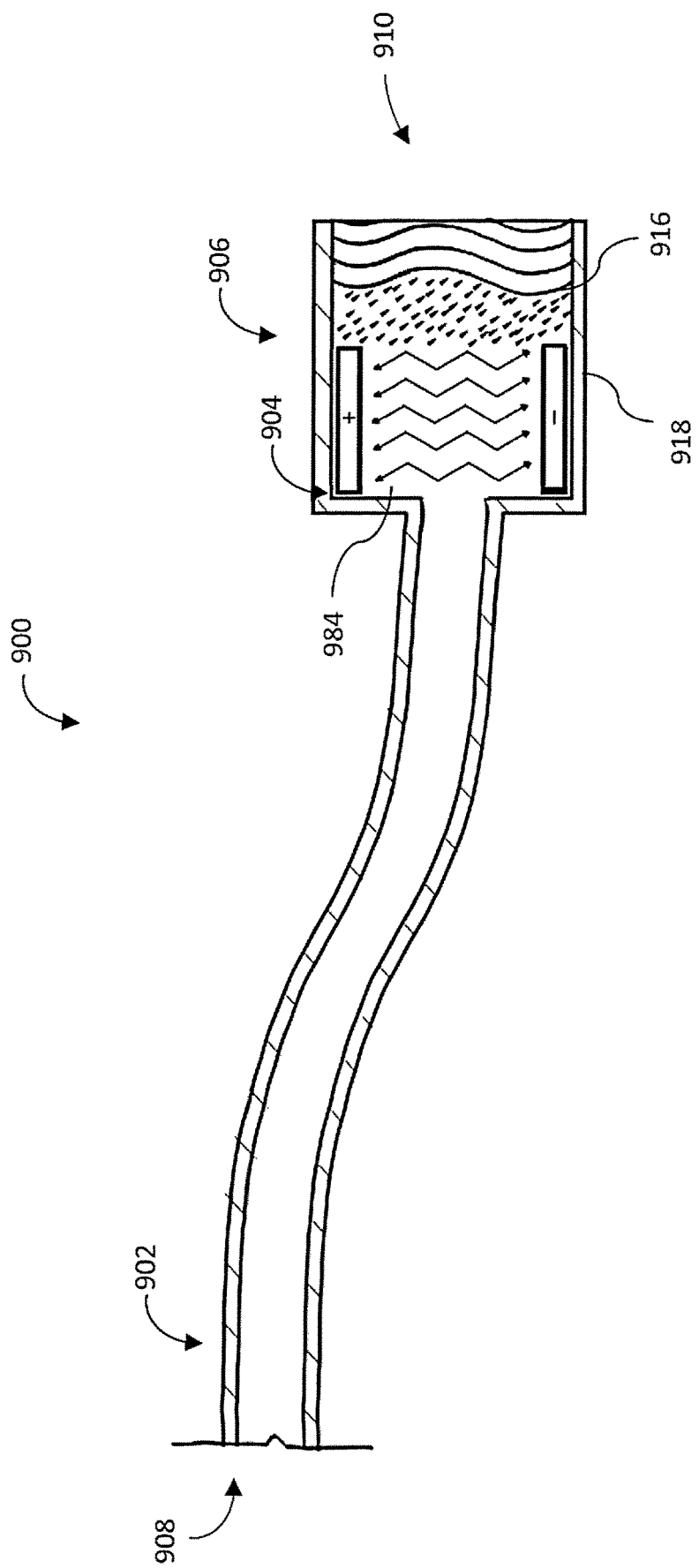
FIG. 37 illustrates a filter device with a humidity regulating element utilizing electrostatic forces.

FIG. 37 illustrates a smoke filter 900 to remove humidity using electrostatic forces. The smoke filter 900 may include a first portion 908 leading from a surgical site, a gases pathway 902 transporting smoke and/or gases exhausted from the surgical site, a humidity regulating element 904 located along the gases pathway 902, and a filter element 906 in fluid communication with the humidity regulating element 904. At least a portion of the gases pathway 902 may be surrounded by a flexible plastic tubing or an inflexible tubing. The humidity regulating element 904 may be at least partially or fully housed within the tubing of the gases pathway 902 and/or the filter element 906. As shown, the filter element 906 may include one or more filter media 916, such as an activated carbon and/or particulate filter media (such as ULPA or HEPA), located within a housing 918. The humidity regulating element 904 may force water molecules to bond to a surface of the filter element housing 918 or deconstruct the molecules into hydrogen and oxygen through electrolysis, for example by utilizing electric current or electrostatic forces 984. This removes moisture from the vented gas before the gas reaches the downstream filter media 916. Viewed another way, the filter media 916 may be at least partially or entirely located within a housing of the humidity regulating element 904 and downstream from the generation of electrostatic forces 984. The gases pathway 902 extends to atmosphere through the filter element 906 such that the filtered smoke and/or gases are vented to atmosphere at the second portion 910.

Methods of Retrofitting Standard Filters

Any of the smoke filters described herein may be retrofit to an existing smoke venting filter design, for example by placing the filter in series as shown in FIG. 4.

Figure 38:
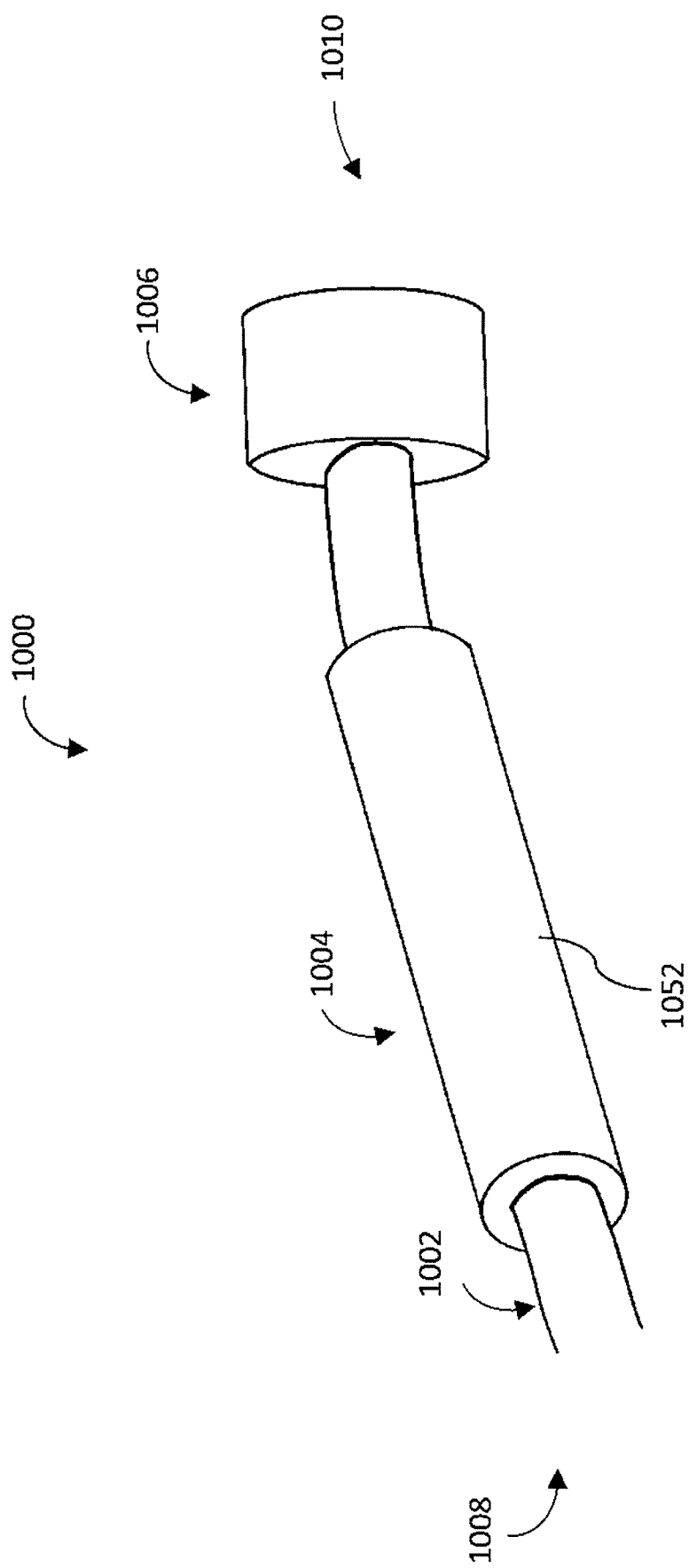
FIG. 38 illustrates a filter having a heatsink sleeve.

For example, FIG. 38 illustrates a heatsink sleeve 1052 that may be at least partially or fully wrapped around an existing smoke filter 1000. The smoke filter 1000 may include a first portion 1008 leading from a surgical site, a gases pathway 1002 transporting smoke and/or gases exhausted from the surgical site, a humidity regulating element 1004 located along the gases pathway 1002, and a filter element 1006 in fluid communication with the humidity regulating element 404. At least a portion of the gases pathway 1002 may be surrounded by a flexible plastic tubing or an inflexible tubing. The humidity regulating element 1004 may include a heatsink sleeve 1052 to be at least partially or fully wrapped around a portion of the gases pathway 1002 upstream of the filter element 1006. The heatsink sleeve 1052 cools the gas locally to force condensation. The humidity regulating element 1004 may also include a feature for collecting the condensed moisture before it reaches the filter element 1006, such as a reservoir, trap, permeable wall, wicking material, desiccant material, or other feature described above. The filter element 1006 may be positioned downstream of the humidity regulating element 1004. The gases pathway 1002 extends to atmosphere through the filter element 1006 such that the filtered smoke and/or gases are vented to atmosphere at the second portion 1010.

Figure 39:
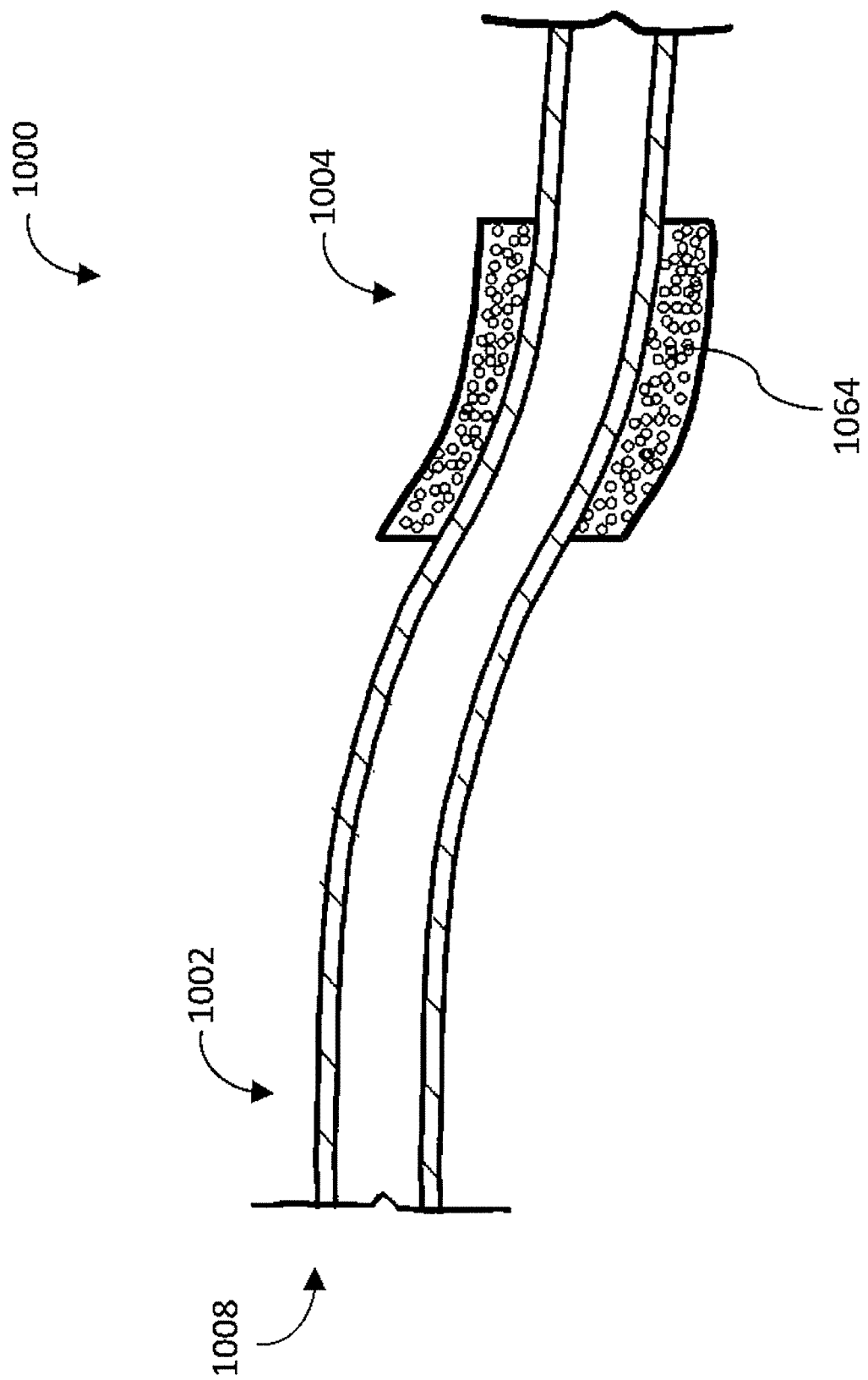
FIG. 39 illustrates a filter having a chemical cooling sleeve.

FIG. 39 illustrates a chemical cooling sleeve 1064 that may be at least partially or fully wrapped around an existing smoke filter 1000. The smoke filter 1000 may include a first portion 1008 leading from a surgical site, a gases pathway 1002 transporting smoke and/or gases exhausted from the surgical site, a humidity regulating element 1004 located along the gases pathway 1002, and a filter element (not shown) in fluid communication with the humidity regulating element 1004. At least a portion of the gases pathway 1002 may be surrounded by a flexible plastic tubing or an inflexible tubing. The humidity regulating element 1004 may include a chemical cooling sleeve 1064 to cool the tubing along a certain length. The humidity regulating element 1004 may also include a feature for collecting the condensed moisture before it reaches the filter element, such as a reservoir, trap, permeable wall, wicking material, desiccant material, or other feature described above. Similar to the previously described smoke filters, the filter element may be positioned downstream of the humidity regulating element 1004. The gases pathway 1002 extends to atmosphere through the filter element such that the filtered smoke and/or gases are vented to atmosphere at the second portion.

Figure 40:
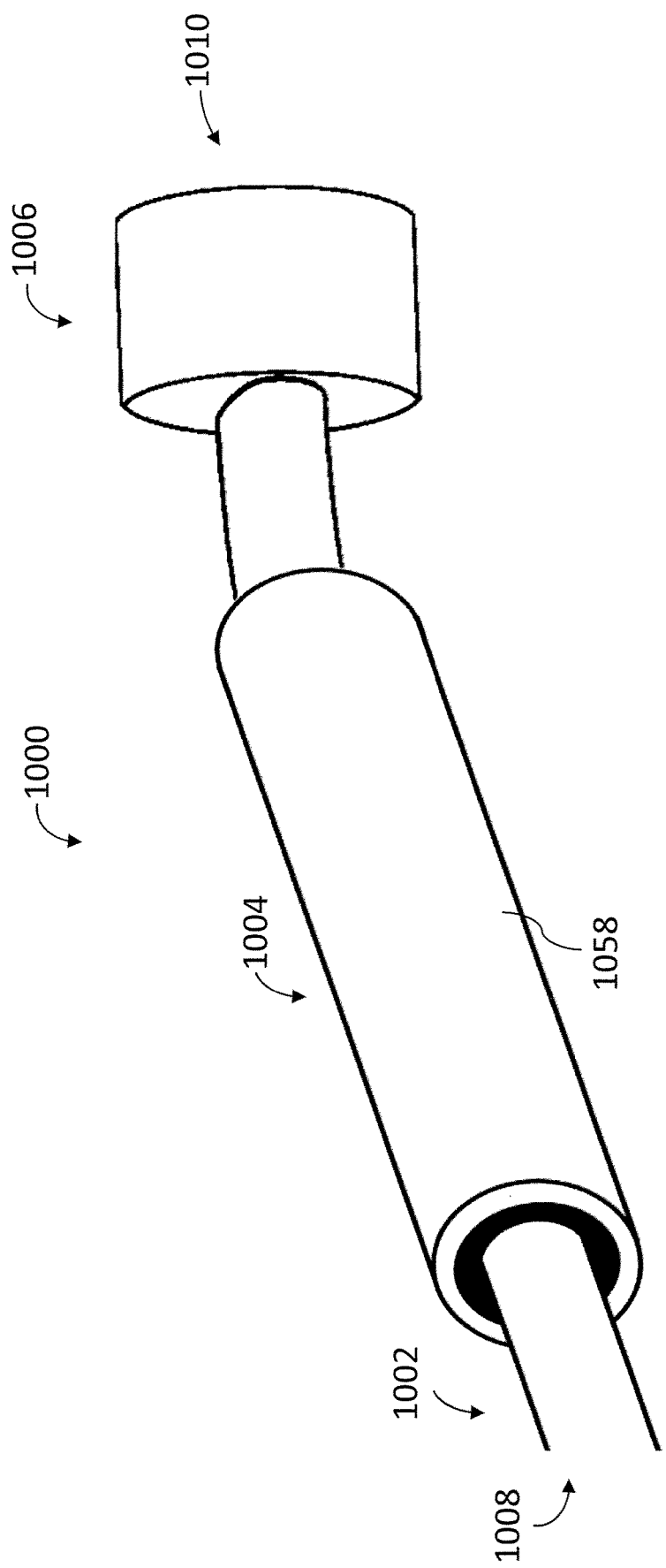
FIG. 40 illustrates a filter having a Peltier cooling sleeve.

FIG. 40 illustrates a Peltier cooling sleeve 1058 that may be at least partially or fully wrapped around an existing smoke filter 1000. The smoke filter 1000 may include a first portion 1008 leading from a surgical site, a gases pathway 1002 transporting smoke and/or gases exhausted from the surgical site, a humidity regulating element 1004 located along the gases pathway 1002, and a filter element 1006 in fluid communication with the humidity regulating element 1004. At least a portion of the gases pathway 1002 may be surrounded by a flexible plastic tubing or an inflexible tubing. The humidity regulating element 1004 may include a Peltier cooling sleeve 1058 to cool down the vented gas and force condensation. The humidity regulating element 1004 may also include a feature for collecting the condensed moisture before it reaches the filter element 1006, such as a reservoir, trap, permeable wall, wicking material, desiccant material, or other methods described above. The filter element 1006 may be positioned downstream of the humidity regulating element 1004. The gases pathway 1002 extends to atmosphere through the filter element 1006 such that the filtered smoke and/or gases are vented to atmosphere at the second portion 1010.

Figure 41:
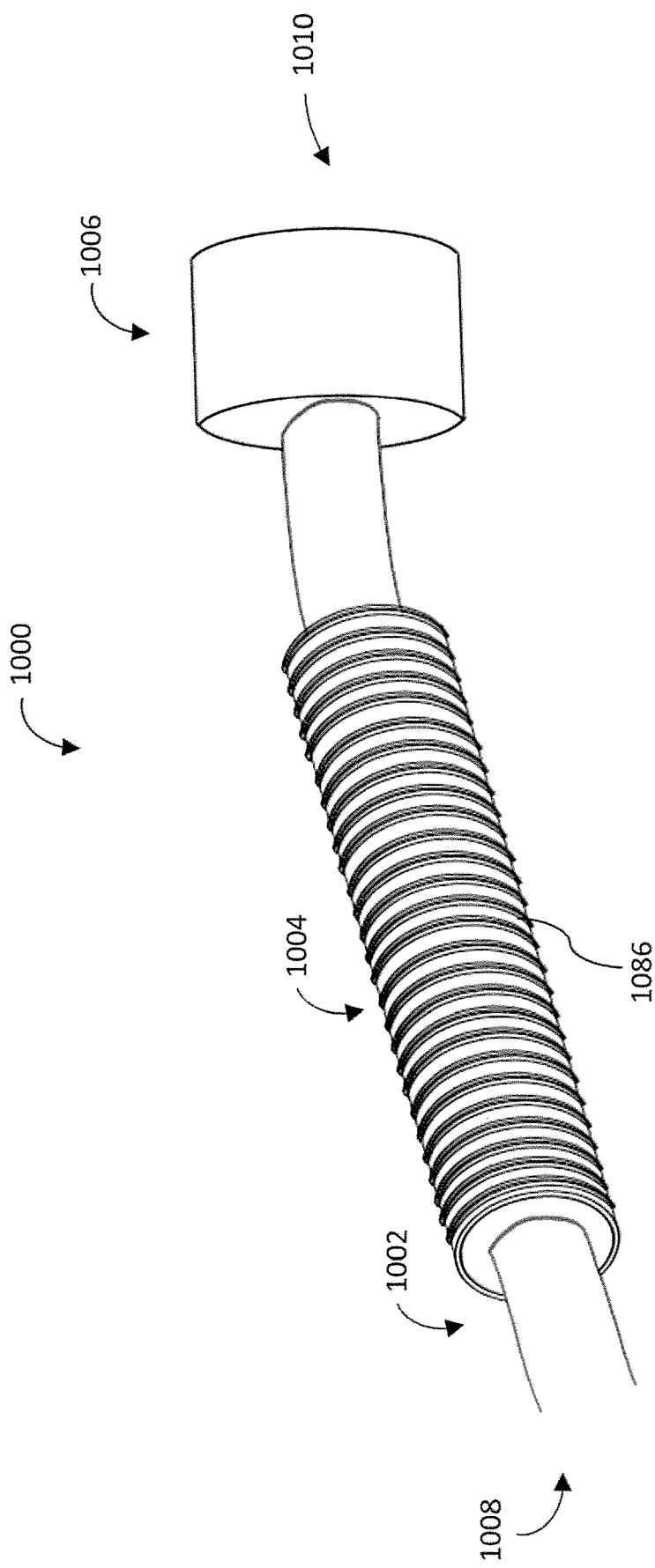
FIG. 41 illustrates a filter having a refrigerant sleeve.

FIG. 41 illustrates a refrigerant sleeve 1086 that may be at least partially or fully wrapped around an existing smoke filter 1000. The smoke filter 1000 may include a first portion 1008 leading from a surgical site, a gases pathway 1002 transporting smoke and/or gases exhausted from the surgical site, a humidity regulating element 1004 located along the gases pathway 1002, and a filter element 1006 in fluid communication with the humidity regulating element 1004. At least a portion of the gases pathway 1002 may be surrounded by a flexible plastic tubing or an inflexible tubing. The humidity regulating element 1004 may include a refrigerant sleeve 1086 to cool down the vented gas and force condensation. Coils in the refrigerant sleeve 1086 are wrapped around the gases pathway 1002. Refrigerant may be cycled through the coil to cool the gas passing through the refrigerant sleeve 1086. The humidity regulating element 1004 may also include a feature for collecting the condensed moisture before it reaches the filter element, such as a reservoir, trap, permeable wall, wicking material, desiccant material, or other methods described above. The filter element 1006 may be positioned downstream of the humidity regulating element 1004. The gases pathway 1002 extends to atmosphere through the filter element 1006 such that the filtered smoke and/or gases are vented to atmosphere at the second portion 1010.

Figure 42:
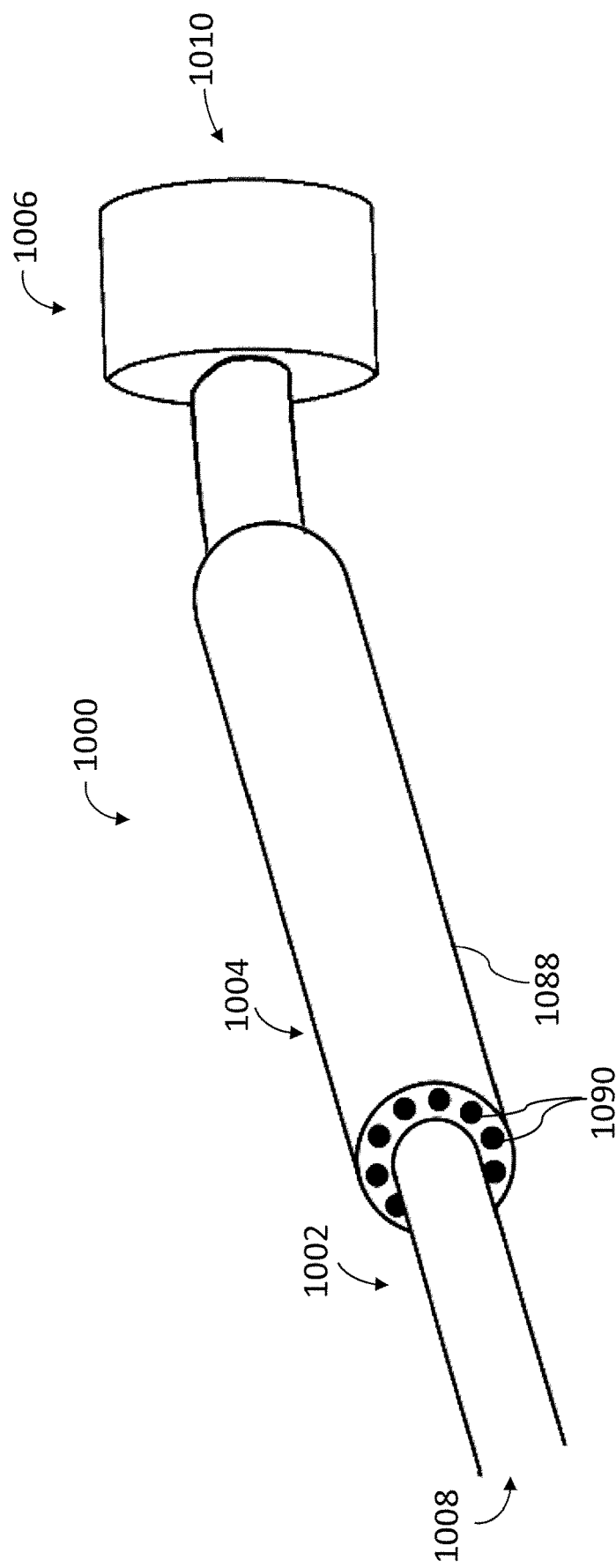
FIG. 42 illustrates a filter having a heater sleeve.

FIG. 42 illustrates a heater sleeve 1088 that may be at least partially or fully wrapped around an existing smoke filter 1000. The smoke filter 1000 may include a first portion 1008 leading from a surgical site, a gases pathway 1002 transporting smoke and/or gases exhausted from the surgical site, a humidity regulating element 1004 located along the gases pathway 1002, and a filter element 1006 in fluid communication with the humidity regulating element 1004. At least a portion of the gases pathway 1002 may be surrounded by a flexible plastic tubing or an inflexible tubing. The humidity regulating element 1004 may include a heater sleeve 1088 to raise the temperature of the gas above its dew point temperature to prevent condensation in the filter element 1006. The heater sleeve 1088 may include one or more heater wires 1090 as a method to heat the sleeve 1088. The filter element 1006 may be positioned downstream of the humidity regulating element 1004. The gases pathway 1002 extends to atmosphere through the filter element 1006 such that the filtered smoke and/or gases are vented to atmosphere at the second portion 1010.

Terminology

Although certain systems and methods herein may be described in connection with a humidification system, the systems and methods may be used without a humidification system. For example, any of the filters described herein may filter gases from the patient cavity.

Examples of medical gases delivery systems and associated components and methods have been described with reference to the figures. The figures show various systems and modules and connections between them. The various modules and systems can be combined in various configurations and connections between the various modules and systems can represent physical or logical links. The representations in the figures have been presented to clearly illustrate the principles and details regarding divisions of modules or systems have been provided for ease of description rather than attempting to delineate separate physical embodiments. The examples and figures are intended to illustrate and not to limit the scope of the inventions described herein.

As used herein, the term "processor" refers broadly to any suitable device, logical block, module, circuit, or combination of elements for executing instructions. For example, the controller 8 can include any conventional general purpose single- or multi-chip microprocessor such as a Pentium® processor, a MIPS® processor, a Power PC® processor, AMD® processor, ARM® processor, or an ALPHA® processor. In addition, the controller 122 can include any conventional special purpose microprocessor such as a digital signal processor or a microcontroller. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein, or can be a pure software in the main processor. For example, logic module can be a software-implemented function block which does not utilize any additional and/or specialized hardware elements. Controller can be implemented as a combination of computing devices, e.g., a combination of a DSP and a microprocessor, a combination of a microcontroller and a microprocessor, a plurality of microprocessors, one or more microprocessors in conjunction with a DSP core, or any other such configuration.

Data storage can refer to electronic circuitry that allows data to be stored and retrieved by a processor. Data storage can refer to external devices or systems, for example, disk drives or solid state drives. Data storage can also refer to fast semiconductor storage (chips), for example, Random Access Memory (RAM) or various forms of Read Only Memory (ROM), which are directly connected to the communication bus or the controller. Other types of data storage include bubble memory and core memory. Data storage can be physical hardware configured to store data in a non-transitory medium.

Although certain embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present. As used herein, the words "about" or "approximately" can mean a value is within ±10%, within ±5%, or within ±1% of the stated value.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A filter for a surgical procedure comprising:
   a fluid pathway to transport fluid exhausted from a surgical site;
   a humidity regulating element located within the fluid pathway;
   a filter element located within the fluid pathway downstream of the humidity regulating element such that the humidity regulating element and the filter element are in fluid communication with each other, the filter element comprising a filter element inlet and a filter element outlet;
   a filter housing containing the filter element and the humidity regulating element, the filter housing comprising:
      an inlet connector for connecting to the fluid pathway; and
      an outlet connector;
      an inner wall structure disposed within the filter housing configured to separate the humidity regulating element from the filter element; and
      a tapered structure extending from the inner wall structure in a direction toward the inlet connector;
   wherein the humidity regulating element is configured to remove or reduce humidity from the fluid exhausted from the surgical site prior to the fluid reaching the filter element, the filter element configured to filter particulate matter from the fluid exhausted from the surgical site; and
   wherein the filter element inlet extends into a region within the tapered structure to define a passageway of the fluid pathway between the tapered structure and the filter element inlet in a direction toward the inlet connector.

2. The filter for the surgical procedure according to claim 1, wherein the fluid pathway extends to atmosphere through the filter element such that filtered smoke and/or gases are vented to atmosphere after filtering.

3. The filter for the surgical procedure according to claim 1, wherein the humidity regulating element is in series with the filter element such that the filter element is spaced from and downstream of the humidity regulating element.

4. The filter for the surgical procedure according to claim 1, wherein the humidity regulating element is nested within the filter element such that the filter element partially surrounds a portion of the humidity regulating element, and the filter element is downstream in the fluid pathway.

5. The filter for the surgical procedure according to claim 1, wherein the humidity regulating element and the filter element are located in two separate compartments of the filter housing, the humidity regulating element being positioned upstream of the filter element.

6. The filter for the surgical procedure according to claim 1, wherein the humidity regulating element comprises a separate housing within the filter housing.

7. The filter for the surgical procedure according to claim 6, further comprising a passageway between the separate housing and an inner surface of the filter housing.

8. The filter for the surgical procedure according to claim 7, wherein the passageway directs the fluid toward a region within the separate housing.

9. The filter for the surgical procedure according to claim 7, wherein the separate housing comprises one or more guide elements configured to separate the separate housing from the inner surface of the filter housing to form the passageway.

10. The filter for the surgical procedure according to claim 1, wherein the humidity regulating element comprises a wicking or hydrophilic material positioned within the fluid pathway and upstream of the filter element.

11. The filter for the surgical procedure according to claim 10, wherein the wicking or hydrophilic material is located within the filter housing upstream of the filter element.

12. The filter for the surgical procedure according to claim 1, wherein the humidity regulating element is a permeable tube that is configured to allow moisture to escape the fluid pathway prior to the fluid entering the filter element.

13. The filter for the surgical procedure according to claim 1, wherein the humidity regulating element comprises a heatsink sleeve or a cooling sleeve wrapped around the fluid transport pathway upstream of the filter.

14. The filter for the surgical procedure according to claim 1, further comprising:
   a tube extending from the surgical site;
   a moisture removal compartment comprising desiccant;
   a filter compartment comprising a filter media to filter the particulate matter from smoke; and
   wherein the fluid pathway is defined through the tube, moisture removal compartment and filter compartment;
   wherein the moisture removal compartment is located upstream of the filter compartment, and wherein the fluid pathway is configured to vent to atmosphere such that the filtered smoke is vented to atmosphere.

15. The filter for the surgical procedure according to claim 1, wherein
   the humidity regulating element comprises a desiccant material.

16. The filter for the surgical procedure according to claim 1, wherein the inlet connector is coaxial with the filter element and/or the outlet connector.

17. The filter for the surgical procedure according to claim 1, wherein the inner wall structure comprises one or more openings configured to allow gasses to flow through the inner wall structure.

18. The filter for the surgical procedure according to claim 17, wherein, in use, gases flow around the tapered structure of the filter housing and through the humidity regulating element in a direction generally toward the one or more openings in the inner wall structure.

19. The filter for the surgical procedure according to claim 17, wherein, in use, gases flow from the humidity regulating element through the one or more openings in the inner wall structure and toward the inlet connector into the tapered structure.

20. The filter for the surgical procedure according to claim 1, further comprising a filter media inlet concentric with the tapered structure.

* * * * *